US008987230B2

(12) United States Patent
Akiyoshi et al.

(10) Patent No.: US 8,987,230 B2
(45) Date of Patent: Mar. 24, 2015

(54) HYBRID GEL COMPRISING CHEMICALLY CROSSLINKED HYALURONIC ACID DERIVATIVE AND PHARMACEUTICAL COMPOSITION COMPRISING THE SAME

(75) Inventors: Kazunari Akiyoshi, Bunkyo-ku (JP); Nobuyuki Morimoto, Bunkyo-ku (JP); Tai Hirakura, Gotenba (JP); Tsuyoshi Shimoboji, Gotenba (JP)

(73) Assignees: National University Corporation Tokyo Medical and Dental University, Tokyo (JP); Chugai Seiyaku Kabushiki Kaisha, Tokyo (JP)

( * ) Notice: Subject to any disclaimer, the term of this patent is extended or adjusted under 35 U.S.C. 154(b) by 912 days.

(21) Appl. No.: 12/598,498

(22) PCT Filed: Apr. 30, 2008

(86) PCT No.: PCT/JP2008/058593
§ 371 (c)(1),
(2), (4) Date: Apr. 26, 2010

(87) PCT Pub. No.: WO2008/136536
PCT Pub. Date: Nov. 13, 2008

(65) Prior Publication Data
US 2010/0204102 A1    Aug. 12, 2010

(30) Foreign Application Priority Data
May 1, 2007  (JP) ................. 2007-120872

(51) Int. Cl.
*A61K 31/715* (2006.01)
*A61K 31/728* (2006.01)
*A61K 31/719* (2006.01)
*A61K 31/718* (2006.01)
*A61K 31/721* (2006.01)
*A61K 31/722* (2006.01)
*A61K 9/00* (2006.01)
*A61K 9/06* (2006.01)
*A61K 9/08* (2006.01)
*A61K 47/36* (2006.01)

(52) U.S. Cl.
CPC ............... *A61K 9/0014* (2013.01); *A61K 9/06* (2013.01); *A61K 9/08* (2013.01); *A61K 47/36* (2013.01)
USPC ................ 514/54; 514/59; 514/55; 514/58; 514/60; 536/55.1; 536/102; 536/103; 536/112; 536/123.1

(58) Field of Classification Search
CPC . A61K 31/728; A61K 31/715; A61K 31/719; A61K 31/721; A61K 31/722; A61K 9/0014; A61K 47/36; A61K 9/08; A61K 9/06; A91K 9/14
USPC ........... 514/54, 59, 55, 58, 60; 536/55.1, 102, 536/103, 112, 123.1
See application file for complete search history.

(56) References Cited

U.S. PATENT DOCUMENTS

| 4,094,832 | A | * | 6/1978 | Soderberg | 526/238.22 |
|---|---|---|---|---|---|
| 4,582,865 | A | | 4/1986 | Balazs et al. | |
| 5,462,976 | A | | 10/1995 | Matsuda et al. | |
| 5,763,504 | A | | 6/1998 | Matsuda et al. | |
| 5,827,937 | A | | 10/1998 | Agerup | |
| 6,566,516 | B1 | | 5/2003 | Sunamoto et al. | |
| 2002/0192181 | A1 | | 12/2002 | Massia et al. | |
| 2002/0192182 | A1 | | 12/2002 | Massia et al. | |
| 2004/0185086 | A1 | | 9/2004 | Massia et al. | |
| 2006/0110458 | A1 | | 5/2006 | Hahn et al. | |
| 2007/0134334 | A1 | | 6/2007 | Hahn et al. | |
| 2009/0148534 | A1 | | 6/2009 | Yasugi et al. | |

FOREIGN PATENT DOCUMENTS

| EP | 0842657 | A1 | 5/1998 |
|---|---|---|---|
| JP | 61138601 | A | 6/1986 |
| JP | 5140201 | A | 6/1993 |
| JP | 6073102 | A | 3/1994 |
| JP | 2005298644 | A | 10/2005 |
| WO | 9402517 | A1 | 2/1994 |
| WO | 0012564 | A1 | 3/2000 |
| WO | 0044808 | A1 | 8/2000 |
| WO | 03047462 | A1 | 6/2003 |
| WO | 2004046200 | A1 | 6/2004 |
| WO | 2004050712 | A1 | 6/2004 |
| WO | 2005054301 | A1 | 6/2005 |
| WO | 2006028110 | A1 | 3/2006 |

OTHER PUBLICATIONS

Huin-amargier et al. (Journal of Biomaterial Materials Research Part A, vol. 76A, No. 2, 2005, pp. 416-424).*
Akiyoshi et al. (Macromolecules, vol. 30, 1997, No. 4, pp. 857-861).*
Huin-Amargier C. et al., "New physically and chemically crosslinked hyaluronate (HA)-based hydrogels for cartilage repair", Journal of Biomedical Materials Research Part A, vol. 76A, No. 2, 2005, pp. 416-424.
Palumbo S.F. et al., "New graft copolymers of hyaluronic acid and polylactic acid: Synthesis and characterization", Carbohydrate Polymers, vol. 66, 2006, pp. 379-385.

(Continued)

*Primary Examiner* — Shaojia Anna Jiang
*Assistant Examiner* — Michael C Henry
(74) *Attorney, Agent, or Firm* — Browdy and Neimark, P.L.L.C.

(57) ABSTRACT

The present invention provides a composition comprising a hyaluronic acid derivative having a crosslinking group(s) and a hydrophilic polysaccharide derivative having a hydrophobic group(s), wherein the hyaluronic acid derivative having a crosslinking group(s) is prepared by crosslinkage formation reaction in hyaluronic acid or a derivative thereof having a crosslinkable group(s) in the presence of the hydrophilic polysaccharide derivative wherein the hydrophilic polysaccharide derivative may have a crosslinkable group(s).

17 Claims, 18 Drawing Sheets

(56) References Cited

OTHER PUBLICATIONS

Creuzet C. et al., "New associative systems based on alkylated hyaluronic acid. Synthesis and aqueous solution properties", Polymer, vol. 47, No. 8, 2006, pp. 2706-2713.

Morimoto N. et al., "Design of Hybrid Hydrogels With Self-Assembled Nanogels as Cross-Linkers: Interaction with Proteins and Chaperone-Like Activity", Biomacromolecules, vol. 6, No. 4, 2005, pp. 1829-1834.

Nishikawa T. et al., "Macromolecular Complexation between Bovine Serum Albumin and the Self-Assembled Hydrogel Nanoparticle of Hydrophobized Polysaccharides", Journal of the American Chemical Society, vol. 118, No. 26, 1996, pp. 6110-6115.

Nishikawa T. et al., "Supramolecular Assembly Between Nanoparticles of Hydrophobized Polysaccharide and Soluble Protein Complexation between the Self-Aggregate of Cholesterol-Bearing Pullulan and alpha-Chymotrypsin", Macromolecules, vol. 27, No. 26, 1994, pp. 7654-7659.

Akiyoshi K. et al., "Microscopic Structure and Thermoresponsiveness of a Hydrogel Nanoparticle by Self-Assembly of a Hydrophobized Polysaccharide", Macromolecules, vol. 30, 1997, No. 4, pp. 857-861.

Akiyoshi K. et al., "Self-Aggregates of Hydrophobized Polysaccharides in Water. Formation and Characteristics of Nanoparticles", Macromolecules, vol. 26, No. 12, 1993, pp. 3062-3068.

Carrasquillo K. et al., "On the structural preservation of recombinant human growth hormone in a dried film of a synthetic biodegradable polymer", Journal of Pharmaceutical Sciences, vol. 88, No. 2, Feb. 1999, pp. 166-173.

Crotts, G. et al., "Protein delivery from poly(lactic-co-glycolic acid) biodegradable microspheres: Release kinetics and stability issues", Journal of Microencapsulation, Jan. 1998, vol. 15, No. 6, pp. 699-713.

Pouyani T. et al., "Novel Hydrogels of Hyaluronic Acid: Synthesis, Surface Morphology, and Solid-State NMR", Journal of the American Chemical Society, 1994, vol. 116, No. 17, pp. 7515-7522.

Akiyoshi K. et al., "Molecular Chaperone-Like Activity of Hydrogel Nanoparticles of Hydrophobized Pullulan: Thermal Stabilization with Refolding of Carbonic Anhydrase B", Bioconjugate Chemistry, 1999, vol. 10, No. 3, pp. 321-324.

Nomura Y. et al., "Protein refolding assisted by self-assembled nanogels as novel artificial molecular chaperone", FEBS Letters, vol. 553, No. 3, Oct. 2003, pp. 271-276.

Bulpitt, P. et al., "New strategy for chemical modification of hyaluronic acid: Preparation of functionalized derivatives and their use in the formation of novel biocompatible hydrogels", Journal of Biomedical Materials Research, vol. 47, No. 2, Nov. 1999, pp. 152-169.

Akiyoshi K. et al., "Self-assembled hydrogel nanoparticle of cholesterol-bearing pullulan as a carrier of protein drugs: Complexation and stabilization of insulin", Journal of Controlled Release, vol. 54, No. 3, Aug. 14, 1998, pp. 313-320.

Nobuyuki Morimoto et al, Hybrid Nanogels 1-21 with Physical and Chemical Cross-Linking Structures as Nanocarriers, Macromolecular Bioscience, Aug. 2005, pp. 710-716, vol. 5, no. 8, WILEY-VCH Verlag GmbH & Co. KGaA, Wernheirn, Germany.

European Search Report, Application No. EP 08752479, Jul. 5, 2013, The Hague, the Netherlands.

* cited by examiner 11-1  11-2    11-3  11-4    11-5  11-6

HYBRID GEL COMPRISING CHEMICALLY CROSSLINKED HYALURONIC ACID DERIVATIVE AND PHARMACEUTICAL COMPOSITION COMPRISING THE SAME

TECHNICAL FIELD

The present invention relates to a novel hybrid gel composed of a hyaluronic acid derivative and a polysaccharide modified to have a hydrophobic group(s) or a derivative thereof, a process for preparing the hybrid gel, and a pharmaceutical composition comprising the hybrid gel, particularly a sustained-release formulation which allows sustained release of a pharmacologically active protein or peptide.

BACKGROUND ART

In recent years, an increasing number of formulations of pharmacologically active proteins or peptides have been developed for practical use. In general, proteins or peptides are difficult to prepare as oral formulations due to their low stability in the gastrointestinal tract and low absorption from the intestinal tract membrane. For this reason, proteins or peptides are mostly used as injections in clinical practice. However, proteins or peptides usually have a short half-life in blood, and hence must be administered repeatedly at frequent intervals when used as drugs, thus imposing excessive burdens on patients. There is therefore a demand for practical sustained-release formulations of proteins or peptides, which exert their efficacy in as small amounts as possible and which permit reduced frequency of administration. Likewise, in the case of low-molecular-weight compounds when administered as drugs, there is also a high need for long-acting formulations intended to prolong drug efficacy.

Moreover, sustained-release formulations of proteins or peptides have a problem in that denaturation or aggregation of the proteins or peptides will occur during formulation process or in the formulations after in vivo administration. Means for preventing such denaturation or aggregation to avoid a reduction in the recovery rate are very beneficial in terms of increasing their bioavailability.

Attempts have been made to prepare sustained-release formulations based on a biodegradable polymer matrix such as polylactic acid-polyglycolic acid copolymer (PLGA), but such formulations are reported to cause protein denaturation and/or aggregation due to matrix hydrophobicity and/or as a result of manipulations required for formulation (e.g., emulsification, drying, acidification) (see Non-patent Documents 1 and 2). On the other hand, there are also reports of sustained-release formulations based on a hydrophilic hydrogel matrix with reduced risks of these problems, but no such formulations are yet available for practical application. In terms of safety, materials used for formulations should have non-antigenicity, non-mutagenicity, non-toxicity and biodegradability. Thus, no sustained-release formulation is now ready for practical use in all aspects, i.e., encapsulation efficiency and recovery rate of proteins or peptides, as well as safety.

Some recent reports have proposed the use of polysaccharides as matrixes for drug carriers. Among them, hyaluronic acid (HA), a biomaterial (polysaccharide) isolated from the vitreous body of bovine eyes in 1934 by K. Meyer, has been known as a major component of extracellular matrix for a long time. HA is a kind of glycosaminoglycan composed of disaccharide units in which D-glucuronic acid and N-acetyl-glucosamine are linked to one another via $\beta(1\rightarrow 3)$ glycosidic linkages. There is no difference among species in the chemical and physical structure of HA and humans also have a metabolic system for HA; HA is therefore one of the safest medical biomaterials in terms of immunity and toxicity. Recent years have enabled microbial mass production of high-molecular-weight HA and also have allowed practical use of HA in the fields of therapeutic agents for degenerated cartilage, cosmetics, etc.

There are some reports of an attempt to sustainedly release a protein or peptide as a drug from a gel which is composed of chemically crosslinked HA, because HA has non-antigenicity, non-mutagenicity, non-toxicity and biodegradability and appears to be preferred in terms of safety. Techniques known for gelling HA by chemical crosslinking include the carbodiimide (CDI) method (see Patent Document 1), the divinylsulfone (DVS) method (see Patent Document 2), and the glycidyl ether (GE) method (see Patent Document 3). Another technique is also known, in which HA is modified to have hydrazide (HZ) groups as crosslinking functional groups and the resulting HA derivative (HA-HZ) is then crosslinked with a crosslinking agent (see Non-patent Document 3).

There are also reports of sustained-release formulations which encapsulate a protein or peptide within a HA gel by in situ crosslinking (see, e.g., Patent Document 4). In the process for such in situ crosslinked sustained-release formulations, it is desired to have a smaller influence on drugs. To minimize reactions in proteins and peptides, a method has been reported that uses crosslinking reaction by oxidation of mercapto groups under mild conditions to prepare a drug-encapsulating HA gel (see Patent Document 5), but this method still has room for improvement when applied to proteins or peptides containing cysteine residues. Also, another method has been reported to minimize reactions with proteins or peptides, in which polyethylene glycol (PEG) is used as a matrix and crosslinked through nucleophilic addition reaction of unsaturated functional groups (see Patent Document 6), but this method has problems in reaction selectivity and versatility, and also suffers from a problem in that fragments of non-biodegradable PEG remain in the body, as described above.

Protein or peptide denaturation induced by side reactions may be responsible not only for reduced biological activity, but also for antigenicity development. Thus, reactions used for gel crosslinking must be highly selective without affecting a protein or peptide to be encapsulated. However, there is not known any in situ crosslinking method that is sufficient to solve all of these problems, i.e., reaction selectivity, versatility and safety.

In contrast, when a protein or peptide is encapsulated into a pre-crosslinked gel, it is advantageous in that side reactions between drug and matrix during chemical crosslinking can be completely avoided. Moreover, it is possible to remove the excess of crosslinking agent in the absence of the drug by washing the gel after chemical crosslinking and/or to eliminate unreacted crosslinking functional groups by reaction with another reactive group. Thus, it is also advantageous in that problems of contamination arising from unreacted crosslinking functional groups and residual crosslinking agent can be avoided. However, such an approach results in low encapsulation efficiency due to problems arising from compatibility and/or electrostatic repulsion between HA and protein or peptide, and it also has a problem in that it fails to provide sustained-release properties.

Previous reports have shown that a polysaccharide which is obtained by introducing hydrophobic groups (e.g., groups including a cholesterol group, an alkyl group and the like) into a hydrophilic polysaccharide (the polysaccharide thus obtained is hereinafter also referred to as "hydrophobized polysaccharide" or "HP") spontaneously associates in an aqueous solution to form a nano-size particulate (nanogel) having a hydrogel structure (see Non-patent Documents 4 and 5), that this nanogel serves as a host molecule which is complexed with a hydrophobic low-molecular-weight substance, a peptide, a protein or the like (see Non-patent Documents 4, 6 and 7), and that this nanogel serves as an artificial molecular chaperone which facilitates heat stabilization and/or refolding of proteins (see Non-patent Documents 8 and 9). Moreover, further reports have been issued for hybrid gels prepared from this nanogel by being modified to have polymerizable groups (e.g., methacryloyl groups) and then crosslinked by copolymerization with functional monomers (see Patent Document 8 and Non-patent Document 10).

Patent Document 1: International Publication No. WO94/02517
Patent Document 2: JP 61-138601 A
Patent Document 3: JP 5-140201 A
Patent Document 4: U.S. Pat. No. 5,827,937
Patent Document 5: International Publication No. WO2004/046200
Patent Document 6: International Publication No. WO2000/44808
Patent Document 7: International Publication No. WO2004/050712
Patent Document 8: JP 2005-298644 A
Patent Document 9: International Publication No. WO2006/028110
Patent Document 10: International Publication No. WO00/12564
Patent Document 11: European Publication No. 0842657
Patent Document 12: International Publication No. WO2005/054301
Non-patent Document 1: J. Pharm. Sci., vol. 88, pp. 166-173, 1999
Non-patent Document 2: J. Microencapsulation, vol. 15, pp. 699-713, 1998
Non-patent Document 3: J. Am. Chem. Soc., vol. 116, pp. 7515-7522, 1994
Non-patent Document 4: Macromolecules, vol. 26, pp. 3062-3068, 1993
Non-patent Document 5: Macromolecules, vol. 30, pp. 857-861, 1997
Non-patent Document 6: Macromolecules, vol. 27, pp. 7654-7659, 1994
Non-patent Document 7: J. Am. Chem. Soc., vol. 118, pp. 6110-6115, 1996
Non-patent Document 8: Bioconjugate Chem., vol. 10, pp. 321-324, 1999
Non-patent Document 9: FEBS Letters, vol. 533, pp. 271-276, 2003
Non-patent Document 10: Biomacromolecules, vol. 6, pp. 1829-1834, 2005
Non-patent Document 11: J. Biomedical Materials Research, vol. 47, pp. 152-169, 1999
Non-patent Document 12: J. Controlled Release, vol. 54, pp. 313-230, 1998

DISCLOSURE OF THE INVENTION

Problems to be Solved by the Invention

To date, there has not been known a process for preparation of a gel based on highly safe hyaluronic acid which is chemically crosslinked in situ and enables efficient encapsulation and long-term sustained release of drugs, particularly pharmacologically active proteins or peptides, while retaining their biological activity. Moreover, no gel is known which allows efficient encapsulation of a drug into a pre-crosslinked HA gel and long-term sustained release of the drug. Further, there is no knowledge about a process for preparation of such a gel or a sustained-release formulation using the same.

A problem to be solved by the invention is to provide a drug carrier for sustained-release formulations, which allows long-term sustained release and is excellent in safety. More particularly, a problem to be solved by the invention is to provide a drug carrier for use in sustained-release formulations comprising a pharmacologically active protein or peptide as a drug, which allows efficient encapsulation of the drug while retaining its pharmacological activity.

Means for Solving the Problems

As a result of extensive and intensive efforts made to overcome the problems stated above, the inventors of the present invention have found that a hybrid gel prepared by using a hyaluronic acid derivative and a hydrophilic polysaccharide derivative having a hydrophobic group(s) achieves efficient encapsulation and long-term sustained release of drugs, particularly pharmacologically active proteins or peptides, while retaining their biological activity, and thus serves as a sustained-release drug carrier which is biodegradable and free from any problem of safety. This finding led to the completion of the present invention.

Namely, the present invention relates to a hybrid gel comprising a hyaluronic acid derivative and a hydrophilic polysaccharide derivative having a hydrophobic group(s), which allows efficient encapsulation of drugs, particularly pharmacologically active proteins or peptides, while retaining their biological activity, a process for preparing the hybrid gel, as well as a sustained-release formulation obtainable by drug encapsulation into the hybrid gel and a process for preparing the formulation.

In one aspect, the present invention provides a hybrid gel comprising a hyaluronic acid derivative and a hydrophilic polysaccharide derivative having a hydrophobic group(s). According to the above aspect, the hybrid gel of the present invention is a gel-form composition, which comprises a hyaluronic acid derivative and a hydrophilic polysaccharide derivative having a hydrophobic group(s) and which has both a chemically crosslinked structure formed by chemical bonding and a physically crosslinked structure formed by hydrophobic interaction.

As used herein, the term "gel" is intended to include hydrogels (swollen with water to reduce or lose their fluidity), organogels (swollen with an organic solvent to reduce or lose their fluidity), xerogels (dry form of hydrogels or organogels), etc.

Preparation techniques for gel-containing pharmaceutical compositions include those in which a hydrogel or organogel is formed after or simultaneously with drug encapsulation and then dried to give a xerogel; those in which a drug is encapsulated into a hydrogel or organogel, followed by drying to give a xerogel; and those in which a xerogel is converted in to a hydrogel by addition of water, followed by drug encapsulation.

In one aspect, the present invention provides a composition comprising a hyaluronic acid derivative having a crosslinking group(s) and a hydrophilic polysaccharide derivative having a hydrophobic group(s), wherein the hyaluronic acid derivative having a crosslinking group(s) is prepared by crosslinkage formation reaction in hyaluronic acid or a derivative thereof having a crosslinkable group(s) in the presence of the hydrophilic polysaccharide derivative which forms a particulate upon association of the hydrophobic groups wherein the hydrophilic polysaccharide derivative may have a crosslinkable group(s).

In another aspect, the present invention provides a composition comprising a hyaluronic acid derivative having a crosslinking group(s) and a hydrophilic polysaccharide derivative having a hydrophobic group(s), wherein the hyaluronic acid derivative having a crosslinking group(s) is prepared by crosslinkage formation in hyaluronic acid or a derivative thereof having a crosslinkable group(s) in a solution (e.g., aqueous solution) containing the hydrophilic polysaccharide which forms a particulate upon association of the hydrophobic groups wherein the hydrophilic polysaccharide derivative may have a crosslinkable group(s).

The composition of the present invention may be in the form of a gel (e.g., hydrogel or xerogel). In a case where the composition of the present invention is a xerogel, the water content is, for example, 20% by weight or less, preferably 10% by weight or less. Thus, in one embodiment, the present invention is directed to a gel-form composition.

The hyaluronic acid derivative in the present invention is intended to mean a derivative obtained by introducing a substituent into at least one or more carboxy or hydroxy groups in hyaluronic acid or by forming a salt. Non-limiting examples of a substituent include crosslinkable groups such as an amino group, a mercapto group, a formyl group, $-CONHNH_2$, a group containing a carbon-carbon double bond, and a group containing a carbon-carbon triple bond. Such a substituent may be attached via a spacer.

To introduce such a crosslinkable group, one or more carboxy groups in hyaluronic acid may be converted into $-CO-Y$, wherein examples of the group Y include those listed below:
— $X^{11}-R^{12}-Y^2$;
— $X^{11}-R^{12}-X^{12}-CO-R^{13}-Y^2$;
— $X^{11}-R^{12}-X^{12}-C(=NR^{24})-R^{13}-Y^2$;
— $X^{11}-R^{12}-CO-X^{13}-R^{13}-Y^2$;
— $X^{11}-R^{12}X^{12}-CO-X^{13}-R^{13}-Y^2$;
— $N(R^{11})N(R^{14})CO-R^{12}-Y^2$;
— $N(R^{11})N(R^{14})CO-R^{12}-CON(R^{15})N(R^{16})CO-R^{13}-Y^2$; and
— $N(R^{11})N(R^{14})CO-R^{12}-CON(R^{15})N(R^{16})C(=NR^{24})-R^{13}-Y^2$ wherein $X^{11}$, $X^{12}$ and $X^{13}$ are each independently selected from O and $N(R^{11})$;

$Y^2$ is selected from an amino group, a mercapto group, a formyl group, $-CONHNH_2$, a group containing a carbon-carbon double bond, and a group containing a carbon-carbon triple bond;

$R^{11}$; $R^{14}$; $R^{15}$; $R^{16}$ and $R^{24}$ are each independently selected from a hydrogen atom or a $C_{1-6}$ alkyl group;

$R^{12}$ is a divalent $C_{2-50}$ hydrocarbon group or a divalent $C_{2-50}$ polyalkyleneoxy group;

$R^{13}$ is a divalent $C_{1-50}$ hydrocarbon group, a divalent $C_{2-50}$ polyalkyleneoxy group or $-CH(R^{25})-CH_2-S-CH_2-R^{26}-CH_2-$; wherein if $R^{12}$ and $R^{13}$ are each a divalent $C_{2-50}$ hydrocarbon group, the hydrocarbon group may partially contain a polyalkyleneoxy moiety by insertion of 1 to 10 oxygen atoms; or $-R^{13}-Y^2$ together represent $-CH(NH_2)CH_2SH$; or $-CH(NH_2)CH_2CH_2SH$; or $-X^{11}-R^{12}-Y^2$ together represent a cysteine, homocysteine or glutathione group whose terminal amino group is used for attachment;

$R^{25}$ is a hydrogen atom or a $C_{1-6}$ alkyl group;

$R^{26}$ is $-(CH(R^{27}))_m-$ or a divalent $C_{2-10}$ hydrocarbon group which may partially contain a polyalkyleneoxy moiety by insertion of 1 to 3 oxygen atoms;

m is an integer of 1 to 10; and $R^{27}$ is independently selected from a hydrogen atom, a hydroxy group or a $C_{1-6}$ alkyl group.

As used herein, the phrase "cysteine, homocysteine or glutathione group whose terminal amino group is used for attachment" is intended to mean the groups listed below, respectively:
—$NHCH(CO_2H)-(CH_2)-SH$
—$NHCH(CO_2H)-(CH_2)_2-SH$
—$NHCH(CO_2H)-(CH_2)_2CONH-CH(CONHCH_2CO_2H)-CH_2SH$.

Preferably, $Y^2$ is selected from an amino group, a mercapto group, a formyl group, $-CONHNH_2$, and a group containing a carbon-carbon double bond; or together with $-R^{13}-$, $Y^2$ represents $-CH(NH_2)CH_2SH$ or $-CH(NH_2)CH_2CH_2SH$; or together with $-X^{11}-R^{12}-$, $Y^2$ represents a cysteine, homocysteine or glutathione group whose terminal amino group is used for attachment.

In one embodiment of the present invention, the group Y may be selected from those listed below:
— $X^{11}-R^{12}-Y^1$;
— $X^{11}-R^{12}-X^{12}-CO-R^{13}-Y^1$;
— $X^{11}-R^{12}-CO-X^{13}-R^{13}-Y^1$;
— $X^{11}-R^{12}-X^{12}CO-X^{13}-R^{13}-Y^1$;
— $N(R^{11})N(R^{14})CO-R^{12}-Y^1$; and
— $N(R^{11})N(R^{14})CO-R^{12}-CON(R^{15})N(R^{16})CO-R^{13}-Y^1$ wherein $X^{11}$, $X^{12}$ and $X^{13}$ are each independently selected from O and $N(R^{11})$;

$Y^1$ is selected from an amino group, a mercapto group, a formyl group, a group containing a carbon-carbon double bond, and a group containing a carbon-carbon triple bond;

$R^{11}$; $R^{14}$; $R^{15}$ and $R^{16}$ are each independently selected from a hydrogen atom or a $C_{1-6}$ alkyl group; and $R^{12}$ and $R^{13}$ are each a divalent $C_{2-50}$ hydrocarbon group or a divalent $C_{2-50}$ polyalkyleneoxy group, wherein the divalent $C_{2-50}$ hydrocarbon group may partially contain a polyalkyleneoxy moiety by insertion of 1 to 10 oxygen atoms.

$Y^1$ is preferably selected from an amino group, a mercapto group, a formyl group, and a group containing a carbon-carbon double bond.

Examples preferred as the group Y include:
—$NH-(CH_2)_p-O-CO-C(R^{17})=CH_2$;
—$NH-(CH_2)_p-O-CO-CH(R^{17})-CH_2-S-CH_2-CH(OH)-CH(OH)-CH_2-SH$;
—$NH-(CH_2)_p-NH_2$;
—$NH-(CH_2)_p-SH$;
—$NH-(CH_2)_p-NH-CO-C(R^{17})=CH_2$;
—$NH-(CH_2)_p-NH-C(=NH)-(CH_2)_3-SH$;
—$NH-(CH_2)_p-NH-CO-(CH_2)_r-SH$;
—$NH-(CH_2)_p-NH-CO-CH(R^{17})-CH_2-S-CH_2-CH(OH)-CH(OH)-CH_2-SH$;
—$NH-(CH_2)_p-NH-CO-CH(NH_2)-CH_2-SH$;
—$NH-(CH_2)_p-NH-CO-CH(NH_2)-(CH_2)_2-SH$;
—$NH-NH-CO-(CH_2)_4-CO-NH-NH_2$;
—$NH-NH-CO-(CH_2)_4-CO-NH-NH-C(=NH)-(CH_2)_3-SH$;
—$NH-(CH_2-CH_2-O)_q-CH_2-CH_2-O-CO-C(R^{17})=CH_2$;
—$NH-(CH_2-CH_2-O)_q-CH_2-CH_2-O-CO-CH(R^{17})-CH_2-S-CH_2-CH(OH)-CH(OH)-CH_2-SH$;
—$NH-(CH_2-CH_2-O)_q-CH_2-CH_2-NH_2$;
—$NH-(CH_2-CH_2-O)_q-CH_2-CH_2-SH$;

—NH—(CH$_2$—CH$_2$—O)$_q$—CH$_2$—CH$_2$—NH—CO—C(R$^{17}$)=CH$_2$;
—NH—(CH$_2$—CH$_2$—O)$_q$—CH$_2$—CH$_2$—NH—C(=NH)—(CH$_2$)$_3$—SH;
—NH—(CH$_2$—CH$_2$—O)$_q$—CH$_2$—CH$_2$—NH—CO—(CH$_2$)$_r$—SH;
—NH—(CH$_2$—CH$_2$—O)$_q$—CH$_2$—CH$_2$—NH—CO—CH(R$^{17}$)—CH$_2$—S—CH$_2$—CH(OH)—CH(OH)—CH$_2$—SH;
—NH—(CH$_2$—CH$_2$—O)$_q$—CH$_2$—CH$_2$—NH—CO—CH(NH$_2$)—CH$_2$—SH;
—NH—(CH$_2$—CH$_2$—O)$_q$—CH$_2$—CH$_2$—NH—CO—CH(NH$_2$)—(CH$_2$)$_2$—SH;
—NH—CH(CO$_2$H)—(CH$_2$)—SH;
—NH—CH(CO$_2$H)—(CH$_2$)$_2$—SH; and
—NH—CH(CO$_2$H)—(CH$_2$)$_2$—CONH—CH(CONH—CH$_2$—CO$_2$H)—CH$_2$—SH wherein R$^{17}$ is a hydrogen atom or a C$_{1-6}$ alkyl group, p is an integer of 2 to 10, q is an integer of 1 to 200, and r is an integer of 1 to 3. Particularly preferred are:
—NH—CH$_2$—CH$_2$—O—CO—C(R$^{17}$)=CH$_2$;
—NH—NH—CO—(CH$_2$)$_4$—CO—NH—NH$_2$;
—NH—NH—CO—(CH$_2$)$_4$—CO—NH—NH—C(=NH)—(CH$_2$)$_3$—SH;
—NH—(CH$_2$—CH$_2$—O)$_2$—CH$_2$—CH$_2$—NH$_2$;
—NH—(CH$_2$—CH$_2$—O)$_2$—CH$_2$—CH$_2$—NH—C(=NH)—(CH$_2$)$_3$—SH;
—NH—(CH$_2$—CH$_2$—O)$_2$—CH$_2$—CH$_2$—NH—CO—CH$_2$—SH; and
—NH—CH$_2$—CH$_2$—O—CO—CH(R$^{17}$)—CH$_2$—S—CH$_2$—CH(OH)—CH(OH)—CH$_2$—SH wherein R$^{17}$ is a hydrogen atom or a C$_{1-6}$ alkyl group.

R$^{17}$ is preferably a hydrogen atom or a methyl group.

In a case where the hydrophilic polysaccharide derivative has carboxy groups (e.g., when the hydrophilic polysaccharide derivative is hyaluronic acid), one or more carboxy groups in the hydrophilic polysaccharide derivative may be converted into —CO—Y for introduction of the above crosslinkable group.

To introduce the above crosslinkable group, one or more hydroxy groups in the hydrophilic polysaccharide derivative or hyaluronic acid or a derivative thereof may be converted into —O—Z, wherein examples of the group Z include those listed below:
—CO—C(R$^{21}$)=CH$_2$;
—CH$_2$CH(OH)—R$^{22}$—Y$^1$;
—CH(CH$_2$OH)—R$^{22}$—Y$^1$;
—CONH—R$^{23}$—Y$^1$;
—CO—R$^{23}$—Y$^1$;
—CONH—CH$_2$CH$_2$—(X$^{21}$—CH$_2$CH$_2$)—Y$^1$; and
—CO—CH$_2$CH$_2$—(X$^{21}$—CH$_2$CH$_2$)$_n$—Y$^1$ wherein X$^{21}$ is selected from O and S;
n represents an integer of 1 to 50;
Y$^1$ is selected from an amino group, a mercapto group, a formyl group, a group containing a carbon-carbon double bond, and a group containing a carbon-carbon triple bond;
R$^{21}$ is selected from a hydrogen atom or a C$_{1-6}$ alkyl group; and
R$^{22}$ and R$^{23}$ are each a divalent C$_{2-50}$ hydrocarbon group or a divalent C$_{2-50}$ polyalkyleneoxy group, wherein the divalent C$_{2-50}$ hydrocarbon group may partially contain a polyalkyleneoxy moiety by insertion of 1 to 10 oxygen atoms.

In one embodiment of the present invention, the group Z may be selected from those listed below:
—CO—C(R$^{21}$)=CH$_2$;
—CH$_2$CH(OH)—R$^{22}$—Y$^1$;
—CH(CH$_2$OH)—R$^{22}$—Y$^1$;
—CONH—R$^{23}$—Y$^1$; and
—CO—R$^{23}$—Y$^1$ wherein Y$^1$ is selected from an amino group, a mercapto group, a formyl group, a group containing a carbon-carbon double bond, and a group containing a carbon-carbon triple bond;
R$^{21}$ is selected from a hydrogen atom or a C$_{1-6}$ alkyl group; and
R$^{22}$ and R$^{23}$ are each a divalent C$_{2-50}$ hydrocarbon group or a divalent C$_{2-50}$ polyalkyleneoxy group, wherein the divalent C$_{2-50}$ hydrocarbon group may partially contain a polyalkyleneoxy moiety by insertion of 1 to 10 oxygen atoms.

As used herein, the term "C$_{1-6}$ alkyl group" is intended to mean a linear or branched alkyl group containing 1 to 6 carbon atoms. Examples include "C$_{1-4}$ alkyl groups" such as methyl, ethyl, n-propyl, i-propyl, n-butyl, s-butyl, i-butyl and t-butyl, as well as n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, and 2-ethylbutyl.

As used herein, the term "C$_{8-50}$ hydrocarbon group" is not limited in any way and examples include linear, branched, cyclic and partially cyclic alkyl, alkenyl and alkynyl groups containing 8 to 50 carbon atoms. This group may be an aromatic ring group or may contain an aromatic ring in a part of its structure.

As used herein, the term "divalent C$_{1-50}$ hydrocarbon group" is not limited in any way and examples include linear, branched, cyclic and partially cyclic alkylene, alkenylene and alkynylene groups containing 1 to 50 carbon atoms. This group may be a divalent aromatic ring or may contain an aromatic ring in a part of its structure.

As used herein, the term "divalent C$_{2-50}$ hydrocarbon group" is not limited in any way and examples include linear, branched, cyclic and partially cyclic alkylene, alkenylene and alkynylene groups containing 2 to 50 carbon atoms. This group may be a divalent aromatic ring or may contain an aromatic ring in a part of its structure.

As used herein, the term "divalent C$_{2-10}$ hydrocarbon group" is not limited in any way and examples include linear, branched, cyclic and partially cyclic alkylene, alkenylene and alkynylene groups containing 2 to 10 carbon atoms. This group may be a divalent aromatic ring or may contain an aromatic ring in a part of its structure.

As used herein, the term "divalent C$_{2-50}$ polyalkyleneoxy group" is not limited in any way and the alkylene group as a repeated unit may be either linear or branched. Examples of such a "divalent C$_{2-50}$ polyalkyleneoxy group" include a divalent C$_{2-50}$ polyethyleneoxy group, a C$_{3-48}$ polypropyleneoxy group, a C$_{3-48}$ polybutyleneoxy group, etc. This group may be linked via an oxygen atom or a carbon atom to another group. By way of example, the C$_{2-50}$ polyethyleneoxy group includes —O(CH$_2$CH$_2$O)$_{1-25}$—, —(CH$_2$CH$_2$O)$_{1-25}$—, —(OCH$_2$CH$_2$)$_{1-25}$—, —(CH$_2$CH$_2$O)$_{1-24}$—(CH$_2$CH$_2$)—, etc.

As defined herein, when oxygen atoms are inserted into a hydrocarbon group, 1 or 2 oxygen atoms may be inserted at any positions of the hydrocarbon group, and 3 or more oxygen atoms may be inserted such that the hydrocarbon group partially contains a polyalkyleneoxy moiety.

As defined herein, when 1 to 10 oxygen atoms are inserted into a divalent C$_{2-50}$ hydrocarbon group, 1 or 2 oxygen atoms may be inserted at any positions of the hydrocarbon group, and 3 to 10 oxygen atoms may be inserted such that the hydrocarbon group partially contains a polyalkyleneoxy moiety. Examples of a polyalkyleneoxy moiety contained in the above group include $C_{2-20}$ ethyleneoxy, $C_{3-30}$ propyleneoxy, $C_{4-40}$ polybutyleneoxy, etc.

As used herein, the term "group containing a carbon-carbon double bond" is not limited in any way and examples of such a group include linear, branched, cyclic and partially cyclic $C_{2-50}$ alkenylene groups, $C_{2-30}$ alkenylene groups or $C_{2-10}$ alkenylene groups. Further examples of the above group containing a carbon-carbon double bond include a group of the following formula:

—$X^{14}$—CO—C($R^{18}$)=$CH_2$ wherein $X^{14}$ is selected from O and N($R^{19}$); $R^{18}$ is a hydrogen atom or a $C_{1-6}$ alkyl group; and $R^{19}$ is a hydrogen atom or a $C_{1-6}$ alkyl group as well as a group of the following formula:

[Formula 1]

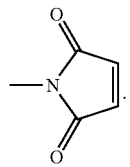

As used herein, the term "group containing a carbon-carbon triple bond" is not limited in any way and examples of such a group include linear, branched, cyclic and partially cyclic $C_{2-50}$ alkynylene groups, $C_{2-30}$ alkynylene groups or $C_{2-10}$ alkynylene groups.

The group Z is preferably —CO—C($R^{21}$)=$CH_2$, particularly preferably an acryloyl group or a methacryloyl group.

In the above aspect of the present invention, the hydrophilic polysaccharide derivative having a hydrophobic group(s) is not limited in any way and may be, for example, a hydrophilic polysaccharide obtained by introduction of 0.5 to 30 hydrophobic groups per 100 monosaccharides in the hydrophilic polysaccharide. In such a hydrophilic polysaccharide modified to have hydrophobic groups, several molecules will spontaneously associate in an aqueous solution upon hydrophobic interaction to form a nano-size (1 to 1,000 nm) particulate, whereby the hydrophilic polysaccharide is complexed with a hydrophobic drug or with a pharmacologically active protein or peptide.

The above hydrophilic polysaccharide derivative can be obtained by introduction of hydrophobic groups into a hydrophilic polysaccharide or a derivative thereof. The hydrophilic polysaccharide intended for this purpose includes water-soluble polysaccharides such as, but not limited to, pullulan, amylopectin, amylose, dextran, mannan, levan, inulin, chitin, chitosan, hyaluronic acid, dextrin and so on.

As used herein, the term "crosslinking" or "crosslinkage" may be either a chemical bond formed by covalent or other bonding or a physical bond (association) formed by hydrophobic or electrostatic interaction. This term means containing intermolecular or intramolecular crosslinkages, and may also mean having both intermolecular and intramolecular crosslinkages. As used herein, the term "crosslinking group" is intended to mean a group that forms the above crosslinkage. As used herein, the term "crosslinkable group" is intended to mean a group that can form a crosslinking group through crosslinkage formation reaction or under certain conditions.

In the above aspect of the present invention, the above hydrophobic group is not limited in any way and may be, for example, a group containing a $C_{8-50}$ hydrocarbon group or a steryl group.

To introduce the above hydrophobic group, for example, one or more hydroxy groups in the above hydrophilic polysaccharide or a derivative thereof may be converted into —OX, wherein examples of X include the groups listed below:
—CO—$R^1$;
—CO—$X^1$—$R^2$;
—CO—$R^3$—$X^2$—CO—$R^1$;
—CO—$X^1$—$R^3$—CO—$R^1$;
—CO—$R^3$—CO—$X^3$—$R^2$;
—CO—$X^1$—$R^3$—CO—$X^3$—$R^2$;
—CO—$X^1$—$R^3$—$X^2$—CO—$R^1$;
—CO—$R^3$—$X^2$—CO—$X^3$—$R^2$; and
—CO—$X^1$—$R^3$—$X^2$—CO—$X^3$—$R^2$ wherein $R^1$ is a $C_{8-50}$ hydrocarbon group;
$R^2$ is a $C_{8-50}$ hydrocarbon group or a steryl group;
$R^3$ is a divalent $C_{2-50}$ hydrocarbon group;
$X^1$, $X^2$ and $X^3$ are each independently selected from O and N($R^4$); and
$R^4$ is a hydrogen atom or a $C_{1-6}$ alkyl group.

In one embodiment of the present invention, X may be a group selected from those listed below:
—CO—$R^1$;
—CO—$X^1$—$R^2$;
—CO—$R^3$—$X^2$—CO—$R^1$;
—CO—$X^1$—$R^3$—CO—$R^1$;
—CO—$X^1$—$R^3$—CO—$X^3$—$R^2$;
—CO—$X^1$—$R^3$—$X^2$—CO—$R^1$;
—CO—$R^3$—$X^2$—CO—$X^3$—$R^2$; and
—CO—$X^1$—$R^3$—$X^2$—CO—$X^3$—$R^2$ wherein $R^1$ is a $C_{8-50}$ hydrocarbon group;
$R^2$ is a $C_{8-50}$ hydrocarbon group or a steryl group;
$R^3$ is a divalent $C_{2-50}$ hydrocarbon group;
$X^1$, $X^2$ and $X^3$ are each independently selected from O and N($R^4$); and
$R^4$ is a hydrogen atom or a $C_{1-6}$ alkyl group.

X is preferably —CO—$R^3$—CO—$X^3$—$R^2$ or —CO—$X^1$—$R^3$—$X^2$—CO—$X^3$—$R^2$, more preferably —CO—$R^3$—CO—O—$R^2$ or —CO—NH—$R^3$—NH—CO—O—$R^2$, and even more preferably —CO—NH—$R^3$—NH—CO—O—$R^2$.

Examples of $R^3$ include a linear or branched $C_{2-50}$ alkylene group, a linear or branched $C_{2-50}$ alkenylene group, and a linear or branched $C_{2-50}$ alkynylene group, with a linear $C_{2-50}$ alkylene group being preferred. The number of carbon atoms contained in $R^3$ is preferably 2 to 20, 2 to 10, more preferably 2 to 6 for —CO—$R^3$—CO—$X^3$—$R^2$ and preferably 2 to 20, 2 to 10, more preferably 4 to 8 for —CO—$X^1$—$R^3$—$X^2$—CO—$X^3$—$R^2$.

Examples of a $C_{8-50}$ hydrocarbon group include a linear or branched $C_{8-50}$ alkyl group, a linear or branched $C_{8-50}$ alkenyl group, and a linear or branched $C_{8-50}$ alkynyl group, with a linear $C_{8-50}$ alkyl group being preferred. The number of carbon atoms contained in these groups is preferably 10 to 30, more preferably 10 to 20, and examples include a lauryl group, a myristyl group, a cetyl group, and a stearyl group.

The steryl group is not limited in any way as long as it is a group having a sterol skeleton. Examples include a cholesteryl group, a stigmasteryl group, a β-sitosteryl group, a lanosteryl group, and an ergosteryl group, with a cholesteryl group being preferred.

$R^2$ is preferably a cholesteryl group, —$(CH_2)_{11}CH_3$, —$(CH_2)_{15}CH_3$ or —$(CH_2)_{19}CH_3$, more preferably a cholesteryl group.

Specific examples preferred as X are:
—CO—$(CH_2)_r$—CO—O-cholesteryl;
—CO—$(CH_2)_r$—CO—O—$(CH_2)_{11}CH_3$;

—CO—(CH$_2$)$_t$—CO—O—(CH$_2$)$_{15}$CH$_3$;
—CO—(CH$_2$)$_t$—CO—O—(CH$_2$)$_{19}$CH$_3$;
—CO—NH—(CH$_2$)$_u$—NH—CO—O-cholesteryl;
—CO—NH—(CH$_2$)$_u$—NH—CO—O—(CH$_2$)$_{11}$CH$_3$;
—CO—NH—(CH$_2$)$_u$—NH—CO—O—(CH$_2$)$_{15}$CH$_3$;
and
—CO—NH—(CH$_2$)$_u$—NH—CO—O—(CH$_2$)$_{19}$CH$_3$ wherein t is an integer of 2 to 6, and u is an integer of 4 to 8, and particularly preferred is —CO—NH—(CH$_2$)$_6$—NH—CO—O-cholesteryl.

To introduce the above hydrophobic group, for example, one or more carboxy groups in the above hydrophilic polysaccharide or a derivative thereof may be converted into —CO—OX.

In one embodiment of the above aspect of the present invention, the above crosslinkage formation reaction is accomplished by adding a crosslinking agent to the above solution.

In one embodiment of the above aspect of the present invention, a hydrophilic polysaccharide derivative having no crosslinking group may be encapsulated by the hyaluronic acid derivative having a crosslinking group(s). Moreover, in one embodiment of the above aspect of the present invention, the hydrophilic polysaccharide derivative may have an intramolecular crosslinking group or may have an intermolecular crosslinking group that is linked to the hydrophilic polysaccharide derivative and the hyaluronic acid derivative. Further, in one embodiment of the above aspect of the present invention, the hydrophilic polysaccharide derivative may have a crosslinking group that is linked to only the hyaluronic acid derivative.

In one embodiment, the composition provided by the above aspect of the present invention is used as a pharmaceutical composition. This pharmaceutical composition may contain any drug, for example, may contain a protein or peptide as a drug.

In a further aspect, the present invention provides a process for preparing a pharmaceutical composition, which comprises the step of adding a drug solution to the gel provided by the above aspect of the present invention to thereby ensure drug absorption into the gel.

In yet another aspect, the present invention provides a process for preparing a gel-form composition, which comprises the following steps:
(a) preparing a hyaluronic acid derivative having a crosslinkable group(s);
(b) preparing a hydrophilic polysaccharide derivative having a hydrophobic group(s); and
(c) forming a hybrid gel of at least two or more polymers selected from at least one or more polymers prepared in step (a) and at least one or more polymers prepared in step (b). Hybrid gel formation in step (c) may be accomplished by using any generally known method which allows crosslinking of polymers. Without being limited thereto, the hyaluronic acid derivative having a crosslinkable group(s) and the hydrophilic polysaccharide derivative having a hydrophobic group(s) may be crosslinked using a crosslinking agent, or the hyaluronic acid derivative having a crosslinkable group(s) may be crosslinked in the presence of the above hydrophilic polysaccharide derivative, or the hyaluronic acid derivative having a crosslinkable group(s) may be crosslinked with the above hydrophilic polysaccharide derivative which is further modified to have a crosslinkable group(s). This step may be performed in bulk or in a discontinuous phase such as a W/O emulsion or spray droplets. During this step, the crosslinking reaction may be stopped. Step (c) may be followed by steps of grinding, drying and washing, etc.

In yet another aspect, the present invention provides a process for preparing a pharmaceutical composition, which comprises the step of adding a drug solution to the above gel to thereby ensure drug encapsulation into the gel, and a pharmaceutical composition obtainable by this process. This step may be followed by steps of grinding, drying and washing, etc.

In yet another aspect, the present invention provides a process for preparing a pharmaceutical composition, which comprises the following steps:
(a) complexing a drug with a nanogel composed of HP or a derivative thereof; and
(b) forming a hybrid gel between the nanogel/drug complex obtained in step (a) and HA or a derivative thereof, and a pharmaceutical composition obtainable by this process.
If necessary, step (b) may be followed by steps of grinding, drying and washing, etc.

Advantages Of The Invention

The gel of the present invention enables the provision of practical sustained-release formulations free from any problem of safety that allow efficient encapsulation and long-term sustained release of drugs, particularly pharmacologically active proteins or peptides, while retaining their biological activity, which could not be achieved by conventional sustained-release formulations.

PREFERRED EMBODIMENTS OF THE INVENTION

Figure 1:
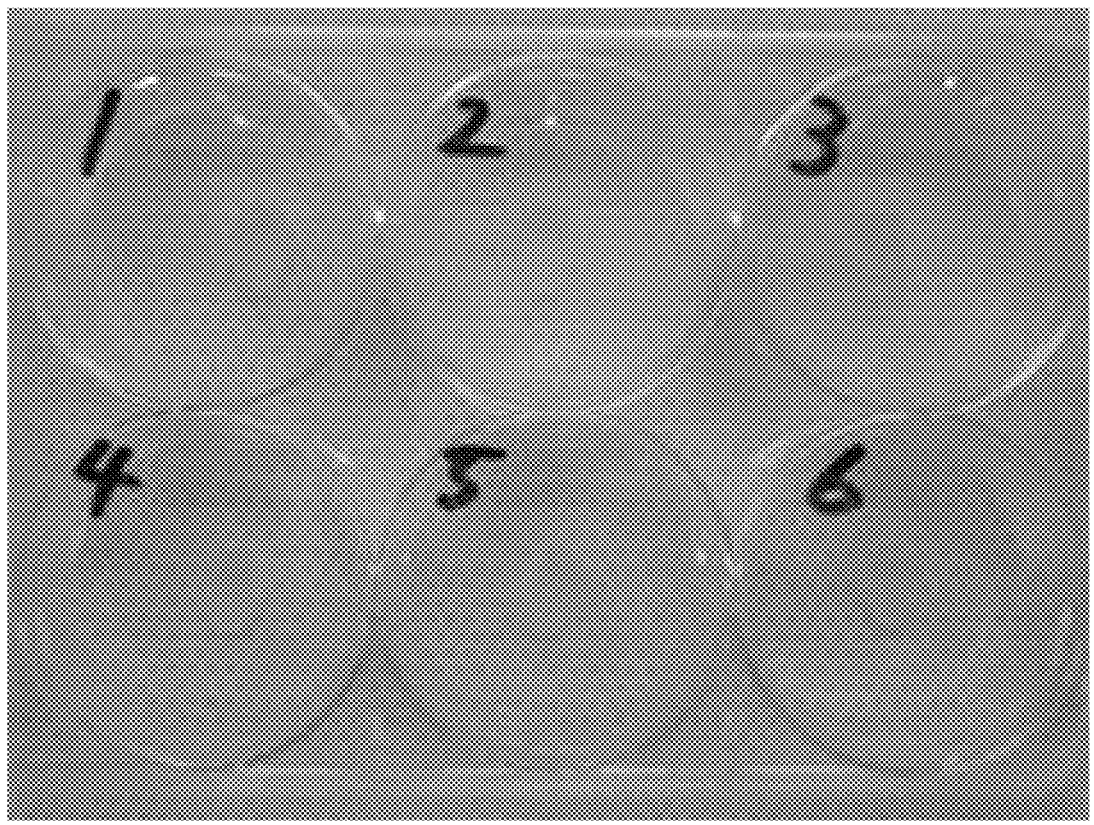
FIG. 1 is one example of a photograph showing CHP-encapsulating chemically crosslinked HA-MA hybrid gels after FITC-Ins absorption.

The present invention will be further described in more detail below.

The composition (preferably gel-form composition) of the present invention is characterized by comprising a hyaluronic acid derivative having a crosslinking group(s) and a hydrophilic polysaccharide derivative having a hydrophobic group(s), and it also has the following excellent characteristics as a sustained-release drug carrier.

1. The composition is biodegradable and is safe in vivo.
2. It is possible to prevent denaturation of drugs, particularly pharmacologically active proteins or peptides, during encapsulation and formulation steps and in the body.
3. It is possible to control the sustained release period by controlling the crosslinking density and degradability of the composition.

Hyaluronic acid derivatives used in the present invention are those having substituents attached to at least one or more carboxy or hydroxy (OH) groups in hyaluronic acid. These substituents may be of one or more types. Preparation may be accomplished in various known manners. Non-limiting examples of a crosslinking functional group include an amino group (AM), a mercapto group (SH), an unsaturated bond-containing group, and a formyl group (ALD), the preparation of which is disclosed in, for example, Patent Document 5, Patent Document 9 and Non-patent Document 11. Such a substituent may be attached via a spacer. Further modifications may be made to control the rate of biodegradation, the preparation of which is disclosed in, for example, Patent Document 9.

Although there is no particular limitation on the molecular weight of hyaluronic acid and a derivative thereof used in the present invention, a lower molecular weight results in a lower efficiency of crosslinking reaction during gelling, while a higher molecular weight makes it more difficult to ensure homogeneous mixing with HP or a derivative thereof or with a crosslinking agent due to increased solution viscosity. For this reason, the molecular weight is preferably 1 kDa to 1,000 kDa, and more preferably 10 kDa to 300 kDa.

The hyaluronic acid derivative used in the present invention may be in the form of a pharmaceutically acceptable salt. Examples of a pharmaceutically acceptable salt include alkali metal salts such as a sodium salt, a potassium salt and a lithium salt, and particularly preferred is a sodium salt which is widely used for pharmaceutical purposes. Hyaluronic acid or a pharmaceutically acceptable salt thereof may be prepared in various known manners, for example, by extraction from a biological material such as cock's comb or swine hypodermis or by biological fermentation. Alternatively, a commercially available product may be purchased (e.g., from Shiseido Co., Ltd., Japan, Denki Kagaku Kogyo Kabushiki Kaisha, Japan, Seikagaku Corporation, Japan or others) and obtained for this purpose.

Hydrophilic polysaccharide derivatives having a hydrophobic group(s) used in the present invention are those obtainable by introducing at least one or more hydrophobic groups per molecule of a hydrophilic polysaccharide or a derivative thereof. Such a hydrophilic polysaccharide is not limited in any way, and preferred are pullulan, amylopectin, amylose, dextran, mannan, levan, inulin, chitin, chitosan, hyaluronic acid, and dextrin, which are commercially available or may be prepared to have various average molecular weights according to the reported processes. Particularly preferred for use as hydrophilic polysaccharides are pullulan, hyaluronic acid, and dextrin. A preferred dextrin is Cluster Dextrin®. Cluster Dextrin® can be purchased from Ezaki Glico Co., Ltd., Japan and used for this purpose. Hydrophobic groups are not limited in any way, and preferred are groups such as a $C_{8-50}$ hydrocarbon group, a steryl group, a polylactic acid (PLA) group and a polylactic acid-glycolic acid copolymer (PLGA) group, or groups containing these groups. Particularly preferred is a group containing a cholesteryl group, a linear or branched $C_{8-30}$ alkyl group or a group containing the same. Such a hydrophobic group may be introduced via a spacer.

Such a hydrophilic polysaccharide derivative having a hydrophobic group(s) can be prepared in various known manners. For example, in the case of a hydrophilic polysaccharide derivative modified to have N-[6-(cholesteryloxycarbonylamino)hexyl]-carbamoyl groups which are introduced as hydrophobic groups into hydroxy groups in pullulan as a hydrophilic polysaccharide (the derivative thus obtained is hereinafter also referred to as "cholesterol pullulan" or "CHP"), procedures for its preparation are disclosed in Patent Document 10, or alternatively, a commercially available product may be purchased (e.g., from NOF Corporation, Japan) and obtained. In such a hydrophilic polysaccharide derivative having a hydrophobic group(s), several molecules will spontaneously associate in an aqueous solution upon hydrophobic interaction to form a nano-size (1 to 1,000 nm) particulate having a gel structure (hereinafter also referred to as "nanogel"), whereby the derivative can be complexed with a hydrophobic drug or with a pharmacologically active protein or peptide. Examples include those illustrated in Non-patent Document 4, Non-patent Document 5, Non-patent Document 6, and Non-patent Document 7. The introduction rate of hydrophobic groups is not limited in any way, but it is preferably within a range that ensures stable nanogel formation, stable drug complexation, and a higher amount of drug complexation. This range will vary depending on a combination between hydrophilic polysaccharide and hydrophobic group. For example, in the case of using pullulan as a hydrophilic polysaccharide, it is preferably substituted with 1 to 5 N-[6-(cholesteryloxycarbonylamino)hexyl]carbamoyl groups per 100 monosaccharides.

Such a hydrophilic polysaccharide derivative having a hydrophobic group(s) has at least one or more hydrophobic groups attached per molecule, and may also be modified by introduction of additional substituents. Hydrophobic groups and substituents in the above hydrophilic polysaccharide derivative may be of one or more types. Preparation may be accomplished in various known manners. Without being limited thereto, the hydrophilic polysaccharide derivative may also be modified to have a crosslinkable group(s) as a substituent(s). Examples of a crosslinkable group include a group selected from an amino group, a mercapto group, a group having an unsaturated bond (e.g., carbon-carbon double bond, carbon-carbon triple bond) and a formyl group, as well as groups containing these groups. For example, in the case of a hydrophilic polysaccharide derivative having methacryloyl groups introduced into CHP, procedures for its preparation are disclosed in Patent Document 8. Such a substituent may contain a spacer moiety.

Although there is no particular limitation on the molecular weight of the hydrophilic polysaccharide derivative having a hydrophobic group(s) used in the present invention, it is preferably 1 kDa to 1,000 kDa, and more preferably 10 kDa to 300 kDa. Moreover, the above hydrophilic polysaccharide derivative may be in the form of a pharmaceutically acceptable salt.

The composition (preferably gel-form composition) of the present invention is a hybrid gel obtained by crosslinking at least two or more polymers selected from hyaluronic acid derivatives having a crosslinkable group(s) and hydrophilic polysaccharide derivatives having a hydrophobic group(s). The ratio of polymers may be selected as appropriate by practicians. Since the hydrophilic polysaccharide derivative having a hydrophobic group(s) has the function of being complexed with and stably holding a pharmacologically active protein or peptide or a hydrophobic low-molecular-weight drug, a higher ratio of this derivative in the composition allows a larger amount of drug to be encapsulated into the hybrid gel.

To ensure stable holding of a drug such as a protein, the hydrophilic polysaccharide derivative having a hydrophobic group(s) preferably holds the drug within particulates formed in an aqueous solution upon association of these hydrophobic groups, and is thereby complexed with the drug and the above hybrid gel. In another case, multiple hydrophobic groups in the hydrophilic polysaccharide derivative having a hydrophobic group(s) may associate at multiple sites in an aqueous solution without forming any particulate, so that a drug is held at one or more of these associated sites. In particular, when the hydrophilic polysaccharide derivative having a hydrophobic group(s) has a higher concentration in an aqueous solution, the aqueous solution is more likely to be gelled in bulk and hence a drug is more likely to be held in the latter form.

The composition (preferably gel-form composition) of the present invention may be a hybrid gel having a compositive crosslinked structure. The term "crosslinked" may be either a chemical bond formed by covalent bonding or a physical bond formed by hydrophobic or electrostatic interaction. This term means containing intermolecular or intramolecular crosslinkages, and may also mean having both intermolecular and intramolecular crosslinkages. This hybrid gel is characterized by having not only at least one or more chemically crosslinked structures formed by chemical bonding, but also one or more physically crosslinked structures formed by hydrophobic interaction.

The present invention also relates to the step of forming a hybrid gel of at least two or more polymers selected from hyaluronic acid derivatives having a crosslinkable group(s) and hydrophilic polysaccharide derivatives having a hydrophobic group(s). The hybrid gel of the present invention may be formed by various known crosslinking techniques.

Although there is no particular limitation on the process for preparing the composition of the present invention, for example, a hyaluronic acid derivative having a crosslinkable group(s) may be crosslinked in the presence of a hydrophilic polysaccharide derivative having a hydrophobic group(s). More specifically, a hyaluronic acid derivative modified to have amino groups (HA-AM) may be crosslinked by condensation reaction with a crosslinking agent having succinimidyl esters or other imidoesters at the both ends of a $C_{2-20}$ alkylene group (e.g., bis[sulfosuccinimidyl]suberate ($BS_3$), ethylene glycol-bis[sulfosuccinimidyl]succinate (Sulfo-EGS), dimethyl adipimidate hydrochloride (DMA)). Alternatively, HA-AM may be crosslinked with a crosslinking agent having formyl groups at the both ends of a $C_{2-20}$ alkylene group (e.g., glutaraldehyde). Alternatively, a hyaluronic acid derivative modified to have formyl groups (HA-ALD) may be crosslinked with a crosslinking agent having amino groups at the both ends of a $C_{2-20}$ alkylene group (e.g., ethylenediamine (EDA)). Further, a hyaluronic acid derivative modified to have mercapto groups (HA-SH) may be crosslinked by oxidation reaction under oxidation conditions (e.g., in the presence of sodium tetrathionate (STT)). Further, HA-SH may be crosslinked by Michael addition reaction with a crosslinking agent having unsaturated bonds (e.g., maleimido (MAL) groups or methacryloyl groups) at the both ends of a $C_{2-20}$ alkylene group (e.g., 1,4-bis-maleimidobutane (BMB), ethylene dimethacrylate (EDMA)). Further, a hyaluronic acid derivative modified to have unsaturated bond-containing functional groups (e.g., methacryloyl groups (hereinafter also referred to as "MA groups"), acryloyl groups) introduced into hyaluronic acid may be crosslinked by Michael addition reaction with a crosslinking agent having SH groups at the both ends of a $C_{2-20}$ alkylene group (e.g., dithiothreitol (DTT)). Further, the above hyaluronic acid derivative modified to have unsaturated bonds may be crosslinked by radical polymerization with various polymerization initiators (e.g., potassium peroxodisulfate (KPS)/N,N,N',N'-tetramethylethylenediamine (TEMED), Irgacure2959). Further, in the presence of and a diamine compound (e.g., EDA, 2,2'-(ethylenedioxy)bis(ethylenediamine)), sodium hyaluronate may be crosslinked by the action of a condensing agent (e.g., N,N'-carbonyldiimidazole (CDI), N,N'-dicyclohexylcarbodiimide (DCC), N-ethoxycarbonyl-2-ethoxy-1,2-dihydroquinoline (EEDQ), 4-(4,6-dimethoxy-1,3,5-triazine)-4-methylmorpholium chloride (DMT-MM), 2-benzotriazole-1,1,3,3-tetramethyluronium tetrafluoroborate (TBTU), 3,4-dihydro-3-hydroxy-4-oxo-1,2,3-benzotriazine (HODhbt), benzotriazole-1-oxy-tris-pyrrolidino-phosphonium hexafluorophosphate (PyBOP), benzotriazol-1-yl-oxy-tris(dimethylamino)phosphonium hexafluorophosphate (BOP), 1-ethyl-3-(3-dimethylaminopropyl)carbodiimide (EDC) or N-hydroxysuccinimide (NHS)). The above crosslinkage formation may occur in the same molecule of the hyaluronic acid derivative or may occur between different molecules of the hyaluronic acid derivative.

Alternatively, although there is no particular limitation on the process for preparing the composition of the present invention, for example, two types of hyaluronic acid derivatives modified to have different crosslinking functional groups may be chemically crosslinked to each other in the presence of a hydrophilic polysaccharide derivative having a hydrophobic group(s). More specifically, HA-AM and a HA derivative modified to have active ester groups may be crosslinked by condensation reaction. Alternatively, HA-AM and HA-ALD may be crosslinked. Further, HA-SH and HA-MA may be crosslinked by Michael addition reaction.

Moreover, for example, hydroxy groups contained in hyaluronic acid or a derivative thereof and a hydrophilic polysaccharide derivative having a hydrophobic group(s) can also be used as crosslinkable groups. Namely, hyaluronic acid or a derivative thereof and a hydrophilic polysaccharide derivative having a hydrophobic group(s) may be crosslinked with a specific crosslinking agent, such as divinylsulfone (DVS), carbodiimide, or a crosslinking agent having glycidyl ether groups at the both ends of a $C_{2-20}$ alkylene group.

Further, although there is no particular limitation on the process for preparing the composition of the present invention, for example, a hydrophilic polysaccharide derivative having a hydrophobic group(s) which is further modified to have a crosslinkable group(s) and a hyaluronic acid derivative which is modified to have a crosslinkable group(s) may be crosslinked. More specifically, the above hydrophilic polysaccharide derivative modified to have amino groups (HP-AM) and HA-AM may be crosslinked with a crosslinking agent as mentioned above, etc. Alternatively, a hydrophilic polysaccharide derivative having a hydrophobic group(s) which is further modified to have formyl groups (HP-ALD) and HA-ALD may be crosslinked with a crosslinking agent as mentioned above, etc. Further, a hydrophilic polysaccharide derivative having a hydrophobic group(s) which is further modified to have mercapto groups (HP-SH) and HA-SH may be crosslinked as described above. Further, a hydrophilic polysaccharide derivative having a hydrophobic group(s) which is further modified to have unsaturated bond-containing functional groups (e.g., methacryloyl groups, acryloyl groups) and a hyaluronic acid derivative which is modified to have unsaturated bond-containing functional groups may be crosslinked as described above. The above crosslinkage formation may occur in the same molecule of the hyaluronic acid derivative or hydrophilic polysaccharide derivative or may occur between different molecules of the hyaluronic acid derivative or hydrophilic polysaccharide derivative.

Further, although there is no particular limitation on the process for preparing the composition of the present invention, for example, a hydrophilic polysaccharide derivative having a hydrophobic group(s) and a hyaluronic acid derivative, each of which is modified to have different crosslinkable groups, may be chemically crosslinked. More specifically, HP-AM and a hyaluronic acid derivative modified to have active ester groups may be crosslinked by condensation reaction. Alternatively, HP-AM and HA-ALD, or HP-ALD and HA-AM may be crosslinked. Further, HP-MA and HP-SH, or HP-SH and HA-MA may be crosslinked by Michael addition reaction.

In the chemically crosslinked structure of the composition (preferably gel-form composition) of the present invention, biodegradable elements may be used for crosslinking agents, crosslinkable groups introduced into polymers, binding mode, and so on. Without being limited thereto, it is possible to use HA-MA or HP-MA which is modified to have methacryloyl or other groups having an ester bond as a substituent, by way of example. Alternatively, it is also possible to use a crosslinking agent having an ester bond in the spacer region, as exemplified by Sulfo-EGS or EDMA. It is also possible to use a peptide spacer which is degraded by an enzyme in the body. Moreover, a gel crosslinked via disulfide bonds formed by oxidation of mercapto groups will be degraded in the body by disulfide exchange reaction or reduction reaction. Having a degradable chemically crosslinked structure enables control of the biodegradation rate of a hybrid gel, which in turn also enables control of the drug release rate.

In the hybrid gel formation step of the present invention, conditions may be selected as appropriate. Conditions for crosslinking include, for example, two or more polymers selected from hyaluronic acid derivatives and hydrophilic polysaccharide derivatives having a hydrophobic group(s), a method for their crosslinking, polymer concentration, polymer ratio, crosslinking agent concentration, the type of solvent, solvent pH, salt concentration, temperature, time and so on.

In the preparation of the gel of the present invention, among reaction conditions for crosslinkage formation, for example, the polymer concentration and the introduction rate of crosslinkable groups during chemical crosslinking can be elevated to thereby increase the crosslinking density of the resulting hybrid gel.

The polymer concentration in the hybrid gel formation step of the present invention may be selected as appropriate within a range suitable for homogeneous mixing of polymers and a crosslinking agent before hybrid gel formation. This range will vary depending on the molecular weight of polymers, the type of substituent, the type of solvent selected, etc. For example, when a hyaluronic acid derivative of 20 kDa is used in water, the polymer concentration is preferably 1% w/v to 30% w/v, and particularly preferably 4% w/v to 20% w/v. When 200 kDa HA is used in water, the polymer concentration is preferably 0.1% w/v to 10% w/v, and particularly preferably 0.5% w/v to 4% w/v. Likewise, when CHP having 1.4 cholesterol groups per 100 monosaccharides in 100 kDa pullulan is used as HP in water, the polymer concentration is preferably 0.1% w/v to 4.0% w/v, and particularly preferably 0.5% w/v to 3.0% w/v. Moreover, when CHcDex having 3.8 cholesterol groups per 100 monosaccharides in 150 kDa Cluster Dextrin® is used as HP in water, the polymer concentration is preferably 0.1% w/v to 10.0% w/v, and particularly preferably 0.5% w/v to 8.0% w/v.

As to the crosslinking agent concentration in the hybrid gel formation step of the present invention, when using a crosslinking agent having crosslinkable groups at the both ends, it is preferably added at a concentration which allows these groups to rapidly contribute to crosslinking reaction without being either too much or too little. For example, when a polymer modified to have methacryloyl groups is crosslinked using DTT by Michael addition reaction, the MA group:SH group ratio is preferably 3:1 to 1:3, and particularly preferably 2:1 to 1:2.

A preferred solvent selected in the hybrid gel formation step of the present invention is one that can sufficiently dissolve polymers and a crosslinking agent. Without being limited thereto, water, dimethyl sulfoxide (DMSO), dimethylacetamide (DMAc), dimethylformamide (DMF), N-methylpyrrolidone (NMP), and mixed solvents selected therefrom are preferred for use. Alternatively, an organic solvent miscible to these solvents may also be mixed and used. Non-limiting examples of a miscible organic solvent include methanol, ethanol, propanol, isopropanol, butanol, acetone, acetonitrile, etc. It should be noted that water alone is preferred for use as a solvent, considering that particulates are formed in advance by association of hydrophobic groups in the hydrophilic polysaccharide derivative having a hydrophobic group(s).

Other conditions in the hybrid gel formation step of the present invention, i.e., solvent pH, salt concentration, time, temperature and so on are preferably set to conditions under which the selected crosslinking method rapidly proceeds and the selected polymers are chemically stable. Without being limited thereto, the salt concentration is preferably set to a lower value because higher salt concentrations may cause a reduction in the polymer solubility or phase separation between different types of polymers (see Examples 3 and 4).

The hybrid gel formation step of the present invention may be performed in bulk or in a discontinuous phase (e.g., in an emulsion or in spray droplets). For example, when this step is performed in a W/O emulsion, an aqueous phase in which polymers and a crosslinking agent are dissolved may be emulsified in a water-immiscible solvent and provided for gelling reaction. Non-limiting examples of a water-immiscible solvent include hexane, chloroform, dichloromethane, ethyl acetate, medium-chain fatty acid triglyceride (MCT), liquid paraffin, soybean oil, etc. A surfactant may also be added for stable emulsification. Moreover, for example, emulsification may be performed in a solvent capable of being removed, such as supercritical carbon dioxide or PEG. In this case, once an aqueous or organic phase in which polymers and a crosslinking agent are dissolved is emulsified and dispersed in the above solvent, the polymers can be concentrated as a result of desolvation (solvent diffusion) to thereby obtain a hybrid gel with a higher crosslinking density. An example based on this technique is disclosed in, for example, Patent Document 11, in which an aqueous solution of Dex-GMA having glycidyl methacrylate (GMA) introduced into dextran (Dex) is crosslinked in an aqueous solution of PEG simultaneously with dehydration. Emulsification may be accomplished, for example, by using a mechanical stirrer, a rotary homogenizer, membrane emulsification, ultrasonic irradiation or the like. When this step is performed in spray droplets, for example, a spray dryer may be used for gelling. In this technique, as disclosed in Patent Document 12, a solution in which polymers and a crosslinking agent are dissolved may be spray-dried to achieve concentration, gelling, drying and microparticle formation at the same time.

During or after the hybrid gel formation step of the present invention, additional operations may be performed to stop the crosslinking reaction and to inactivate or wash off residual crosslinking functional groups. Crosslinking functional groups which are not used for the reaction, groups which are attached to only one end of crosslinking agent molecules, residual crosslinking agent molecules and so on are preferably removed in terms of safety, storage stability, side reactions with a drug to be encapsulated, etc. Without being limited thereto, for example, when there remain unreacted crosslinking agent molecules, they may be removed by washing with an excessive amount of water. Likewise, for example, when there remain methacryloyl groups substituted onto polymers, an excessive amount of mercaptoethanol or the like may be added to inactivate the methacryloyl groups, followed by washing with an excessive amount of water to remove the excess of mercaptoethanol. Moreover, for example, when there remain mercapto groups, an excessive amount of maleimidopropionic acid, iodoacetic acid or the like may be added to inactivate the mercapto groups, followed by washing with an excessive amount of water to remove the excess of maleimidopropionic acid or iodoacetic acid.

The hybrid gel formation step of the present invention may be followed by a grinding step. Grinding techniques include grinding with a pestle and a mortar, grinding in a mill, and so on. Preferred is grinding in a mill. Examples of a mill grinder include rotating disk grinders such as a centrifugal mill (Nihonseiki Kaisha Ltd., Japan) and an impact mill (Dalton Co., Ltd., Japan), screen mill grinders such as an atomizer (Tokyo Atomizer Mfg. Co., Ltd., Japan), a sample mill (Tokyo Atomizer Mfg. Co., Ltd., Japan), a bantam mill (Tokyo Atomizer Mfg. Co., Ltd., Japan) and an SK mill (Tokken Inc., Japan), jet mills such as an ultra-micro labo jet mill (A-O jet mill, Seishin Enterprise Co., Ltd., Japan), as well as a Linrex mill (Liquid Gas Co., Ltd., Japan) which allows grinding at ultra-low temperatures, with a SK mill and a Linrex mill being preferred.

The hybrid gel formation step of the present invention may be followed by a drying step. Drying techniques include, for example, drying under ventilation, drying in a thermostatic vessel, drying under reduced pressure, and circulating hot air drying. Conditions such as air speed, drying period, temperature and pressure may be selected as appropriate within a range which causes no degradation or deterioration in the gel of the present invention.

The present invention also relates to a process for preparing a pharmaceutical composition by encapsulating a drug into the above hybrid gel of the present invention.

Techniques for drug encapsulation include those in which a drug solution is added to a pre-crosslinked hybrid gel. In this technique, a drug is absorbed by diffusion into the inside of a swollen gel, and the absorbed drug is then held in physically crosslinked domains formed by hydrophobic interaction in the hybrid gel to thereby achieve drug encapsulation. Without being limited thereto, conditions such as the type of solvent, salt concentration, pH, temperature, time, and addition of a denaturant may be selected as appropriate such that a drug is encapsulated stably and in high yields. For example, the salt concentration and pH during drug encapsulation will influence not only the swelling ratio and density of a hybrid gel, but also the ionized state of a drug, etc. For this reason, suitable conditions may be used as appropriate for each combination between hybrid gel and drug. On the other hand, as to complexation behavior between CHP nanogel and various proteins, for example, insulin (see Non-patent Document 12) or albumin (see Non-patent Document 7) will be spontaneously complexed at normal temperature, whereas carbonic anhydrase B (see Non-patent Document 8) or citrate synthase (see Non-patent Document 9) will be complexed upon thermal denaturation or under denaturing conditions (i.e., in the presence of a denaturant). In this way, conditions which allow complexation with a hydrophilic polysaccharide derivative having a hydrophobic group(s) will vary depending on the type of protein or peptide. For this reason, conditions for drug encapsulation into the composition (preferably gel-form composition) of the present invention may be adjusted as appropriate for the properties of a drug to be encapsulated, e.g., by optimizing the temperature or by adding a denaturant. In the case of adding a denaturant, drug encapsulation may be followed by washing with an excessive amount of water or the like to remove the excess of the denaturant. Moreover, in the above technique, when the hybrid gel of the present invention has a smaller size, its specific surface area is larger and a shorter distance is required for a drug to diffuse into the gel of the present invention before being held in hydrophobically crosslinked domains. Thus, the time required for the drug encapsulation step can be reduced. The crosslinking density of the hybrid gel of the present invention is preferably within a range where a drug to be encapsulated is rapidly absorbed by diffusion, and a hybrid gel having a suitable crosslinking density may be prepared as appropriate for, e.g., the molecular weight and/or size of a drug to be encapsulated, depending on the crosslinking method or conditions for hybrid gel formation. In the case of in situ crosslinking, unreacted crosslinking functional groups and crosslinking agent molecules still remain in the final formulations, which is not preferred in terms of safety for pharmaceutical purposes. Although this can be improved by a washing step or by a step of eliminating residual unreacted crosslinking functional groups with other reactive reagents, these steps should be performed in the presence of the encapsulated drug, thus leading to a reduced recovery rate and drug denaturation. In contrast, the above technique has a great advantage in that a washing step or the like can be performed in the absence of a drug prior to drug encapsulation. Moreover, since a drug that is not held in the hydrophobic domains in the hydrophilic polysaccharide derivative having a hydrophobic group(s) is rapidly released from the hybrid gel of the present invention when administered in vivo, such a drug is preferably removed by a washing step. If necessary, drug encapsulation may be followed by steps of grinding, drying, etc. Conditions for the grinding step or air speed, drying period, temperature, pressure and other conditions in the drying step may be selected as appropriate within a range which causes no degradation or deterioration in the hybrid gel of the present invention or in the encapsulated drug.

Other techniques for drug encapsulation include those in which a drug is complexed with a nanogel formed by a hydrophilic polysaccharide derivative having a hydrophobic group(s), and this nanogel/drug complex and a hyaluronic acid derivative are then crosslinked in situ to thereby form a hybrid gel. Without being limited thereto, conditions for complexation, e.g., the type of solvent, salt concentration, pH, temperature, time, addition of a denaturant, the concentration of the above hydrophilic polysaccharide derivative, drug concentration, and the ratio between HP and drug may be selected as appropriate such that the drug is stable and complexed with the nanogel in high yields. The uncomplexed free drug may be separated and removed by dialysis or size exclusion chromatography (SEC), etc. During in situ crosslinking, it is preferred to use crosslinking conditions which cause no denaturation in the drug complexed with the nanogel. In general, when a hyaluronic acid derivative and a drug are crosslinked in situ, it is necessary to use a selective crosslinking reaction which causes no reaction between drug and matrix, but it is difficult to obtain perfect selectivity. In the above technique, the drug complexed with HP is less reactive than the free drug, and is therefore advantageous in being less likely to cause a side reaction with the matrix even when crosslinked in situ with HA or a derivative thereof. The inventors of the present invention have made studies using erythropoietin (EPO) as a model drug and have indicated that there is a difference in the reactivity between CHP-complexed EPO and free EPO (Example 30). In the above technique, for example, a polymer having a nonionic skeleton such as CHP is particularly preferred for use as a hydrophilic polysaccharide derivative having a hydrophobic group(s). This is because, due to poor miscibility between nonionic polymer and anionic polymer such as hyaluronic acid or a derivative thereof, microphase separation will occur between CHP and the hyaluronic acid derivative, as a result of which the CHP-complexed drug in the nanogel is protected from chemical crosslinking reaction of the hyaluronic acid derivative. If necessary, in situ crosslinking may be followed by steps of grinding, drying and washing, etc. Conditions for each step may be selected as appropriate within a range which causes no degradation or deterioration in the hybrid gel of the present invention or in the encapsulated drug.

From the hybrid gel of the present invention, a drug is released by diffusion of the drug in the hybrid gel and of the complex between the drug and the hydrophilic polysaccharide derivative having a hydrophobic group(s), by degradation of the hybrid gel, and by replacement of the drug with a biological component. The drug to be released may be in the form of a free drug or a complex with the hydrophilic polysaccharide derivative having a hydrophobic group(s). For example, Non-patent Document 12 shows that when albumin is added in vitro to a CHP/insulin complex, replacement rapidly occurs to release free insulin, and that when this complex is directly administered by the intravenous route, replacement with blood components rapidly occurs to provide almost the same efficacy as obtained by administering an aqueous solution of free insulin. Thus, the drug released as a complex from the hybrid gel would be rapidly dissociated from the complex in the body.

In a case where drug release is induced by diffusion of the drug or complex, the drug release rate can be controlled by the crosslinking density of the hybrid gel of the present invention, as well as the amount and/or hydrophobicity of hydrophobically crosslinked domains. In particular, at high binding constant between drug and nanogel, the drug is released by diffusion of the complex. In this case, the drug release rate can be controlled independently of the type of drug to be encapsulated, simply by controlling the diffusion rate of the nanogel from the hybrid gel.

Degradation of the hybrid gel includes, for example, degradation of chemically crosslinked domains, skeletal degradation of the hyaluronic acid derivative, skeletal degradation of the hydrophilic polysaccharide derivative having a hydrophobic group(s), etc. These degradations will cause a decrease in the crosslinking density (i.e., an increase in the swelling ratio). In a case where the hyaluronic acid derivative and the hydrophilic polysaccharide derivative having a hydrophobic group(s) are chemically bonded, this bond will be cleaved. Upon decrease in the crosslinking density, the diffusion rate of the drug or complex in the hybrid gel will be accelerated to promote its release, and cleavage of the bonds will also promote the release. For this reason, the drug release rate can be controlled by controlling the degradability of chemically crosslinked domains, the degradability of polymer skeletons, the degradability of spacers, etc.

Replacement with biological components is intended to mean, for example, that upon in vivo administration of the hybrid gel (e.g., subcutaneously or intravenously), plasma proteins (e.g., albumin) or lipids present in the body penetrate into the hybrid gel and replace the drug encapsulated therein to thereby cause drug release. In the hybrid gel of the present invention, drug replacement associated with penetration of biological components can be controlled when a hydrophilic polysaccharide derivative having a hydrophobic group(s) such as CHP is encapsulated into a crosslinked hyaluronic acid derivative. For example, the inventors of the present invention have indicated that the drug release rate remains unchanged both in the presence and absence of excess albumin (Example 8). The penetration speed of biological components can be controlled, e.g., by the crosslinking density of the hybrid gel and/or the type of electric charge in the gel. It should be noted that in the above case where a hybrid gel is formed by crosslinking before adding a drug solution to encapsulate the drug thereinto, conditions for drug encapsulation can be selected as appropriate, such that the drug is easily absorbed into the hybrid gel during encapsulation, while penetration of biological components is inhibited in the body. Without being limited thereto, for example, in the case of protein encapsulation, the encapsulation step may be accomplished near the isoelectric point of the protein to inhibit electrostatic repulsion between hyaluronic acid derivative and drug. Moreover, the encapsulation step may be accomplished below the pKa (ca. 4.0) of carboxylic acid derived from glucuronic acid contained in hyaluronic acid to thereby reduce the negative charge of the hybrid gel, which makes it possible to inhibit electrostatic repulsion with proteins which are negatively charged under such conditions and thus to improve the encapsulation efficiency. Further, for example, the encapsulation step may be accomplished at a lower salt concentration than in the body, whereby the hybrid gel has a higher swelling ratio than in the body to facilitate encapsulation.

Upon further addition of an agent for prolonged release (e.g., a divalent metal ion or protamine sulfate) to the above drug-encapsulating hybrid gel, the sustained release period can be further prolonged. Examples of a divalent metal ion include zinc, magnesium, iron, calcium, aluminum, etc.

The size of the above hybrid gel can be adjusted depending on the intended purposes by using the above technique for gelling in a discontinuous phase or for grinding. For use as an injectable pharmaceutical composition, the preferred size is generally 0.01 µm to 150 µm. For percutaneous administration, 0.01 µm to 150 µm is preferred. For transnasal or transpulmonary administration, 0.01 µm to 5 µm is preferred in terms of inhalation efficiency. For intravenous injection, around 0.01 µm to 0.2 µm is preferred in terms of pharmacokinetics in blood.

It should be noted that the following can be listed as examples of a drug (i.e., a low-molecular-weight compound, a protein, a peptide, and a nucleic acid) to be encapsulated into the hybrid gel of the present invention.

Examples of a low-molecular-weight compound include carcinostatic agents (e.g., alkylating agents, antimetabolites, alkaloids), immunosuppressive agents, anti-inflammatory agents (e.g., steroid drugs, nonsteroidal anti-inflammatory agents), antirheumatic agents, antibacterial agents (e.g., β-lactam antibiotics, aminoglycoside antibiotics, macrolide antibiotics, tetracycline antibiotics, new quinolone antibiotics, sulfa drugs) and so on.

Examples of a protein or peptide include therapeutic agents for anemia, erythropoietin (EPO; serving as an organ protective agent), granulocyte colony-stimulating factor (G-CSF; serving as a therapeutic agent for neutropenia), interferon-α, β, γ, (INF-α, β, γ), thrombopoietin (TPO), ciliary neurotrophic factor (CNTF), tumor necrosis factor (TNF), tumor necrosis factor binding protein (TNFbp), interleukin-10 (IL-10), FMS-like tyrosine kinase (Flt-3), growth hormone (GH), insulin, insulin-like growth factor-1 (IGF-1), platelet derived growth factor (PDGF), interleukin-1 receptor antagonist (IL-1ra), brain-derived neurotrophic factor (BDNF), keratinocyte growth factor (KGF), stem cell factor (SCF), megakaryocyte growth and development factor (MGDF), osteoprotegerin (OPG), leptin, parathyroid hormone (PTH), basic fibroblastic growth factor (b-FGF), bone morphogenetic protein (BMP), atrial natriuretic peptide (ANP), brain natriuretic peptide (BNP), C-type natriuretic peptide (CNP), glucagon-like peptide-1 (GLP-1), drugs for various enzyme replacement therapies, antibody, diabody, minibody, fragmented antibody, and so on.

Examples of a nucleic acid include DNA, RNA, antisense, decoy, ribozyme, small interfering RNA, RNA aptamer, and so on.

After drug encapsulation, the hybrid gel of the present invention can be administered as a pharmaceutical composition in any dosage form suitable for the intended route of administration, in combination with one or more pharmaceutically acceptable diluents, wetting agents, emulsifiers, dispersants, auxiliaries, antiseptics, buffers, binders, stabilizers and the like. The route of administration may be either parenteral or oral.

Preferred drugs are proteins and peptides, and these drugs are encapsulated to obtain the compositions of the present invention containing proteins and peptides.

The present invention enables the provision of highly safe sustained-release formulations and pharmaceutical compositions that allow long-term sustained release of drugs such as proteins, peptides, nucleic acids and low-molecular-weight compounds, which could not be achieved by conventional sustained-release formulations.

EXAMPLES

The present invention will be further described in more detail in the following preferred examples.

In the following description, the term "HA unit" is intended to mean a repeated unit composed of N-acetylglucosamine and glucuronic acid in hyaluronic acid, which is defined as one unit. The ultrapure water used in the experiments was prepared using an ultrapure water generator (e.g., Millipore Milli-Q SP TOC (model ZD21TOCSP)).

Example 1

Synthesis of MA group-introduced HA derivative (HA-MA)

Example 1-1

Conversion of Cation Exchange Resin into Tetrabutylammonium (TBA) Salt Form

DOWEX® 50WX-8-400 (Aldrich) was suspended in ultrapure water and the resin was washed about three times with ultrapure water by decantation. A 40 wt % aqueous solution of tetrabutylammonium hydroxide (TBA-OH) (Aldrich) was added in an amount of about 1.5-fold molar equivalents relative to the cation exchange capacity of the resin, followed by stirring for about 30 minutes. After removing the excess of the TBA-OH solution by decantation, the resin was further washed with an excessive amount of ultrapure water to give a TBA salt of the cation exchange resin.

Example 1-2

Conversion of HA into TBA Salt Form

Hyaluronic acid sodium salt (HA-Na) having a molecular weight of 16 kDa, 100 kDa or 200 kDa (100 kDa was manufactured by Shiseido Co., Ltd., Japan and the others by Denki Kagaku Kogyo Kabushiki Kaisha, Japan) was dissolved in ultrapure water at a concentration of 15 mg/mL. A suspension of the TBA salt of the cation exchange resin obtained in Example 1-1 was added in an amount of 5-fold molar equivalents relative to HA units, calculated as the ion exchange capacity of the resin. After stirring for about 15 minutes, filtration was performed with a 0.45 pm filter and the filtrate was lyophilized to give hyaluronic acid TBA salt (HA-TBA) as a white solid.

HA-TBA thus obtained was dissolved in $D_2O$ at a concentration of about 10 mg/mL, followed by NMR structural analysis (calculated from the ratio of the integrated value for two methylenes in TBA ($N(CH_2\underline{CH_2CH_2}CH_3)_4$, 2H, 1.35-1.39 ppm and 2H, 1.64-1.67 ppm), based on the integrated value for acetyl group in glucosamine (3H, 1.75 ppm)) to calculate the ratio of TBA to HA units. This ratio was used to calculate the unit average molecular weight of TBA-HA, which was used for synthesis in the next section.

Example 1-3

Synthesis of Methacryloyl Group-Introduced HA Derivative (HA-MA)

HA-TBA of each molecular weight prepared in Example 1-2 was dissolved at 5 mg/mL in anhydrous DMSO. Then, 2-aminoethylmethacrylate hydrochloride (AEMA) (Polysciences, Inc.) was added to each solution at the ratio relative to HA units indicated in Table 1. Next, benzotriazol-1-yloxytris(dimethylamino)phosphonium hexafluorophosphate (BOP reagent) was added at the ratio relative to HA units indicated in Table 1 below and reacted overnight with mild stirring at room temperature. The reaction solution was purified by being dialyzed against 0.3M aqueous NaCl (SpectraPor 4, molecular weight cutoff (MWCO): 12 k-14 kDa, with 4 replacements of the external solution) and further against ultrapure water (with 6 replacements of the external solution). The resulting dialysate was lyophilized to give HA-MA as a white solid.

HA-MA thus obtained was dissolved in $D_2O$ at a concentration of about 10 mg/mL, followed by NMR structural analysis (calculated from the ratio of the integrated value for methylene in AEMA ($\underline{CH_2}$=$C(CH_3)CO_2CH_2CH_2NH$—, 5.60 ppm and 6.00 ppm), based on the integrated value for acetyl group in glucosamine) to calculate the introduction rate of MA groups relative to HA units. The introduction rate was used to calculate the unit average molecular weight of HA-AMEA (see Table 1).

The results suggest that the introduction rate of MA can be controlled by the amounts of the condensing agent (BOP reagent) and AEMA to be added.

TABLE 1

| | Preparation conditions and properties of HA-AEMA | | | |
|---|---|---|---|---|
| Abbreviation | Molecular weight of HA (kDa) | Added molar ratio of AEMA and BOP (HA unit/BOP/AEMA) | Introduction rate of MA (unit %) | Unit average molecular weight of HA-MA |
| HA-MA-1 | 16 | 1/0.2/5 | 10.5 | 410.7 |
| HA-MA-2 | 16 | 1/2.5/5 | 33.6 | 431.6 |
| HA-MA-3 | 16 | 1/2.5/5 | 38.2 | 435.7 |
| HA-MA-4 | 16 | 1/2.5/5 | 39.5 | 437.0 |
| HA-MA-5 | 100 | 1/2.5/5 | 35.9 | 433.7 |

TABLE 1-continued

Preparation conditions and properties of HA-AEMA

| Abbreviation | Molecular weight of HA (kDa) | Added molar ratio of AEMA and BOP (HA unit/BOP/AEMA) | Introduction rate of MA (unit %) | Unit average molecular weight of HA-MA |
|---|---|---|---|---|
| HA-MA-6 | 200 | 1/0.2/5 | 7.4 | 408.0 |
| HA-MA-7 | 200 | 1/0.4/5 | 18.7 | 418.1 |
| HA-MA-8 | 200 | 1/1.5/5 | 41.6 | 438.3 |
| HA-MA-9 | 200 | 1/2.5/5 | 43.1 | 440.1 |
| HA-MA-10 | 200 | 1/2.5/25 | 61.0 | 456.3 |

HA-MA-9 in Table 1 above is hereinafter also referred to as "HA-MA-200 k-43."

Example 2

Study on Preparation Conditions for Chemically Crosslinked HA-MA Gel

Example 2-1

Buffer Preparation for Gelling Reaction

To 500 mM phosphate buffer (PB, pH 8.0), triethanolamine (TEA) was added at 500 mM and mixed well. This was diluted 5-fold with ultrapure water and measured to have a pH of 9.2.

Example 2-2

Preparation of Aqueous Dithiothreitol (DTT) Solution

DTT was dissolved at 75 mg/mL (486.07 mM) in ultrapure water.

Example 2-3

Preparation of Chemically Crosslinked HA-MA Gel

The HA-MA derivatives used for each sample preparation (Samples 2-1 to 2-14) are shown in Table 2, along with their final concentrations.

The various HA-MA derivatives synthesized in Example 1 were each weighed into microtubes, followed by addition of ultrapure water. The tubes were allowed to stand overnight at 4° C. to obtain various concentrations of solutions shown in Table 2. Next, the TEA/PB solution prepared in Example 2-1 was added in ⅕ of the final volume and mixed well. Further, the aqueous DTT solution prepared in Example 2-2 was added in a ½ molar amount relative to the final concentration of MA groups (at a ratio of MA group:SH group=1:1) and mixed well. The final volume was set to around 100 μL in all cases. Air bubbles generated during mixing were removed by centrifugation, and each tube was allowed to stand at 37° C. for 14 hours to cause a chemical crosslinking reaction.

In Sample 2-7 and Sample 2-13, HA-MA was not completely dissolved.

TABLE 2

Preparation conditions for chemically crosslinked HA-MA (No. 1)

| Sample | HA-MA | Molecular weight of HA (kDa) | Introduction rate of MA (unit %) | Final conc. of HA-MA (mg/mL) | Final conc. of MA groups (mM) |
|---|---|---|---|---|---|
| 2-1 | HA-MA-1 | 16 | 10.5 | 40 | 10.23 |
| 2-2 | HA-MA-1 | 16 | 10.5 | 100 | 25.56 |
| 2-3 | HA-MA-1 | 16 | 10.5 | 200 | 51.13 |
| 2-4 | HA-MA-3 | 16 | 38.2 | 40 | 35.07 |
| 2-5 | HA-MA-3 | 16 | 38.2 | 100 | 87.67 |
| 2-6 | HA-MA-3 | 16 | 38.2 | 200 | 175.34 |
| 2-7 | HA-MA-3 | 16 | 38.2 | 400 | 350.68 |
| 2-8 | HA-MA-6 | 200 | 7.4 | 40 | 6.72 |
| 2-9 | HA-MA-7 | 200 | 18.7 | 40 | 16.98 |
| 2-10 | HA-MA-8 | 200 | 41.6 | 10 | 9.44 |
| 2-11 | HA-MA-8 | 200 | 41.6 | 20 | 18.88 |
| 2-12 | HA-MA-8 | 200 | 41.6 | 40 | 37.77 |
| 2-13 | HA-MA-8 | 200 | 41.6 | 80 | 75.54 |
| 2-14 | HA-MA-10 | 200 | 61.0 | 40 | 55.38 |

Example 2-4

Property Evaluation on Chemically Crosslinked HA-MA Gel

The gels prepared in Example 2-3 were collected from the microtubes and scored as follows: "−" for those observed no gelation, "±" for those partially gelled, and "+" for those completely gelled. Next, the gels which were completely gelled were swollen overnight at 4° C. with an excessive amount of ultrapure water. The individual swollen gels were treated with Kimwipes® to remove water on their surface and measured for their weight (weight in the swollen state). Next, the swollen gels were lyophilized and measured for their weight (dry weight). According to the following formula (1), the gel density in the swollen state was calculated (Table 3).

Gel density in the swollen state (% w/w)={(dry weight)/(weight in the swollen state)}×100     Formula (1)

TABLE 3

Preparation conditions and properties of chemically crosslinked HA-MA gels

| Sample | Molecular weight of HA (kDa) | Introduction rate of MA (unit %) | Final conc. of HA-MA (mg/mL) | Final conc. of MA groups (mM) | Score | Gel density in swollen state (% w/w) |
|---|---|---|---|---|---|---|
| 2-1 | 16 | 10.5 | 40 | 10.23 | − | NT |
| 2-2 | 16 | 10.5 | 100 | 25.56 | ± | NT |
| 2-3 | 16 | 10.5 | 200 | 51.13 | + | 2.47 |
| 2-4 | 16 | 38.2 | 40 | 35.07 | + | 0.91 |
| 2-5 | 16 | 38.2 | 100 | 87.67 | + | 4.87 |
| 2-6 | 16 | 38.2 | 200 | 175.34 | + | 7.81 |
| 2-7 | 16 | 38.2 | 300 | 263.01 | Not dissolved | NT |
| 2-8 | 200 | 7.4 | 40 | 6.72 | + | 0.28 |
| 2-9 | 200 | 18.7 | 40 | 16.98 | + | 0.52 |
| 2-10 | 200 | 41.6 | 10 | 9.44 | ± | NT |
| 2-11 | 200 | 41.6 | 20 | 18.88 | + | 0.55 |
| 2-12 | 200 | 41.6 | 40 | 37.77 | + | 1.08 |
| 2-13 | 200 | 41.6 | 60 | 56.64 | Not dissolved | NT |
| 2-14 | 200 | 61.0 | 40 | 55.38 | + | 1.12 |

NT: Not tested

The results suggested that a higher introduction rate of MA groups, which are crosslinking functional groups, resulted in a higher gel density, that a higher HA-MA concentration during crosslinking resulted in a higher gel density, and that a higher HA molecular weight caused gelling at a lower concentration.

Example 3

Preparation of Chemically Crosslinked HA-MA Hybrid Gel Encapsulating Cholesterol Group-Introduced Pullulan (CHP) (No. 1)

Example 3-1

Preparation of Aqueous CHP Solution

CHP substituted with 1.38 cholesterol groups per 100 monosaccharides in pullulan having a molecular weight of 100 kDa (hereinafter referred to as CHP-100-1.38; PUREBRIGHT CP-100T, NOF Corporation, Japan) was dissolved in DMSO at a concentration of 5 mg/mL. This DMSO solution was dialyzed against ultrapure water (SpectraPor 4, MWCO: 12 k-14 kDa), and the resulting aqueous solution was filtered through a 0.22 μm filter and lyophilized. The resulting white powder of CHP-100-1.38 was dissolved in ultrapure water at a concentration of 30 mg/mL to give an aqueous solution of CHP.

Example 3-2

Buffer Preparation for Gelling Reaction

To 500 mM phosphate buffer (PB, pH 8.0), triethanolamine (TEA) was added at 500 mM and mixed well.

Example 3-3

Preparation of Aqueous Dithiothreitol (DTT) Solution

DTT was dissolved at 25 mg/mL (162.02 mM) and 150 mg/mL (972.13 mM) in ultrapure water.

Example 3-4

Preparation of CHP-Encapsulating Chemically Crosslinked HA-MA

The HA-MA derivatives used for each preparation (Samples 3-1 to 3-18) are shown in Table 4, along with their final concentrations.

HA-MA-3 and HA-MA-8 synthesized in Example 1 were weighed into microtubes, followed by addition of ultrapure water and the aqueous CHP solution prepared in Example 3-1. The tubes were allowed to stand overnight at 4° C. to obtain various concentrations of solutions shown in Table 4. Next, the TEA/PB solution prepared in Example 3-2 was added in ⅕ of the final volume and mixed well. Further, the aqueous DTT solution prepared in Example 3-3 was added in a ½ molar amount relative to the final concentration of MA groups (at a ratio of MA group:SH group=1:1) (150 mg/mL solution was used for Samples 3-1 to 3-9, and 25 mg/mL solution for Samples 3-10 to 3-18) and mixed well. The final volume was set to around 100 μL in all cases. Air bubbles generated during mixing were removed by centrifugation, and each tube was allowed to stand at 37° C. for 14 hours to cause a chemical crosslinking reaction.

TABLE 4

Preparation conditions for CHP-encapsulating chemically crosslinked HA-MA hybrid gels (No. 1)

| Sample | HA-MA | Molecular weight of HA (kDa) | Introduction rate of MA (unit %) | Final conc. of HA-MA (mg/mL) | Final conc. of CHP (mg/mL) |
|---|---|---|---|---|---|
| 3-1 | HA-MA-3 | 16 | 38.2 | 50 | 5 |
| 3-2 | HA-MA-3 | 16 | 38.2 | 50 | 10 |
| 3-3 | HA-MA-3 | 16 | 38.2 | 50 | 20 |
| 3-4 | HA-MA-3 | 16 | 38.2 | 100 | 5 |
| 3-5 | HA-MA-3 | 16 | 38.2 | 100 | 10 |
| 3-6 | HA-MA-3 | 16 | 38.2 | 100 | 20 |
| 3-7 | HA-MA-3 | 16 | 38.2 | 200 | 5 |
| 3-8 | HA-MA-3 | 16 | 38.2 | 200 | 10 |
| 3-9 | HA-MA-3 | 16 | 38.2 | 200 | 20 |
| 3-10 | HA-MA-8 | 200 | 41.6 | 10 | 5 |
| 3-11 | HA-MA-8 | 200 | 41.6 | 10 | 10 |
| 3-12 | HA-MA-8 | 200 | 41.6 | 10 | 20 |
| 3-13 | HA-MA-8 | 200 | 41.6 | 20 | 5 |
| 3-14 | HA-MA-8 | 200 | 41.6 | 20 | 10 |
| 3-15 | HA-MA-8 | 200 | 41.6 | 20 | 20 |
| 3-16 | HA-MA-8 | 200 | 41.6 | 40 | 5 |
| 3-17 | HA-MA-8 | 200 | 41.6 | 40 | 10 |
| 3-18 | HA-MA-8 | 200 | 41.6 | 40 | 20 |

Example 3-5

Property Evaluation on CHP-Encapsulating Chemically Crosslinked HA-MA Hybrid Gel The chemically crosslinked HA-MA gels prepared in Example 3-4 were collected from the microtubes and scored as follows: "−" for those observed no gelation, "±" for those partially gelled, and "+" for those completely gelled. Moreover, information about the appearance of the gels (transparent, non-transparent) is also shown in Table 5. Next, the completely gelled samples were swollen overnight at 4° C. with an excessive amount of ultrapure water. Those swollen while retaining their initial gel form were defined as homogeneously swollen gels, and the rest were defined as non-homogeneously swollen gels. The individual swollen gels were treated with Kimwipes to remove water on their surface and measured for their weight (weight in the swollen state). Next, the swollen gels were lyophilized and measured for their weight (dry weight). According to the above formula (I), the gel density in the swollen state was calculated (Table 5).

TABLE 5

Preparation conditions and properties of CHP-encapsulating chemically crosslinked HA-MA hybrid gels (No. 1)

| Sample | Molecular weight of HA (kDa) | Final conc. of HA-MA (mg/mL) | Final conc. of CHP (mg/mL) | Score | Gel appearance | Gel form in swollen state | Gel density in swollen state (% w/w) |
|---|---|---|---|---|---|---|---|
| 3-1 | 16 | 50 | 5 | + | Transparent | Homogeneous | 1.82 |
| 3-2 | 16 | 50 | 10 | + | Non-transparent | Homogeneous | 2.06 |
| 3-3 | 16 | 50 | 20 | + | Non-transparent | Homogeneous | 2.19 |
| 3-4 | 16 | 100 | 5 | + | Transparent | Homogeneous | 5.01 |
| 3-5 | 16 | 100 | 10 | + | Transparent | Homogeneous | 5.39 |
| 3-6 | 16 | 100 | 20 | + | Non-transparent | Homogeneous | 5.68 |
| 3-7 | 16 | 200 | 5 | ± | Transparent | NT | NT |
| 3-8 | 16 | 200 | 10 | ± | Transparent | NT | NT |
| 3-9 | 16 | 200 | 20 | ± | Non-transparent | NT | NT |
| 3-10 | 200 | 10 | 5 | + | Transparent | Homogeneous | 0.28 |
| 3-11 | 200 | 10 | 10 | + | Transparent | Homogeneous | 0.30 |
| 3-12 | 200 | 10 | 20 | + | Transparent | Homogeneous | 0.37 |
| 3-13 | 200 | 20 | 5 | + | Transparent | Homogeneous | 0.61 |
| 3-14 | 200 | 20 | 10 | + | Transparent | Homogeneous | 0.75 |
| 3-15 | 200 | 20 | 20 | + | Non-transparent | Homogeneous | 0.86 |

TABLE 5-continued

Preparation conditions and properties of CHP-encapsulating chemically crosslinked HA-MA hybrid gels (No. 1)

| Sample | Molecular weight of HA (kDa) | Final conc. of HA-MA (mg/mL) | Final conc. of CHP (mg/mL) | Gel Score | Gel appearance | Gel form in swollen state | Gel density in swollen state (% w/w) |
|---|---|---|---|---|---|---|---|
| 3-16 | 200 | 40 | 5 | + | Transparent | Non-homogeneous | 1.08 |
| 3-17 | 200 | 40 | 10 | + | Transparent | Non-homogeneous | 1.79 |
| 3-18 | 200 | 40 | 20 | + | Non-transparent | Non-homogeneous | 1.78 |

NT: Not tested

All samples showed progress of gelling, but Samples 3-7 to 3-9 were not gelled completely. In Samples 3-7 to 3-9, the reason that gelling was not completed in the presence of CHP although HA-MA alone was gelled would be because mixing with CHP causes an increase in the solution viscosity before gelling and thereby inhibits homogeneous mixing of the polymers and crosslinking agent. On the other hand, Samples 3-16 to 3-18 showed non-homogeneous swelling behavior. This would be because mixing with CHP causes an increase in the solution viscosity before gelling and thereby inhibits homogeneous mixing of the polymers and crosslinking agent, as in the case of Samples 3-7 to 3-9, as a result of which non-homogeneous crosslinking occurs. Taken together with the results of Example 2, chemical crosslinking-mediated gelling at high concentration would have an upper limit due to solubility and/or viscosity, depending on the concentration and/or ratio of HA-MA and CHP in their mixture.

Moreover, some of the gels immediately after gelling reaction tended to be non-transparent with increases in the CHP concentration, but they became transparent after being swollen with ultrapure water. This would be due to a swelling-induced reduction in the gel density (polymer concentration), variations in pH, removal of TEA, etc.

The gel density in the swollen state was increased by elevating the CHP content. Since CHP does not participate in chemical crosslinking reaction during gelling, it was suggested that CHP remained encapsulated even upon swelling with ultrapure water. This result indicates that CHP-encapsulating chemically crosslinked HA-MA hybrid gels can be obtained with different composition and gel density.

Example 4

Preparation of CHP-Encapsulating Chemically Crosslinked HA-MA Hybrid Gel (No. 2)

Example 4-1

Buffer Preparation for Gelling Reaction

Triethanolamine (TEA) was dissolved at 500 mM in ultrapure water. This solution was diluted 5-fold with ultrapure water and measured to have a pH of 9.2.

Example 4-2

Preparation of Aqueous Dithiothreitol (DTT) Solution

DTT was dissolved at 150 mg/mL (972.13 mM) in ultrapure water.

Example 4-3

Preparation of CHP-Encapsulating Chemically Crosslinked HA-MA Hybrid Gel

The HA-MA derivatives used for each gel preparation (Samples 4-1 and 4-2) are shown in Table 6, along with their final concentrations.

HA-MA-3 synthesized in Example 1 was weighed into microtubes, followed by addition of ultrapure water and the aqueous CHP solution prepared in Example 3-1. The tubes were allowed to stand overnight at 4° C. to dissolve HA-MA-3 at various concentrations. Next, the aqueous TEA solution prepared in Example 4-1 was added in ⅕ of the final volume and mixed well. Further, the aqueous DTT solution prepared in Example 4-2 was added in a ½ molar amount relative to the final concentration of MA groups (at a ratio of MA group:SH group=1:1) and mixed well. The final volume was set to around 100 μL in all cases. Air bubbles generated during mixing were removed by centrifugation, and each tube was allowed to stand at 37° C. for 14 hours to cause a chemical crosslinking reaction.

TABLE 6

Preparation conditions for CHP-encapsulating chemically crosslinked HA-MA hybrid gels (No. 2)

| Sample | HA-MA | Molecular weight of HA (kDa) | Introduction rate of MA (unit %) | Final conc. of HA-MA (mg/mL) | Final conc. of CHP (mg/mL) |
|---|---|---|---|---|---|
| 4-1 | HA-MA-3 | 16 | 38.2 | 100 | 0 |
| 4-2 | HA-MA-3 | 16 | 38.2 | 100 | 20 |

Example 4-4

Property Evaluation on CHP-Encapsulating Chemically Crosslinked HA-MA Hybrid Gel The chemically crosslinked HA-MA gel and hybrid gel prepared in Example 4-3 were collected from the microtubes. Information about the appearance of the gels (transparent, non-transparent) is shown in Table 7. Next, the gels were swollen overnight at 4° C. with an excessive amount of ultrapure water. The individual swollen gels were treated with Kimwipes to remove water on their surface and measured for their weight (weight in the swollen state). Next, the swollen gels were lyophilized and measured for their weight (dry weight). According to the above formula (1), the gel density in the swollen state was calculated.

TABLE 7

Preparation conditions and properties of CHP-encapsulating chemically crosslinked HA-MA hybrid gels (No. 2)

| Sample | Final conc. of HA-MA (mg/mL) | Final conc. of CHP (mg/mL) | Buffer | Gel appearance | Gel density in swollen state (% w/w) |
|---|---|---|---|---|---|
| 4-1 | 100 | 0 | 100 mM TEA pH 9.2 | Transparent | 5.10 |
| 4-2 | 100 | 20 | 100 mM TEA pH 9.2 | Transparent | 6.13 |
| 2-5 | 100 | 0 | 100 mM TEA 100 mM PB pH 9.2 | Transparent | 4.87 |
| 3-6 | 100 | 20 | 100 mM TEA 100 mM PB pH 9.2 | Non transparent | 5.68 |

As seen from this result, even when PB is excluded from the reaction solution, chemically crosslinked HA-MA gels can be prepared. Moreover, the gels thus prepared were found to have an increased gel density, suggesting that the reaction efficiency of chemical crosslinking was high in this case. Furthermore, in Sample 4-2, the gel did not become non-transparent. Taken together with the finding obtained in Example 3 that the non-transparent gels became transparent when swollen with ultrapure water, the results of this example suggest that phase separation between HA-MA and CHP can be inhibited by reducing the salt concentration in the solution.

Example 5

Evaluation on Drug Absorption Property, Drug Release Profile and Gel Degradability of CHP-Encapsulating Chemically Crosslinked HA-MA Hybrid Gel Example 5-1

Encapsulation of FITC-Ins into Hybrid Gel

FITC-Ins (Aldrich) was dissolved in 100 mM PB (pH 7.4) at a concentration of 100 μg/mL. To the hybrid gels of Samples 3-1 to 3-6 prepared in Example 3, which had been lyophilized, 5 mL of the FITC-Ins solution was added and incubated at 4° C. for 2 days. These individual hybrid gels, which were colorless and transparent when swollen in Example 3, were found to show a yellow color that was darker than their surrounding FITC-Ins solution. This suggested that the hybrid gels spontaneously absorbed and held FITC-Ins therein. FIG. 1 shows the appearance of the hybrid gels after removal of the FITC-Ins solution.

Example 5-2

Evaluation on FITC-Ins Release Property of Hybrid Gel

Figure 2:
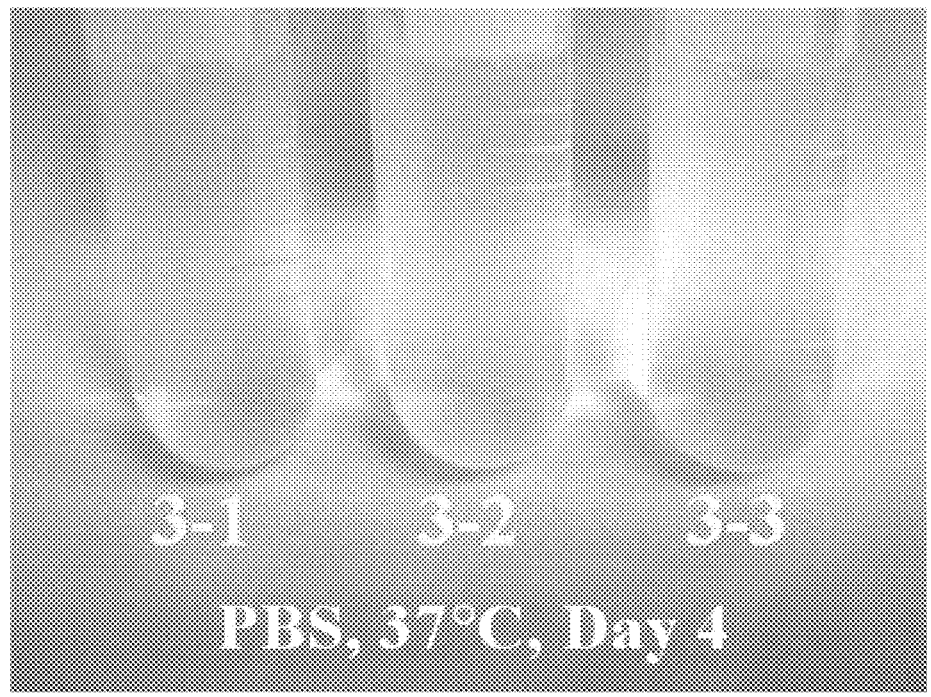
FIG. 2 is one example of a photograph showing CHP-encapsulating chemically crosslinked HA-MA hybrid gels in buffer after FITC-Ins absorption.
Figure 2:
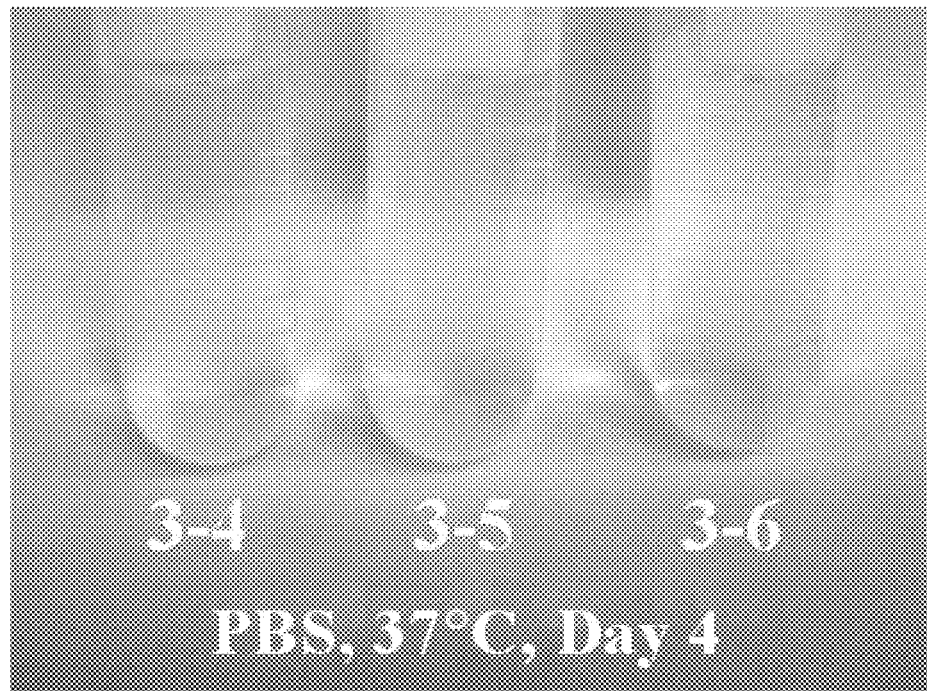
Figure 3:
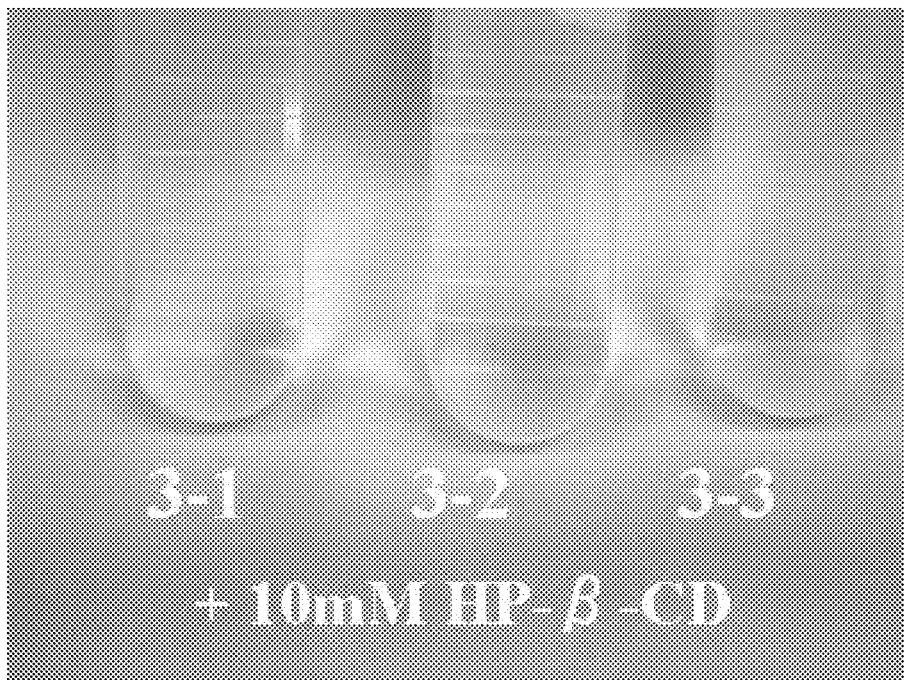
FIG. 3 is one example of a photograph showing CHP-encapsulating chemically crosslinked HA-MA hybrid gels upon addition of cyclodextrin after FITC-Ins absorption.
Figure 3:
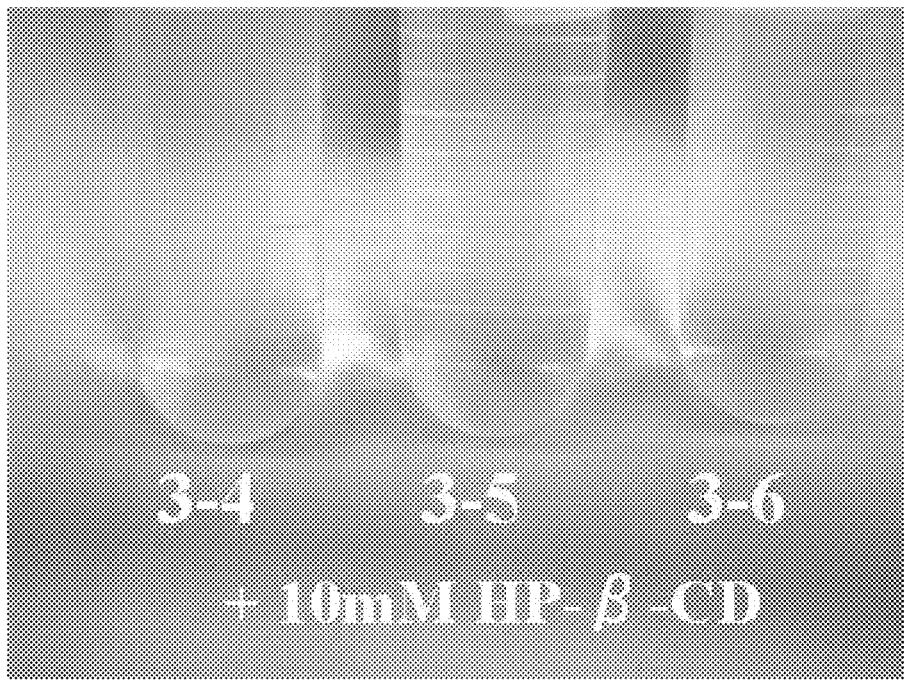

To the hybrid gels treated to encapsulate FITC-Ins in Example 5-1, 5 mL of PBS (pH 7.4) added and incubated at 37° C. for 4 days. Their appearances at this time are shown in FIG. 2. The individual hybrid gels remained yellow, while their surrounding aqueous solutions remained colorless and transparent, suggesting that FITC-Ins spontaneously absorbed and held was not rapidly released. Next, a 100 mM aqueous solution of 2-hydroxypropyl-β-cyclodextrin (HP-β-CD, Junsei Chemical Co., Ltd., Japan) was added at a final concentration of 10 mM and incubated at 37° C. The gel appearance was observed over time, indicating that the hybrid gels showing a yellow color were gradually discolored, while their surrounding aqueous solutions were gradually turned into yellow (appearance at 2 hours after HP-β-CD addition, FIG. 3). Cyclodextrin is known to include therein cholesterol groups of CHP and thereby induces the release of proteins or peptides associated with cholesterol groups by hydrophobic interaction. This indicated that FITC-Ins was held by hydrophobic interaction with cholesterol groups. Moreover, CHP nanogels are known to be spontaneously complexed with insulin in an aqueous solution, and were also confirmed to retain their complexation capacity in the hybrid gels prepared in Example 3.

Example 5-3

Evaluation on Degradability of Hybrid Gel

Figure 4:
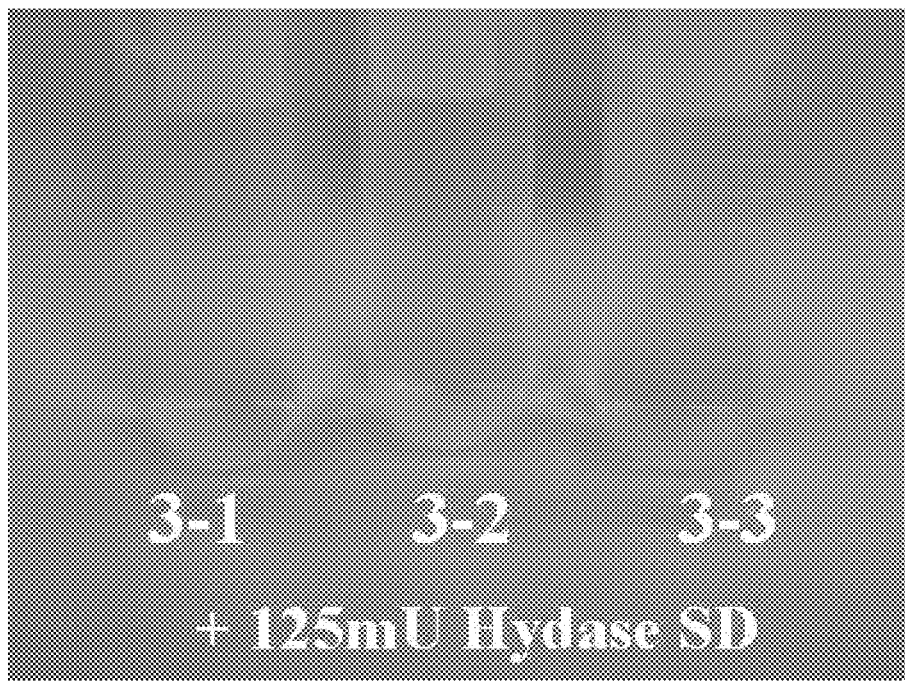
FIG. 4 is one example of a photograph showing CHP-encapsulating chemically crosslinked HA-MA hybrid gels upon addition of hyaluronidase after FITC-Ins absorption.
Figure 4:
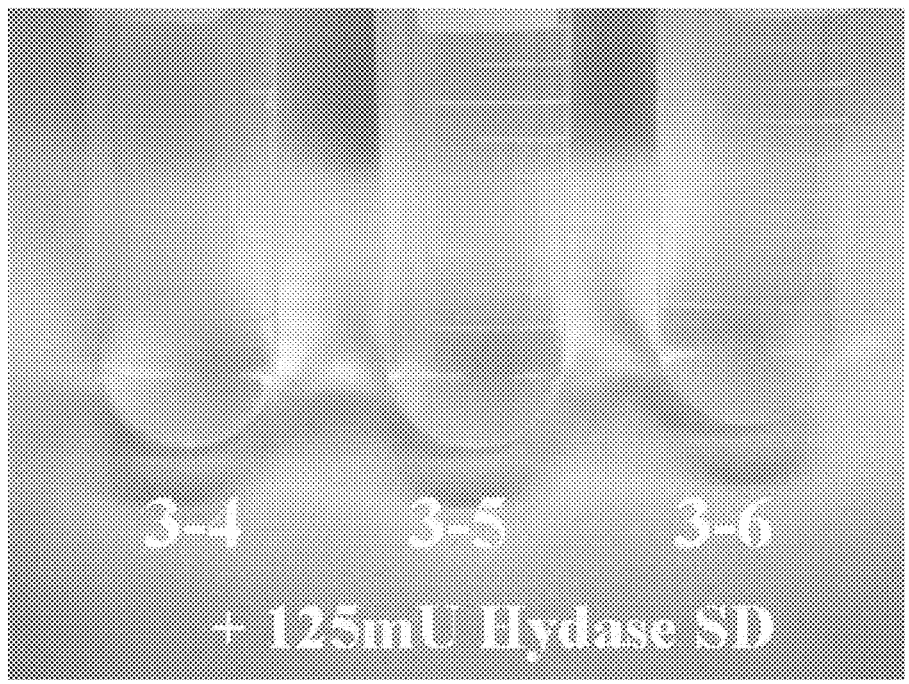

To the samples evaluated for their release property in Example 5-2 (2 hours after CD addition), 125 mU hyaluronidase SD (HydaseSD, Seikagaku Corporation, Japan) was added and incubated at 37° C. for 2 days. Their appearances at this time are shown in FIG. 4. The hybrid gels of Samples 3-1 to 3-3, which were prepared from HA-MA having MA groups introduced into HA with a molecular weight of 16 kDa by gelling at a concentration of 50 mg/mL, were found to be completely degraded upon enzyme addition and turned into solutions showing a homogeneous light-yellow color, thus suggesting that the encapsulated FITC-Ins was completely released. On the other hand, the hybrid gels of Samples 3-4 to 3-6 prepared by gelling at a concentration of 100 mg/mL were mostly degraded, but there remained pieces of the gels showing a light-yellow color. This suggested that the hybrid gels prepared in Example 3 were biodegradable and had different degradation rates depending on their gel density. In addition to Example 5-2 indicating that FITC-Ins release was induced by cleavage of hydrophobic interaction between FITC-Ins and cholesterol groups upon inclusion of these cholesterol groups within cyclodextrin, this example suggested that drug release was also caused by degradation of the hybrid gels.

Example 6

Encapsulation of Insulin into CHP-Encapsulating Chemically Crosslinked HA-MA Hybrid Gel

Example 6-1

Preparation of CHP-Encapsulating Chemically Crosslinked HA-MA Hybrid Gel

The same procedure as shown in Example 4 was repeated to prepare the hybrid gels indicated in Table 8.

TABLE 8

Preparation conditions for CHP-encapsulating chemically crosslinked HA-MA hybrid gels (No. 3)

| Sample | HA-MA | Molecular weight of HA (kDa) | Introduction rate of MA (unit %) | Final conc. of HA-MA (mg/mL) | Final conc. of CHP (mg/mL) |
|---|---|---|---|---|---|
| 6-1 | HA-MA-2 | 16 | 33.6 | 50 | 5 |
| 6-2 | HA-MA-2 | 16 | 33.6 | 50 | 20 |
| 6-3 | HA-MA-2 | 16 | 33.6 | 50 | 20 |
| 6-4 | HA-MA-2 | 16 | 33.6 | 100 | 20 |
| 6-5 | HA-MA-5 | 100 | 35.9 | 50 | 20 |

Example 6-2

Time Course of Insulin Encapsulation and Calculation of Encapsulated Amount

Figure 5:
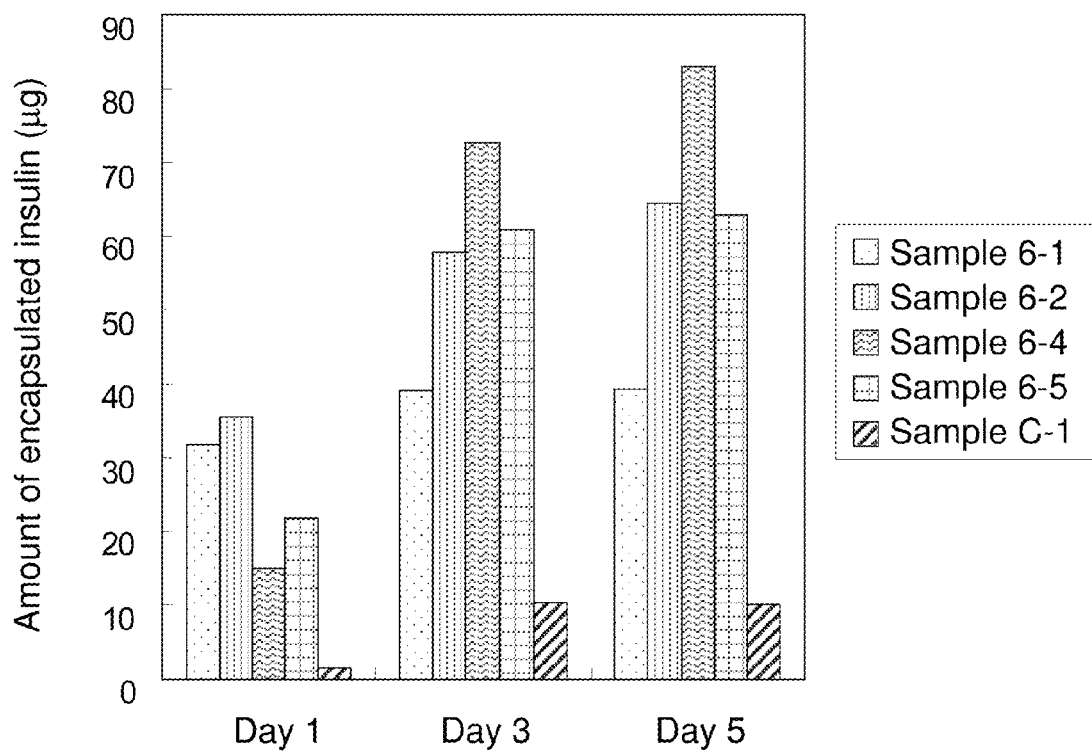
FIG. 5 is a graph showing the amount of insulin absorbed into CHP-encapsulating chemically crosslinked HA-MA hybrid gels.

The hybrid gels prepared in Example 6-1 were collected from the microtubes and swollen overnight at 4° C. with an excessive amount of ultrapure water. After removal of ultrapure water by decantation, the swollen gels were lyophilized. 4 mL of 150 mM PB (pH 7.4) was added to each lyophilized gel to swell it overnight at 4° C., followed by decantation to remove PB. Insulin (derived from bovine pancreas, SIGMA) was dissolved at 100 μg/mL in 150 mM PB (pH 7.4). The insulin solution was added to each gel and allowed to stand at 4° C., such that 15 moles of insulin molecules were added relative to 4 moles of CHP based on the initial amount for gel preparation, assuming that insulin had a molecular weight of 5,733.5. At 1 day, 3 days and 5 days after addition of the insulin solution, the supernatant was collected in 70 μL volumes and the insulin concentration in each supernatant was quantified by reversed-phase liquid chromatography (RP-HPLC). FIG. 5 shows a graph that plots the amount of insulin lost from the supernatant (=the amount of insulin encapsulated into the gel, corrected for loss of insulin in the supernatant collected for quantification purposes) (data for Sample 6-3 are omitted because it was prepared under the same conditions as Sample 6-2). Analysis conditions for RP-HPLC are as shown below. The insulin solution added was removed by decantation, and each gel was provided for Example 7.

RP-HPLC Conditions

System: Waters Alliance 2790/2487
Column: Cadenza CD18-C (3 μm) 3.0 mm×50 mm (Imtakt)
Flow rate: 0.75 mL/minute
Detection: UV (280 nm)
Eluent A: 0.01% w/v TFA-containing ultrapure water
Eluent B: 0.01% w/v TFA-containing acetonitrile
Elution: linear gradient of Eluent A/Eluent B=80/20 to 50/50

As a result, as in the case of Example 5, insulin was spontaneously encapsulated into the hybrid gels. Comparison between Sample 6-1 and Sample 6-2 indicated that the amount of insulin encapsulated into the hybrid gel depended on the CHP content, and thus suggested that CHP in the hybrid gel functioned as a reservoir to hold insulin. Moreover, comparison between Sample 6-2 and Sample 6-4 indicated that the encapsulation rate was slower at a higher crosslinking density of the gel, and thus suggested that the diffusion rate of insulin into the gel depended on the crosslinking density of the gel.

Comparative Example 1

Encapsulation of Insulin into HA-MA Chemically Crosslinked Gel

Comparative Example 1-1

Preparation of HA-MA Chemically Crosslinked Hybrid Gel

The same procedure as shown in Example 4 was repeated to prepare the chemically crosslinked HA-MA gel indicated in Table 9.

TABLE 9

Preparation conditions for chemically crosslinked HA-MA (No. 2)

| Sample | HA-MA | Molecular weight of HA (kDa) | Introduction rate of MA (unit %) | Final conc. of HA-MA (mg/mL) | Final conc. of CHP (mg/mL) |
|---|---|---|---|---|---|
| C-1 | HA-MA-2 | 16 | 33.6 | 50 | 0 |

Comparative Example 1-2

Time Course of Insulin Encapsulation and
Calculation of Encapsulated Amount

Insulin was encapsulated into the chemically crosslinked HA-MA gel prepared in Comparative Example 1-1 in the same manner as shown in Example 6-2. The insulin solution was added in the same amount as used for Sample 6-2 in Example 6-2. The amount of insulin encapsulated into the gel is also shown in FIG. 5. As a result, the amount of insulin encapsulated into the CHP-free HA gel was extremely small when compared to the hybrid gels. This suggested that the chemically crosslinked HA-MA gel used in this study had per se little ability to spontaneously absorb insulin.

Example 7

Release Behavior of Insulin from Chp-Encapsulating
Chemically Crosslinked HA-MA Hybrid Gel To remove insulin molecules which were not held in the hybrid gel or by the surface CHP, 5 mL of 10 mM PB, 150 mM NaCl, pH 7.4 (PBS) was added to the hybrid gels treated to encapsulate insulin in Example 6. The gels were allowed to stand at 4° C. for 1 hour and then decanted to remove PBS. Further, 5 mL of PBS was added and allowed to stand at 4° C. for 1 day, followed by removal of PBS. This procedure was repeated again.

Figure 6:
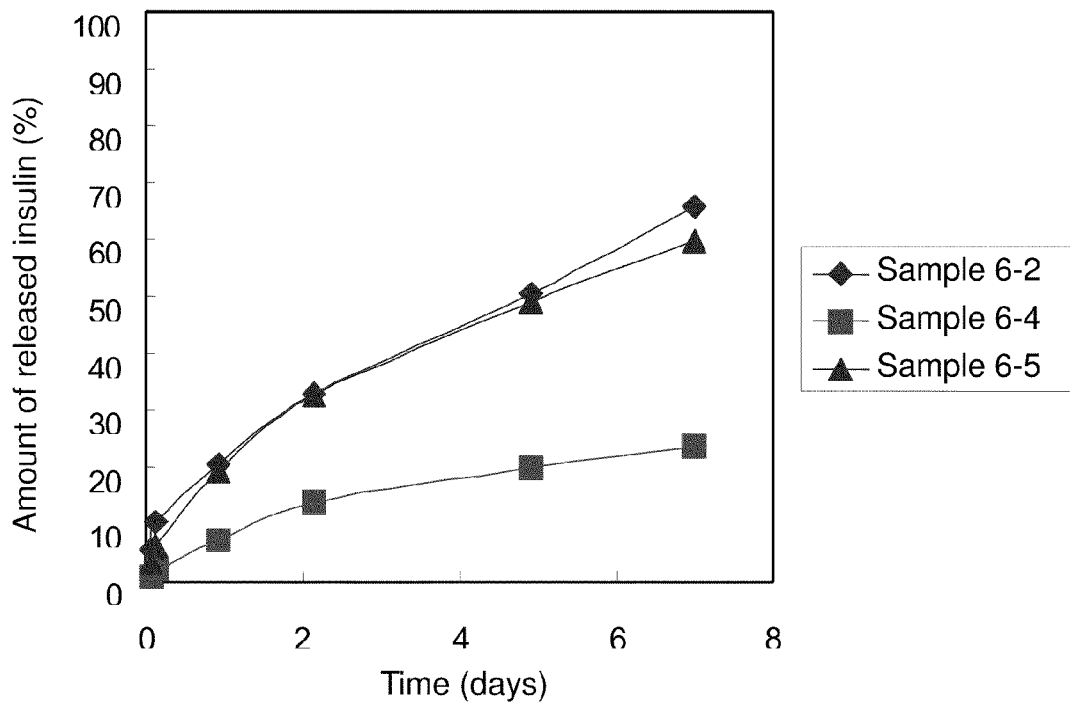
FIG. 6 is a graph showing the amount of insulin released from CHP-encapsulating chemically crosslinked HA-MA hybrid gels.
Figure 7:
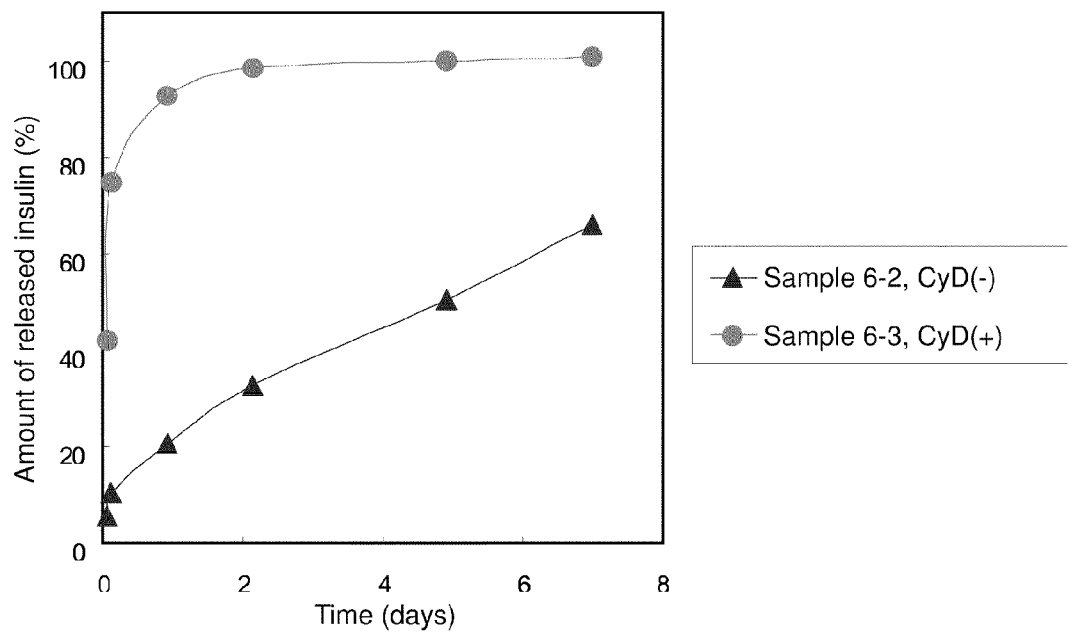
FIG. 7 is a graph showing the effect of cyclodextrin on the amount of insulin released from CHP-encapsulating chemically crosslinked HA-MA hybrid gels.

The hybrid gels of Sample 6-2, Sample 6-4 and Sample 6-5 received 500 µL of PBS, while the hybrid gel of Sample 6-3 received 500 µL of 10 mM HP-β-CD-containing PBS, followed by incubation at 37° C. At 1 hour, 3 hours, 1 day, 2 days, 5 days and 7 days after initiation of the incubation, 400 µL supernatant was collected and 400 µL fresh release buffer (CD-free PBS (CD(−)) or CD-containing PBS (CD(+))) was added instead. The insulin concentration in each collected supernatant was quantified by RP-HPLC (under the same conditions as shown in Example 6-2) to calculate the cumulative amount of insulin released from the hybrid gel until each time point for measurement. This value is plotted as a percentage of the amount of encapsulated insulin (calculated in Example 6-2) in FIGS. 6 and 7.

As a result, the release behavior of insulin from the CHP-encapsulating chemically crosslinked HA-MA hybrid gels was found to have a sustained release profile with a small initial burst, and comparison between Sample 6-2 and Sample 6-4 indicated that the release rate depended on the gel density (crosslinking density). This suggests that control of the crosslinking density allows control of the drug release rate. The release rates from the hybrid gels of Sample 6-2 and Sample 6-5 were almost at the same level. These two samples have almost the same gel density although they use HA of different molecular weights. Taken together with the above results, it was indicated that the release rate was defined by the gel density. Moreover, comparison between Sample 6-2 and Sample 6-3 indicated that the release rate of insulin was greatly accelerated upon addition of cyclodextrin. As in the case of the results in Example 5, it was indicated that insulin was held by hydrophobic interaction with cholesterol groups, and CHP nanogels also retained their complexation capacity in the hybrid gels.

Moreover, when the supernatants collected in the release test were analyzed by size exclusion chromatography (SEC) as shown below, the released species detected was only insulin/nanogel complexes (retention time: 6.2 minutes) in all samples but Sample 6-3, while the released species detected were the complexes and free insulin (retention time: 10.8 minutes) in Sample 6-3. These results indicated that the CHP-encapsulating chemically crosslinked HA-MA hybrid gels sustainedly released insulin/nanogel complexes, and that free insulin was released upon inclusion of hydrophobic groups (cholesterol groups) within cyclodextrin.

SEC Analysis Conditions
System: Waters Alliance 2790/2487
Column: G2000SWXL (TOSOH)
Flow rate: 1.0 mL/minute
Detection: UV detection (280 nm)
Eluent: PBS
Injection volume: 100 µL

Example 8

Evaluation on Encapsulation and Release Properties
into/from CHP-Encapsulating Chemically
Crosslinked HA-MA Hybrid Gel

Example 8-1

Preparation of CHP-Encapsulating Chemically
Crosslinked HA-MA Hybrid Gel

The same procedure as shown in Example 4 was repeated to prepare the hybrid gels indicated in Table 10, such that the resulting hybrid gel solutions had a final volume of 50 µL.

TABLE 10

Preparation conditions for CHP-encapsulating chemically crosslinked HA-MA hybrid gels (No. 4)

| Sample | HA-MA | Molecular weight of HA (kDa) | Introduction rate of MA (unit %) | Final conc. of HA-MA (mg/mL) | Final conc. of CHP (mg/mL) |
|---|---|---|---|---|---|
| 8-1 | HA-MA-2 | 16 | 33.6 | 50 | 20 |
| 8-2 | HA-MA-2 | 16 | 33.6 | 100 | 20 |
| 8-3 | HA-MA-2 | 16 | 33.6 | 100 | 20 |

Example 8-2

Calculation of the Amount of Encapsulated FITC-Ins

Figure 8:
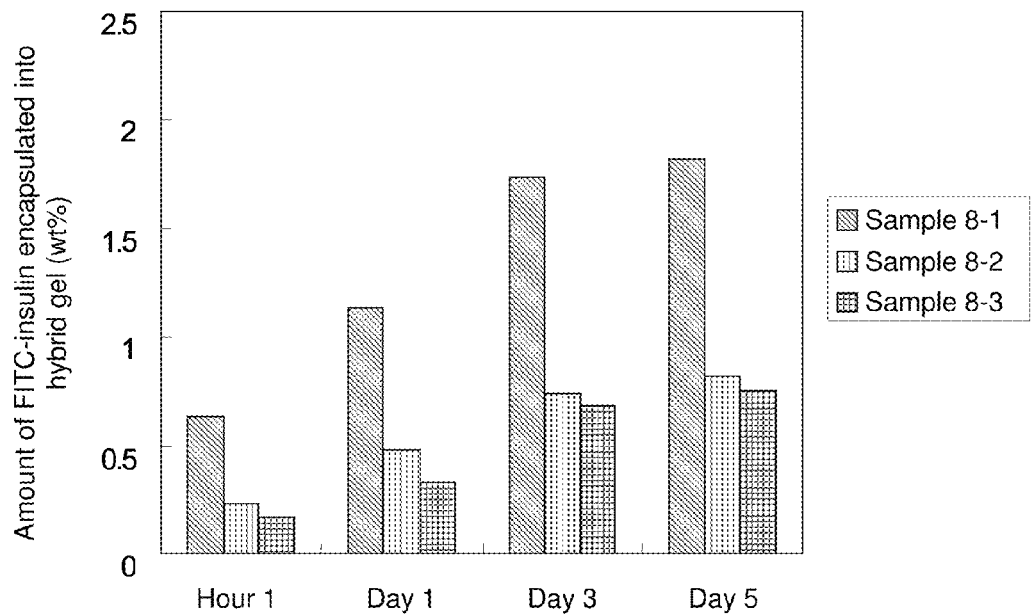
FIG. 8 is a graph showing the amount of FITC-Ins absorbed into CHP-encapsulating chemically crosslinked HA-MA hybrid gels.

The hybrid gels prepared in Example 8-1 were collected from the microtubes and swollen overnight at 4° C. with an excessive amount of ultrapure water. After removal of ultrapure water by decantation, the swollen gels were lyophilized. 4 mL of 150 mM PB (pH 7.4) was added to each lyophilized gel to swell it overnight at 4° C., followed by decantation to remove PB. FITC-Ins (Aldrich) was dissolved at 100 µg/mL in 150 mM PB (pH 7.4). The FITC-Ins solution was added to each gel and allowed to stand at 4° C., such that 15 moles of FITC-Ins molecules were added per 4 moles of CHP based on the initial amount for gel preparation, assuming that FITC-Ins had a molecular weight of 6122.49 (given that one molecule of FITC was attached to one molecule of insulin). At 1 hour, 1 day, 3 days and 5 days after addition of the insulin solution, the supernatant was collected in 100 µL volumes and the FITC-Ins concentration in each supernatant was quantified with a spectrophotometer (detection wavelength: 494 nm). The amount of FITC-Ins lost from the supernatant (=the amount of FITC-Ins encapsulated into the gel, corrected for loss of FITC-Ins in the supernatant collected for quantification purposes) was calculated. FIG. 8 shows a graph that plots the amount of FITC-Ins encapsulated into each gel of Samples 8-1 to 8-3 as a percentage by weight relative to the dry weight of the hybrid gel. The FITC-Ins solution added was removed by decantation and each gel was provided for Example 8-3.

Example 8-3

Release Behavior of FITC-Ins from Hybrid Gel

To each hybrid gel treated to encapsulate FITC-Ins in Example 8-2, 5 mL of 10 mM PB, 150 mM NaCl, pH 7.4 (PBS) was added and allowed to stand at 4° C. for 1 hour, followed by decantation to remove PBS. Further, 5 mL of PBS was added and allowed to stand at 4° C. for 1 day, followed by removal of PBS. This procedure was repeated again. This procedure appears to remove FITC-Ins molecules which are not held in the hybrid gel or by the surface CHP.

Figure 9:
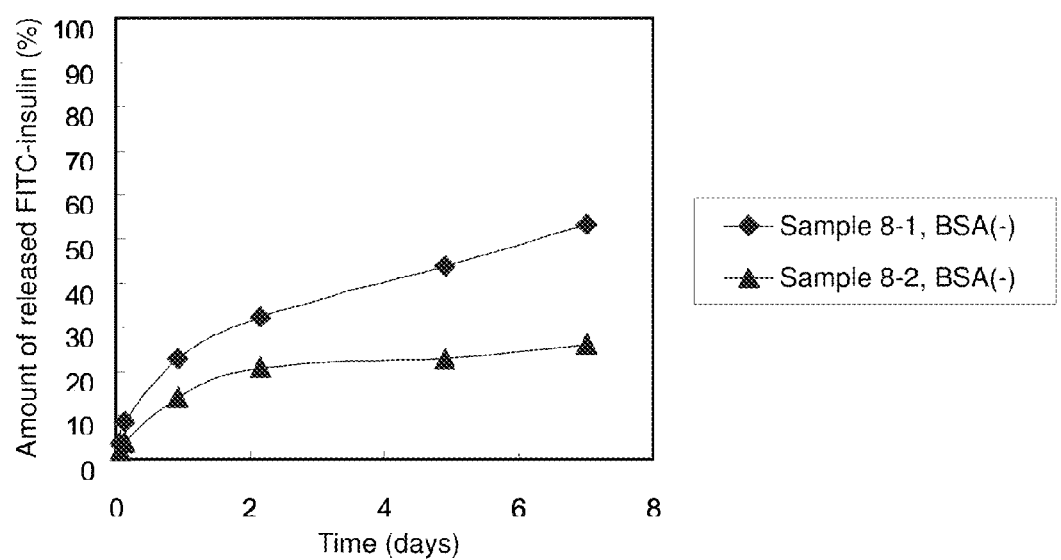
FIG. 9 is a graph showing the amount of FITC-Ins released from CHP-encapsulating chemically crosslinked HA-MA hybrid gels.
Figure 10:
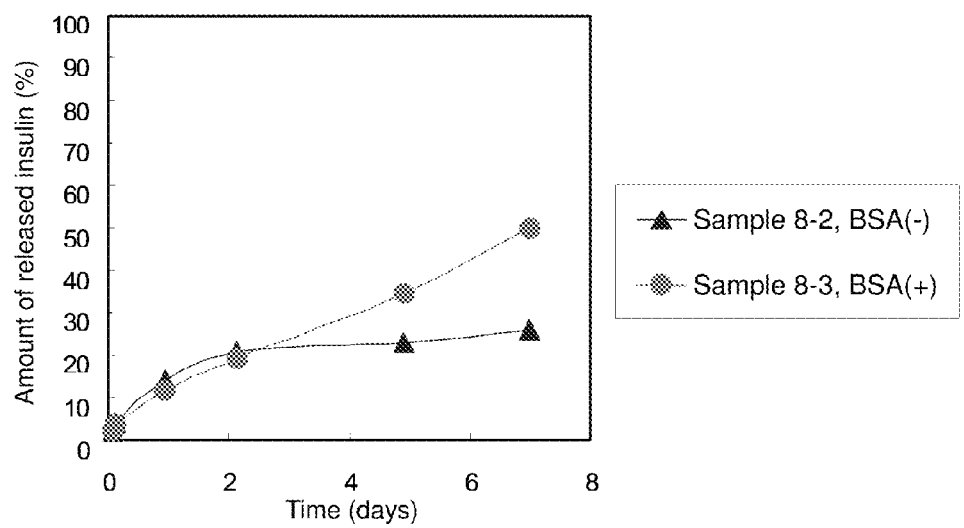
FIG. 10 is a graph showing the effect of albumin on the release behavior of FITC-Ins from CHP-encapsulating chemically crosslinked HA-MA hybrid gels.

The hybrid gels of Sample 8-1 and Sample 8-2 received 500 μL of PBS, while the hybrid gel of Sample 8-3 received 500 μL of 10 mg/mL bovine serum albumin (BSA)-containing PBS, followed by incubation at 37° C. At 1 hour, 3 hours, 1 day, 2 days, 5 days and 7 days after initiation of the incubation, 400 μL supernatant was collected and 400 μL fresh release buffer (BSA-free PBS (BSA(−)) or BSA-containing PBS (BSA(+))) was added instead. The FITC-Ins concentration in each collected supernatant was quantified by size exclusion chromatography (SEC) to calculate the cumulative amount of FITC-Ins released from the hybrid gel until each time point for measurement. This value is plotted as a percentage of the amount of FITC-Ins encapsulated into the hybrid gel (calculated in Example 8-2) in FIGS. 9 and 10. The SEC analysis conditions used are as shown below.

SEC Analysis Conditions

System: Waters Alliance 2790/2475

Column: G2000SWXL (TOSOH)

Flow rate: 1.0 mL/minute

Detection: fluorescence detection (excitation wavelength: 494 nm, detection wavelength: 518 nm)

Eluent: 10 mM HP-β-CD-containing PBS

Each sample was diluted 20-fold with 0.05% w/v Tween80-containing PBS and then applied to HPLC in a volume of 10 μL.

As a result, the release rate of FITC-Ins from the hybrid gels was found to depend on their gel density, as in the case of Example 7, suggesting that that the release rate can be controlled by the gel density.

Moreover, although it is known that insulin release occurs rapidly (within several hours) upon addition of BSA to complexes between CHP nanogel and insulin in a solution state, the release rate from the hybrid gel remained substantially unchanged within 1 or 2 days. This suggested that BSA did not rapidly diffuse into the hybrid gel. At 5 days or later, the release amount was increased in the BSA(+) case. This would be because hydrolysis of more chemical crosslinking points causes a further reduction in the gel density, as a result of which BSA is more likely to diffuse into the hybrid gel.

Example 9

Synthesis of SH Group-Introduced HA Derivative (HA-SH)

Example 9-1

Synthesis of HZ Group-Introduced HA Derivative (HA-HZ)

Sodium hyaluronates (HA-Na) having molecular weights of 20 kDa and 200 kDa (Denki Kagaku Kogyo Kabushiki Kaisha, Japan; 536.9 mg and 524.8 mg, respectively) were each dissolved at 2 mg/mL in ultrapure water, followed by addition of an equal volume of ethanol (EtOH) to give 50% v/v EtOH solutions. At an equivalent ratio of HA unit/1-ethyl-3-(3-dimethylaminopropyl)carbodiimide (EDC, Dojindo Co., Ltd., Japan)/adipic acid dihydrazide (ADH, Tokyo Chemical Industry Co., Ltd., Japan)=1/0.25/40 (mol/mol/mol), these were added and reacted. The pH was kept at 4.7 to 4.8 with 5N aqueous HCl. After reaction for 2 hours, each reaction solution was purified by dialysis successively against 100 mM aqueous NaCl, 25% v/v aqueous EtOH and ultrapure water (SpectraPor 4, MWCO: 12 k-14 kDa), concentrated by ultrafiltration (YM-10, MWCO: 10 kDa, Millipore Corporation) and then lyophilized to give HA-HZ as a white powder. The yield was 490.93 mg for the case of starting from 20 kDa HA and 375.77 mg for the case of starting from 200 kDa HA.

The resulting HA-HZ derivatives were each dissolved in $D_2O$ at a concentration of about 10 mg/mL, followed by NMR structural analysis (calculated from the ratio of the integrated value for 4 methylenes in ADH (1.5, 2.1 and 2.25 ppm), based on the integrated value for acetyl group in glucosamine) to calculate the introduction rate of HZ groups relative to HA units, indicating that it was 20.3% for the case of starting from 20 kDa HA and 32.0% for the case of starting from 200 kDa HA. These introduction rates were further used to calculate the unit average molecular weight of HA-HZ for each case, which was used for synthesis in the next section.

Example 9-2

Synthesis of SH Group-Introduced HA Derivative (HA-SH)

The HA-HZ derivatives of different molecular weights obtained in Example 9-1 (480.54 mg and 365.21 mg, respectively) were each dissolved at 20 mg/mL in ultrapure water, followed by addition of 2-iminothiolane hydrochloride (Pierce) in an amount of about 2-fold equivalents relative to HZ groups. After reaction at room temperature for 3 hours, 100 mL of EtOH was added to precipitate the desired product. The precipitate was collected by centrifugation, washed with EtOH and then dried under reduced pressure to give HA-SH as a white solid. The yield was 513.72 mg for the case of starting from 20 kDa HA and 371.58 mg for the case of starting from 200 kDa HA.

The resulting HA-SH derivatives were each dissolved in $D_2O$ at a concentration of about 10 mg/mL, followed by NMR structural analysis (calculated from the ratio of the integrated value for methylene (2.85 ppm) adjacent to SH group, based on the integrated value for acetyl group in glucosamine) to calculate the introduction rate of SH groups relative to HA units, indicating that it was 18.0% for the case of starting from 20 kDa HA (this HA-SH derivative is hereinafter also referred to as "HA-SH-20 k-18") and 27.0% for the case of starting from 200 kDa HA (this HA-SH derivative is hereinafter also referred to as "HA-SH-200 k-27"). These introduction rates were further used to calculate the unit average molecular weight of HA-SH for each case, which was used for hybrid gel preparation in Example 11.

Example 10

Synthesis of MA Group-Introduced CHP (CHP-MA) and Association Behavior Thereof in Aqueous Solution

Example 10

Synthesis of CHP-MA (No. 1)

CHP (degree of cholesterol substitution=1.5/100 monosaccharides, Mw=108 kDa, purchased from NOF Corporation, Japan) was dried under reduced pressure at 60° C. for 2 days. A 100 mL three-necked flask, which had been dried under reduced pressure, was flame-dried and then capped with rubber stoppers, followed by addition of 1 g (9.26 μmol) of CHP and 257.5 mg (2.11 mmol) of dimethylaminopyridine (DMAP) under a nitrogen stream. A glass syringe was used to add 25 mL of DMSO, and the mixture was stirred until complete dissolution at room temperature for about 1 hour and then injected with 92.6 μL (0.7 mmol) of glycidyl methacrylate (GMA), followed by reaction at room temperature for 24 hours. Several drops of 1 M hydrochloric acid were added to stop the reaction, followed by addition of distilled water to give a total volume of about 100 mL. The reaction solution was transferred to a dialysis tube (SpectraPor 6, MWCO: 3500), dialyzed against distilled water for 1 week and then lyophilized to give the desired product as a white solid.

CHP-MA thus obtained was dissolved in a mixed solvent of DMSO-$d_6$ and $D_2O$ (20:1 by volume), followed by NMR structural analysis. The integrated value for protons (anomeric protons (α1-6), 4.60-7.75 ppm) on 1-position carbons in α1-6 linkage-forming glucose units contained in pullulan was compared with the integrated value for methylene in MA groups (5.65 ppm and 6.15 ppm) to calculate the introduction rate of MA groups relative to glucose units, indicating that it was 2.4% (this CHP-MA derivative is hereinafter also referred to as "CHP-MA-2.4").

Example 10-2

Synthesis of CHP-MA (No. 2)

Except that GMA was added in an amount of 277.8 μL (2.11 mmol), the same procedure as used in Example 10-1 was repeated to give a white solid of CHP-MA. Upon NMR structural analysis, the introduction rate of MA groups relative to glucose units was found to be 18.7% (this CHP-MA derivative is hereinafter also referred to as "CHP-MA-18.7").

Example 10-3

Association Behavior of CHP-MA-2.4 in Aqueous Solution

The association behavior of CHP-MA-2.4 in water was detected by SEC-multi-angle light scattering (MALS). A TSKgel G4000SW column (Tosoh Corporation, Japan) and 50 mM NaCl-containing ultrapure water as an eluent were used for SEC, which was connected to MALS (DAWN DSP, Wyatt Technology) at a flow rate of 0.5 mL/minute. Assuming that the refractive index constant (dn/dc) was 0.143, the molecular weight, polydispersity and z-average root-mean-square radius of gyration (Rg) were determined. An aqueous solution of CHP-MA-2.4 was prepared at 1 mg/mL in ultrapure water, ultrasonicated with a probe sonicator (SONIFIER250, BRANSON) at 40W for 15 minutes and then filtered through a filter of 0.45 μm pore size before being provided for SEC-MALS measurement.

Example 11

Preparation of Hybrid Gel by Chemical Crosslinking Between CHP-MA and HA-SH

Example 11-1

Preparation of Hybrid Gel by Chemical Crosslinking Between CHP-MA and HA-SH (No. 1)

The HA-SH and CHP-MA derivatives used for each gel preparation (Samples 11-1 to 11-6) are show in Table 11, along with their final concentrations.

TABLE 11

Preparation conditions for chemical crosslinking between CHP-MA and HA-SH (No. 1)

| Sample | HA-SH | CHP-MA | Final conc. of HA-SH (mg/mL) | Final conc. of CHP-MA (mg/mL) |
|---|---|---|---|---|
| 11-1 | HA-SH-20k-18 | CHP-MA-2.4 | 10 | 30 |
| 11-2 | HA-SH-20k-18 | CHP-MA-2.4 | 20 | 20 |
| 11-3 | HA-SH-20k-18 | CHP-MA-18.7 | 10 | 30 |
| 11-4 | HA-SH-20k-18 | CHP-MA-18.7 | 20 | 20 |
| 11-5 | HA-SH-200k-27 | CHP-MA-2.4 | 10 | 30 |
| 11-6 | HA-SH-200k-27 | CHP-MA-2.4 | 20 | 20 |

Figure 11:
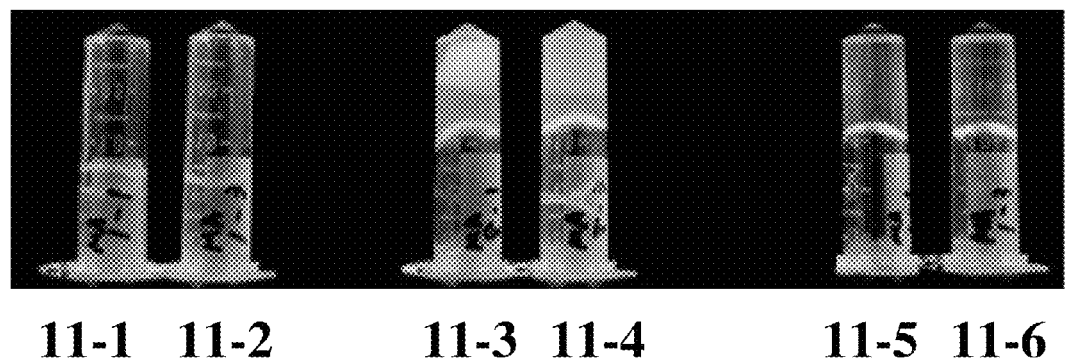
FIG. 11 is a photograph showing hybrid gels prepared by chemical crosslinking between CHP-MA and HA-SH.

HA-SH-20 k-18, HA-SH-200 k-27, CHP-MA-2.4 and CHP-MA-18.7 synthesized in Examples 9 and 10 were each mixed at 40 mg/mL with ultrapure water containing 20 mM tris(2-carboxyethyl)phosphine (TCEP), followed by stirring overnight to dissolve each derivative. These samples were introduced into centrifugal tubes. The final volume was set to around 1000 μL in all cases. Air bubbles generated during mixing were removed by centrifugation, and each tube was allowed to stand at 37° C. to cause a chemical crosslinking reaction. Gelling at each time point was confirmed by the Tilt method. FIG. 11 shows the appearance after 72 hours.

As a result, Sample 11-1 and Sample 11-2 were confirmed to have an increased viscosity after 24 hours, but caused no gelling when monitored until 72 hours. In Sample 11-3 and Sample 11-4, their viscosity was confirmed to increase after 10 hours, but phase separation was observed after 72 hours. Sample 11-5 and Sample 11-6 were confirmed to give gels without phase separation.

During the chemical crosslinking reaction in this example, two reactions appear to occur, i.e., Michael addition-induced crosslinking between MA and SH groups, as well as oxidation reaction between SH groups (disulfide bond formation). When HA-SH alone was tested under the same conditions to study whether gelling occurred, the viscosity was increased but no gelling was caused. This suggested that crosslinking was caused at least by Michael addition reaction, and thus indicated that CHP and HA would be chemically linked to each other in the hybrid gels of this example.

Example 11-2

Preparation of Hybrid Gel by Chemical Crosslinking Between CHP-MA and HA-SH (No. 2)

The HA-SH and CHP-MA derivatives used for each gel preparation (Samples 11-7 and 11-8) are shown in Table 12, along with their final concentrations.

TABLE 12

Preparation conditions for CHP-MA/HA-SH chemically crosslinked hybrid gels (No. 2)

| Sample | HA-SH | CHP-MA | Final conc. of HA-SH (mg/mL) | Final conc. of CHP-MA (mg/mL) |
|---|---|---|---|---|
| 11-7 | HA-SH-200k-27 | CHP-MA-18.7 | 10 | 30 |
| 11-8 | HA-SH-200k-27 | CHP-MA-18.7 | 20 | 20 |

HA-SH-200 k-27 and CHP-MA-18.7 synthesized in Examples 9 and 10 were each mixed at 40 mg/mL with ultrapure water containing 20 mM tris(2-carboxyethyl)phosphine (TCEP), followed by stirring overnight to dissolve each derivative. These samples were introduced into centrifugal tubes. Next, TEA was added at a final concentration of 100 mM. The final volume was set to around 1000 µL in all cases. Air bubbles generated during mixing were removed by centrifugation, and each tube was allowed to stand at 37° C. for 5 days to cause a chemical crosslinking reaction. After 5 days, each sample was turned into a gel without phase separation. To eliminate unreacted MA groups, mercaptoethanol was added in a 10-fold molar amount relative to the initial amount of MA groups, and reacted overnight. This reaction solution was removed and each gel was washed with an excessive amount of ultrapure water. To eliminate unreacted SH groups, iodoethanol was added in a 10-fold molar amount relative to the initial amount of SH groups, and further reacted overnight. This reaction solution was removed and each gel was washed with an excessive amount of ultrapure water and then lyophilized.

Example 12

Encapsulation of FITC-Labeled Insulin into Chemically Crosslinked CHP-MA/HA-SH Hybrid Gel The hybrid gel of Sample 11-4 prepared in Example 11 (5 mg) was swollen at equilibrium with 100 mM PB (pH 7.4). This was transferred to a UV cell and centrifuged at 1500 rpm for 1 minute to remove the supernatant. To this cell, 3 mL of a 50 µg/mL FITC-Ins-containing PB solution was added and allowed to stand at 20° C. The absorbance (492 nm) was measured over time between 0 hours and 24 hours to determine the amount of FITC-Ins incorporated into the HA-CHP hybrid gel from a calibration curve.

As a result, the incorporation of FITC-Ins into the hybrid gel was found to gradually proceed and to reach almost a plateau after 20 hours. The absorbance was decreased by 0.117, from which the amount of FITC-Inslin incorporated per unit weight of dry hybrid gel was calculated to be 0.775 nmol/mg (0.47% w/w).

Example 13

Figure 12:
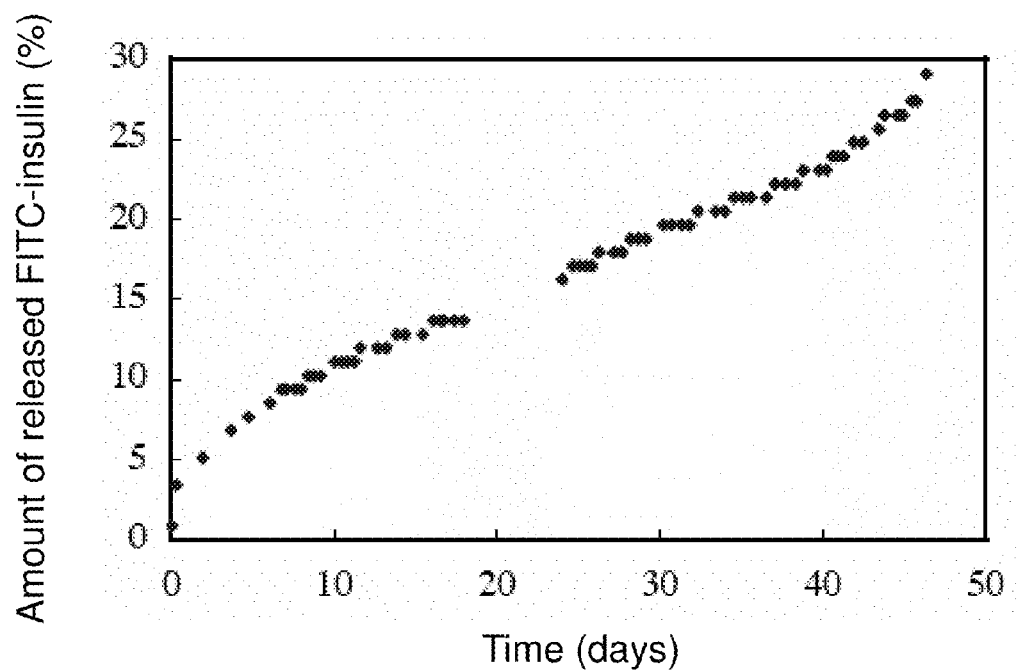
FIG. 12 is a graph showing the release property of FITC-Ins from a hybrid gel prepared by chemical crosslinking between CHP-MA and HA-SH.

Release Behavior of FITC-Labeled Insulin from Chemically Crosslinked CHP-MA/HA-SH Hybrid Gel The hybrid gel sample treated to incorporate the FITC-Ins solution in Example 12 was centrifuged and decanted to remove the supernatant, and then washed with 100 mM PB (pH 7.4, 3 mL, twice). To this sample, 3 mL of 100 mM PB (pH 7.4) was added, followed by monitoring at 20° C. at a wavelength of 492 nm with a UV-VIS spectrophotometer to evaluate the release behavior. The results obtained are show in FIG. 12.

This indicated that the chemically crosslinked CHP-MA/HA-SH hybrid gel of this example showed a reservoir-type sustained release profile with a very small initial burst of FITC-Ins release.

Example 14

Preparation of Chemically Crosslinked CHP-MA/HA-MA Hybrid Gel

Example 14-1

Synthesis of CHP-MA-2 and CHP-MA-7

Except that the amount of GMA was changed, the same procedure as used in Example 10 was repeated to synthesize CHP-MA derivatives whose introduction rate of MA groups relative to glucose units was 2.0% (hereinafter also referred to as "CHP-MA-2") and 7.0% (hereinafter also referred to as "CHP-MA-7").

Example 14-2

Study on Preparation Conditions for Chemically Crosslinked CHP-MA/HA-MA Hybrid Gel The CHP-MA and HA-MA derivatives used for each gel preparation (Samples 14-1 to 14-10) are shown in Table 13, along with their final concentrations.

TABLE 13

Preparation conditions for chemical crosslinking between CHP-MA and HA-MA (No. 1)

| Sample | HA-MA | CHP-MA | Final conc. of HA-MA (mg/mL) | Final conc. of CHP-MA (mg/mL) |
|---|---|---|---|---|
| 14-1 | HA-MA-200k-43 | CHP-MA-7 | 5 | 0 |
| 14-2 | HA-MA-200k-43 | CHP-MA-7 | 5 | 20 |
| 14-3 | HA-MA-200k-43 | CHP-MA-7 | 10 | 0 |
| 14-4 | HA-MA-200k-43 | CHP-MA-7 | 10 | 10 |
| 14-5 | HA-MA-200k-43 | CHP-MA-7 | 10 | 20 |
| 14-6 | HA-MA-200k-43 | CHP-MA-7 | 15 | 10 |
| 14-7 | HA-MA-200k-43 | CHP-MA-7 | 15 | 20 |
| 14-7 | HA-MA-200k-43 | CHP-MA-7 | 20 | 0 |
| 14-9 | HA-MA-200k-43 | CHP-MA-7 | 20 | 10 |
| 14-10 | HA-MA-200k-43 | CHP-MA-7 | 20 | 20 |

Figure 13:
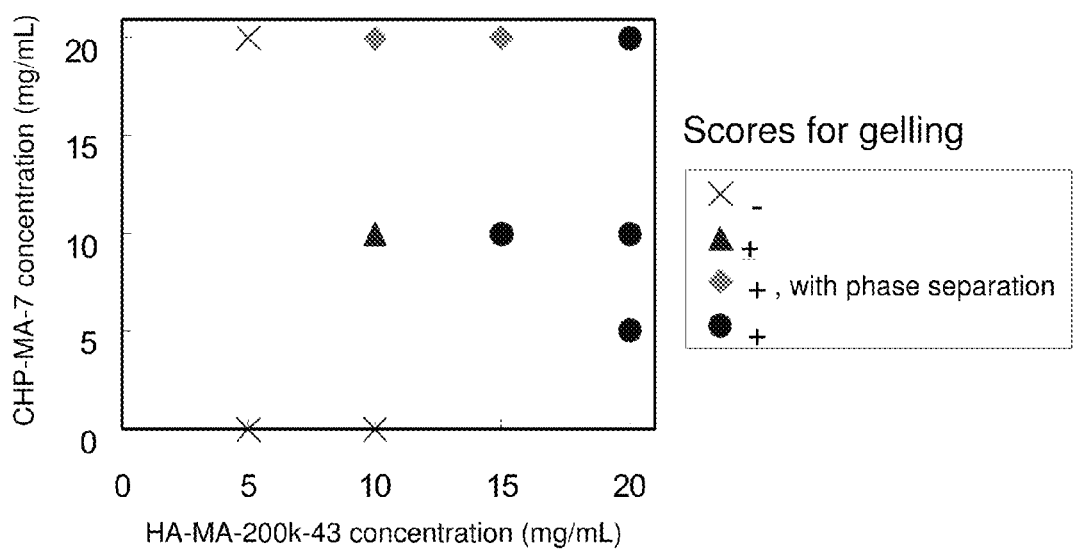
FIG. 13 shows the results of hybrid gel preparation by chemical crosslinking between CHP-MA and HA-MA.

HA-MA-9 synthesized in Example 1 (also referred to as "HA-MA-200 k-43") and CHP-MA-7 synthesized in Example 14-1 were each dissolved at 40 mg/mL in ultrapure water. After these two polymer solutions were mixed to give the composition indicated in Table 13, TEA was added and mixed well at a final concentration of 100 mM. Further, an aqueous DTT solution was added in a ½ molar amount relative to the final concentration of MA groups in the system (at a ratio of MA group:SH group=1:1) and mixed well. The final volume was set to around 1000 µL in all cases. Air bubbles generated during mixing were removed by centrifugation, and each mixture was allowed to stand at 37° C. for 24 hours to cause a chemical crosslinking reaction, followed by the Tilt method for determination of gelling. The results (diagram) obtained are shown in FIG. 13.

As a result, gelling was found to proceed with increases in the total MA groups contained in the system. As seen from the results of Samples 14-3 to 14-5, when the nanogel was added under conditions of 10 mg/mL HA-MA where HA-MA alone was not gelled, the viscosity was found to increase at a nanogel content of 10 mg/mL and gelling was confirmed upon addition of 20 mg/mL nanogel. This indicated that MA groups in the nanogel would contribute to gelling. These gelling events were each confirmed within 2 hours after initiation of the reaction. When these gels were swollen in ultrapure water immediately after preparation, transparent gels were obtained even in the case of Sample 14-5 and Sample 14-7 which were non-transparent gels due to phase separation occurring immediately after gelling. Moreover, the same study was also performed using CHP-MA-2, and almost the same gelling behavior was observed.

Example 14-3

Preparation of Chemically Crosslinked CHP-MA/HA-MA Hybrid Gel

The CHP-MA and HA-MA derivatives used for each gel preparation (Samples 14-11 to 14-14) are shown in Table 14, along with their final concentrations. After gelling was induced in the same manner as used in Example 14-2, mercaptoethanol was added and reacted in an excessive amount relative to the initial MA groups in the system to thereby eliminate possible unreacted MA groups remaining in the system. Each sample was further washed with an excessive amount of ultrapure water to remove the excess of mercaptoethanol, and lyophilized before being provided for the next example.

TABLE 14

Preparation conditions for chemical crosslinking between CHP-MA and HA-MA (No. 2)

| Sample | HA-MA | CHP-MA | Final conc. of HA-MA (mg/mL) | Final conc. of CHP-MA (mg/mL) |
| --- | --- | --- | --- | --- |
| 14-11 | HA-MA-200k-43 | CHP-MA-2 | 20 | 5 |
| 14-12 | HA-MA-200k-43 | CHP-MA-2 | 20 | 20 |
| 14-13 | HA-MA-200k-43 | CHP-MA-7 | 20 | 5 |
| 14-14 | HA-MA-200k-43 | CHP-MA-7 | 20 | 20 |

Example 15

Encapsulation of FITC-Ins into CHP-MA/HA-MA Chemically Crosslinked Hybrid Gel

Figure 14:
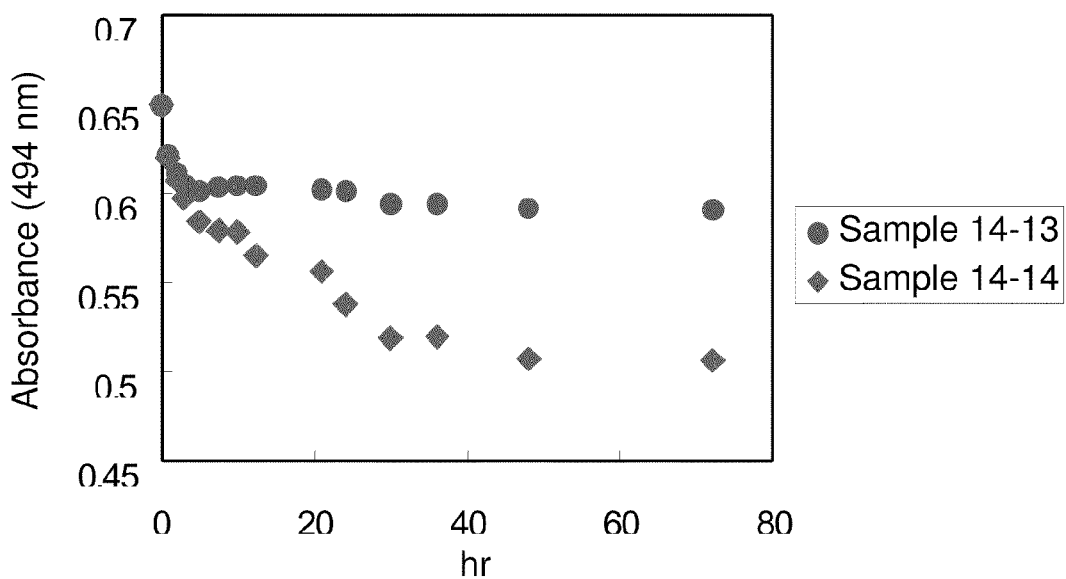
FIG. 14 is a graph showing the time course of changes in the amount of FITC-Ins absorbed into hybrid gels prepared by chemical crosslinking between CHP-MA and HA-MA.

To the hybrid gels of Samples 14-11 to 14-14 prepared in Example 14-3 (5 mg), 5 mL of 100 mM PB (pH 7.4) containing 50 μg/mL FITC-Ins was added and allowed to stand at 20° C. The absorbance (494 nm) was measured over time between 0 hours and 72 hours. FIG. 14 shows the time course of changes in the absorbance of Sample 14-13 and Sample 14-14.

As a result, the incorporation of FITC-Ins into the hybrid gels was found to spontaneously proceed when simply added, and to reach almost a plateau after 72 hours. The amount of FITC-Ins incorporated into each hybrid gel after 72 hours was determined from a calibration curve. The results obtained are shown in Table 15.

TABLE 15

Amount of FITC-Ins encapsulated into chemically crosslinked CHP-MA/HA-MA hybrid gels

| Sample | Final conc. of HA-MA (mg/mL) | Final conc. of CHP-MA (mg/mL) | Introduction rate of MA in CHP-MA (%) | Amount of encapsulated FITC-Ins relative to dry hybrid gel (nmol/mg) | (% w/w) |
| --- | --- | --- | --- | --- | --- |
| 14-11 | 20 | 5 | 2 | 0.9 | 0.55 |
| 14-12 | 20 | 20 | 2 | 1.9 | 1.16 |
| 14-13 | 20 | 5 | 7 | 0.9 | 0.55 |
| 14-14 | 20 | 20 | 7 | 1.8 | 1.10 |

The amount of encapsulated FITC-Ins was found to increase at higher nanogel contents, but did not depend on the substitution degree of MA groups. This suggested that the nanogel content contributed to an increase or decrease in FITC-Ins incorporation.

Example 16

Release Behavior of FITC-Ins from Chemically Crosslinked CHP-MA/HA-MA Hybrid Gel Example 16-1

Release Property in Buffer

Figure 15:
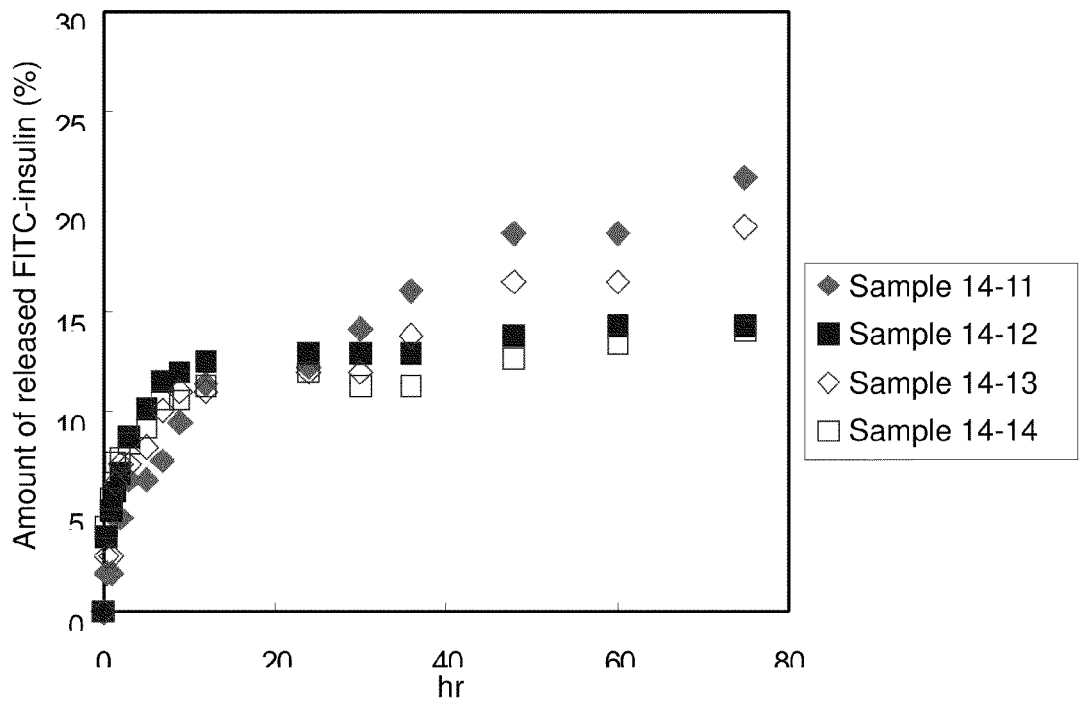
FIG. 15 is a graph showing the time course of changes in the amount of FITC-Ins released from hybrid gels prepared by chemical crosslinking between CHP-MA and HA-MA.

The hybrid gel samples prepared to incorporate the FITC-Ins solution in Example 15 were centrifuged and decanted to remove the supernatant, and then washed with 100 mM PB (pH 7.4, 3 mL, twice). To each sample, 3 mL of 100 mM PB (pH 7.4) was added, followed by monitoring at 37° C. at a wavelength of 494 nm with a UV-VIS spectrophotometer to measure the time course of changes in release. The results obtained are shown in FIG. 15.

The results indicated that all the gels continuously released FITC-Ins until about 3 days. The delayed release phase observed at 12 hours or later after initiation of the release showed a lower release rate at a higher substituent introduction rate in CHP-MA or at a higher nanogel content, thus suggesting that the sustained release rate can be controlled by the substituent introduction rate or the nanogel content.

Example 16-2

Release Behavior in the Presence of Cyclodextrin

Figure 16:
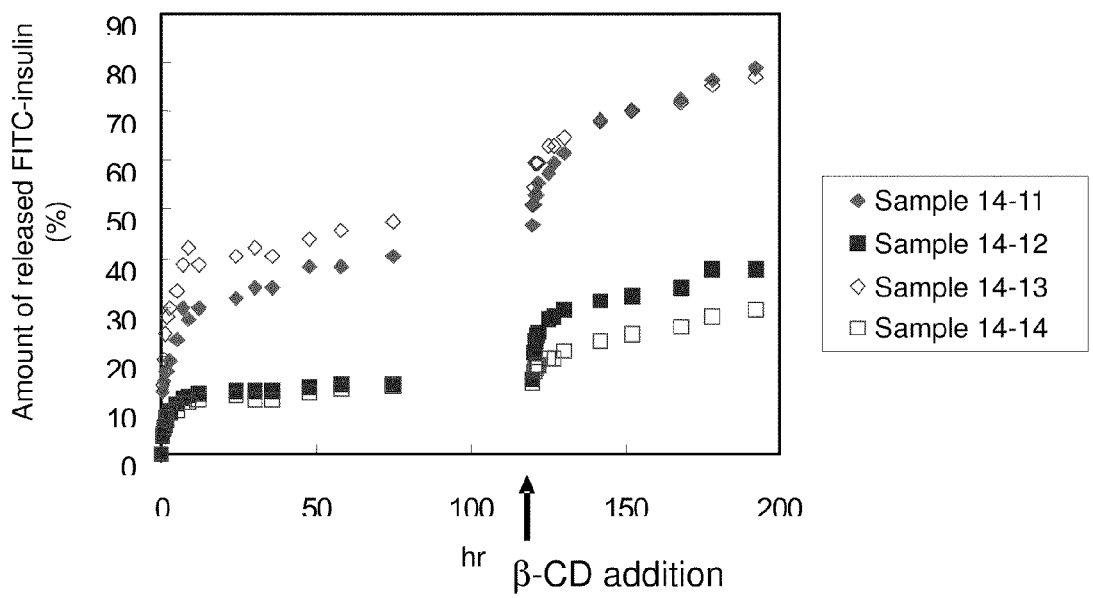
FIG. 16 is a graph showing the effect of cyclodextrin on the release behavior of FITC-Ins from hybrid gels prepared by chemical crosslinking between CHP-MA and HA-MA.

Hybrid gel samples were prepared and treated to incorporate an FITC-Ins solution in the same manner as used in Example 15, and evaluated for their release behavior in the same manner as shown in Example 16-1, except that washing was performed once. Moreover, at days after initiation of the release, β-CD was added at 10 mM for further evaluation of the release behavior. The results obtained are shown in FIG. 16.

First, when compare to the sample which was washed twice (Example 16-1), Sample 14-11 and Sample 14-13 with low CHP content showed about a 30% increase in the initial burst, whereas Sample 14-12 and Sample 14-14 with high CHP content showed little change in the initial burst. This suggested that the hybrid gels with low nanogel content had a high percentage of FITC-Ins encapsulated within the HA matrix. As in the case of the results obtained for the CHP-encapsulating chemically crosslinked HA-MA hybrid gels in Example 5 or 7, addition of cyclodextrin accelerated the release rate, thus suggesting that FITC-Ins was held in the hybrid gels by hydrophobic interaction with cholesterol groups.

Example 16-3

Release Property in the Presence of Albumin

Figure 17:
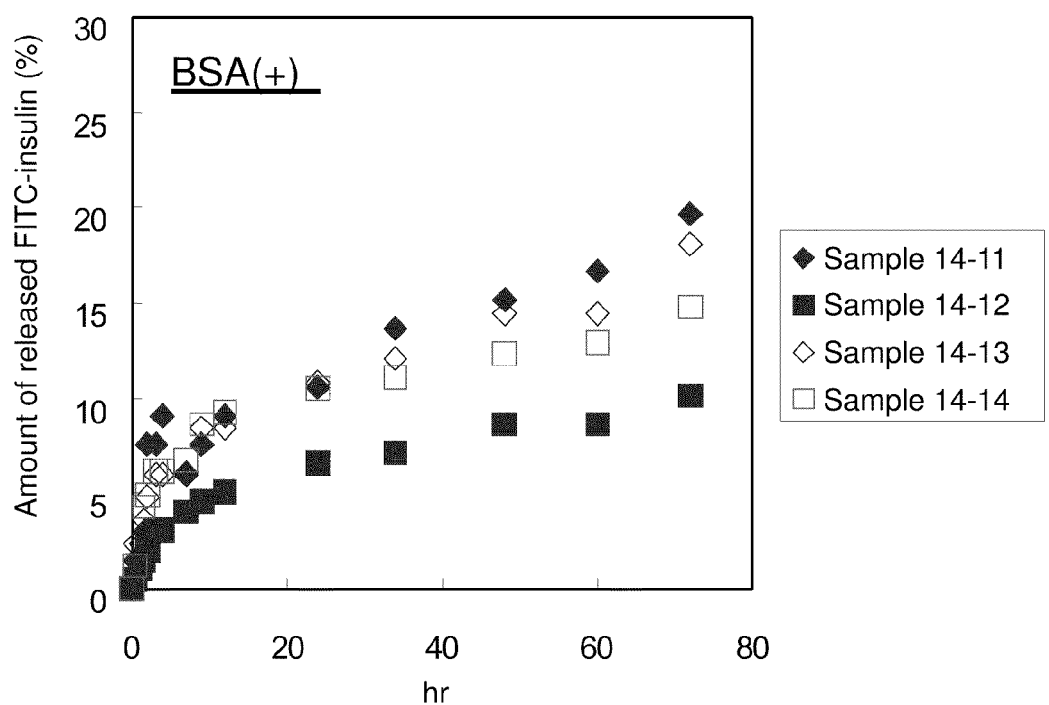
FIG. 17 is a graph showing the effect of albumin on the release behavior of FITC-Ins from hybrid gels prepared by chemical crosslinking between CHP-MA and HA-MA.

Hybrid gel samples were prepared and treated to incorporate an FITC-Ins solution in the same manner as used in Example 15, and evaluated for their release behavior in the same manner as shown in Example 16-1, except that the release buffer was replaced by 100 mM PB (pH 7.4) containing 50 mg/mL BSA. The results obtained are shown in FIG. 17.

As a result, the release rate of FITC-Ins showed little change until 24 hours, regardless of the composition of gels, when compared to the absence of BSA (Example 16-1). This would be due to the effect of chemically crosslinked HA gels, as in the case of the results obtained for CHP-encapsulating hybrid gels (Example 8). Since an albumin concentration of 50 mg/mL is substantially equal to its concentration in blood, the same release property as in buffer can also be expected in blood.

Example 16-4

Release Property in the Presence of Hyaluronidase

Figure 18:
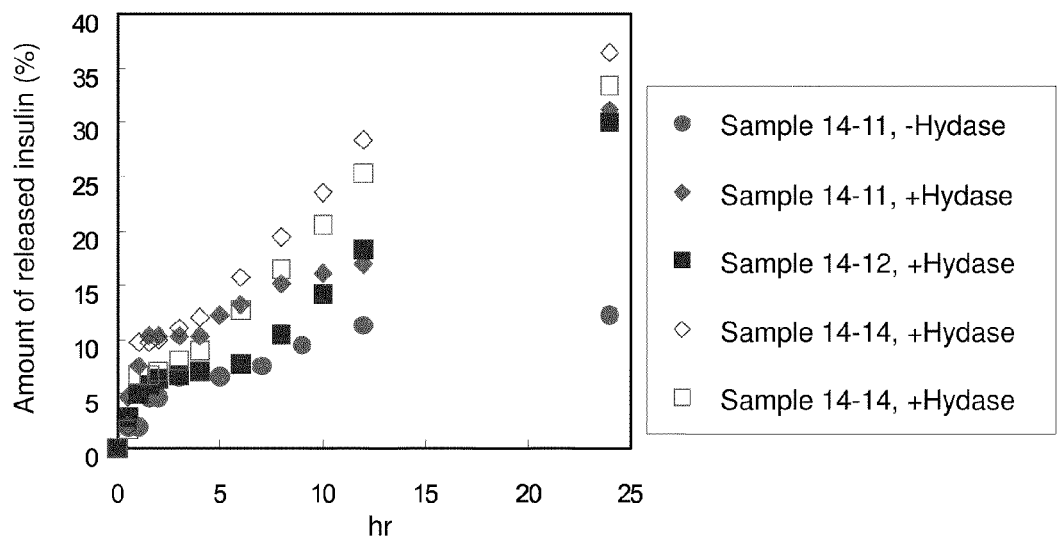
FIG. 18 is a graph showing the effect of hyaluronidase on the release behavior of FITC-Ins from hybrid gels prepared by chemical crosslinking between CHP-MA and HA-MA.

Hybrid gel samples were prepared and treated to incorporate an FITC-Ins solution in the same manner as used in Example 15, and evaluated for their release behavior in the same manner as shown in Example 16-1, except that the release buffer was replaced by 100 mM PB (pH 6.2) containing 285 mU/mL hyaluronidase SD and 50 mg/mL BSA. The results obtained are shown in FIG. 18.

As a result, the release rate of FITC-Ins was accelerated until 24 hours when compared to the absence of hyaluronidase SD (Example 16-1). This suggested that drug release was caused by degradation of the hybrid gels (degradation of chemically crosslinked HA moieties), as in the case of the results obtained for CHP-encapsulating hybrid gels (Example 5).

Comparative Example 2

Preparation of Chemically Crosslinked CHP-MA/MPC Hybrid Gel and Evaluation on Drug Release Profile Comparative Example 2-1

Preparation of Chemically Crosslinked CHP-MA/MPC Hybrid Gel

CHP-MA-7 synthesized in Example 14 and 2-methacryloyloxyethyl phosphorylcholine (MPC) were dissolved in ultrapure water at 30 mg/mL and 32 mg/mL, respectively, followed by addition of 2,2'-azobis[2-(2-imidazolin-2-yl)propane] (VA-044, Wako Pure Chemical Industries, Ltd., Japan) in a 0.005-fold molar amount relative to MA groups in the system. After argon degassing, polymerization reaction was performed at 50° C. for 5 hours. The resulting hybrid gel was purified by being swollen in an excessive amount of water for 1 week, and then lyophilized to give a white solid.

The hybrid gel prepared in this comparative example is hereinafter also referred to as "Sample C-2."

Comparative Example 2-2

Encapsulation of FITC-Ins into Hybrid Gel

Except that the hybrid gel prepared in Comparative Example 2-1 (10 mg) was used, the same procedure as shown in Example 15 was repeated to encapsulate FITC-Ins.

Example 17

Comparison of Swelling Degree and Drug Release Profile in Various Hybrid Gels

Example 17-1

Evaluation on Swelling Degree of Lyophilized Hybrid Gel

Figure 19:
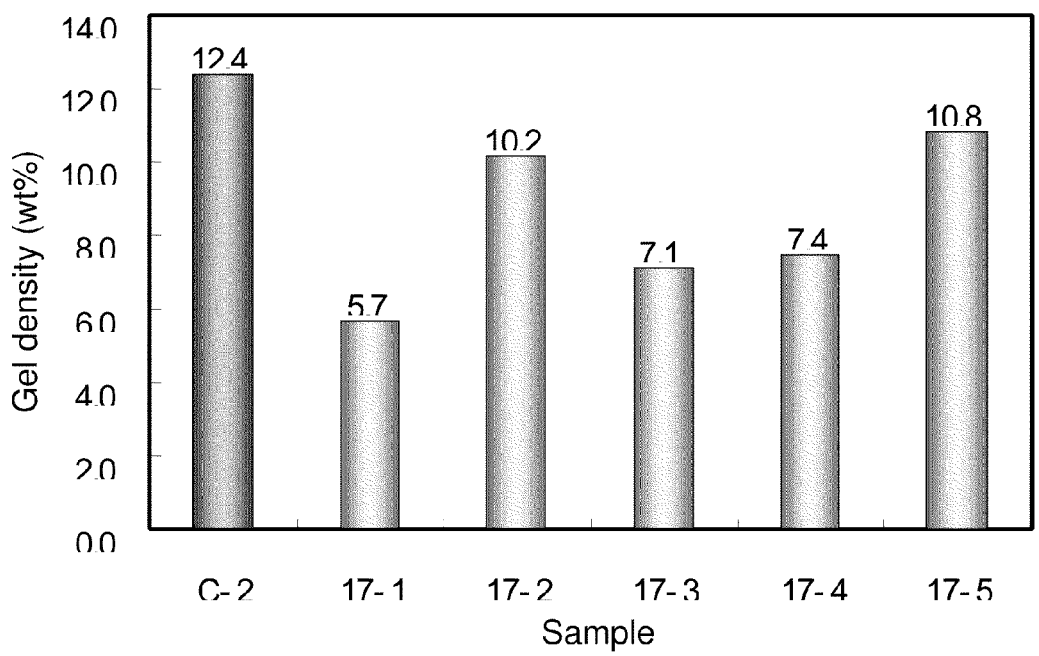
FIG. 19 is a graph showing the gel density of various chemically crosslinked hybrid gels.

Under the same conditions as used for Sample 8-2 in Example 8-1, a hybrid gel of Sample 17-1 was prepared and lyophilized (shown in Table 16). In addition, under the same conditions as used for Samples 14-11 to 14-14 in Example 14-3, hybrid gels of Samples 17-2 to 17-5 (shown in Table 17) were prepared and lyophilized. Samples 17-1 to 17-5 and Sample C-2 were tested as follows: the lyophilized hybrid gels were each weighed in an amount of about 5 to 10 mg (dry weight), swollen in an excessive amount of PBS (pH 7.4) at 4° C. for 24 hours, decanted to remove the solvent, treated with Kimwipes® to remove water on their surface, and measured for their weight (weight in the swollen state), followed by calculating the gel density in the swollen state in PBS according to formula (1) mentioned above. The results obtained are shown in graphic form in FIG. 19.

TABLE 16

Preparation conditions for CHP-encapsulating chemically crosslinked HA-MA hybrid gel (No. 5)

| Sample | HA-MA | Molecular weight of HA (kDa) | Introduction rate of MA (unit %) | Final conc. of HA-MA (mg/mL) | Final conc. of CHP (mg/mL) |
|---|---|---|---|---|---|
| 17-1 | HA-MA-2 | 16 | 33.6 | 50 | 20 |

TABLE 17

Preparation conditions for chemical crosslinking between CHP-MA and HA-MA (No. 3)

| Sample | HA-MA | CHP-MA | Final conc. of HA-MA (mg/mL) | Final conc. of CHP-MA (mg/mL) |
|---|---|---|---|---|
| 17-2 | HA-MA-200k-43 | CHP-MA-2 | 20 | 5 |
| 17-3 | HA-MA-200k-43 | CHP-MA-2 | 20 | 20 |
| 17-4 | HA-MA-200k-43 | CHP-MA-7 | 20 | 5 |
| 17-5 | HA-MA-200k-43 | CHP-MA-7 | 20 | 20 |

Example 17-2

Figure 20:
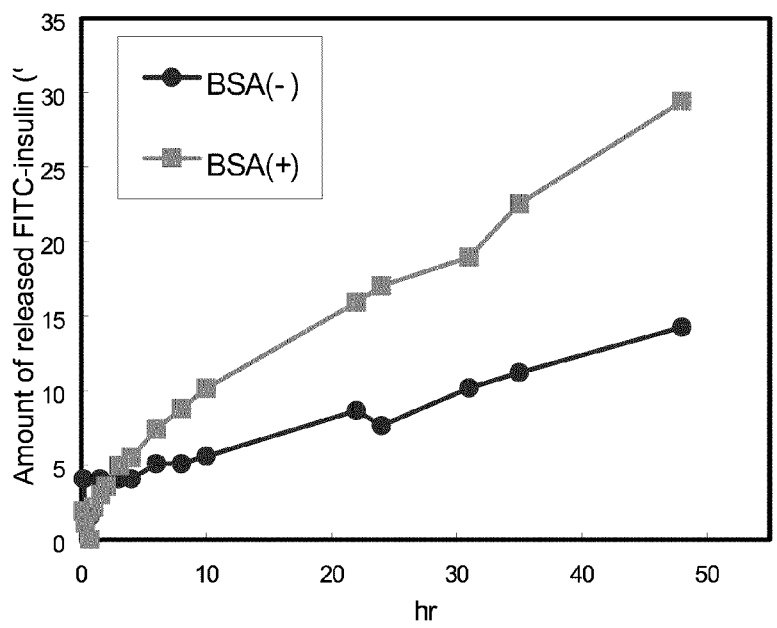
FIG. 20 is a graph showing the effect of albumin (10 mg/mL) on the release behavior of FITC-Ins from hybrid gels prepared by chemical crosslinking between CHP-MA and MPC.
Figure 21:
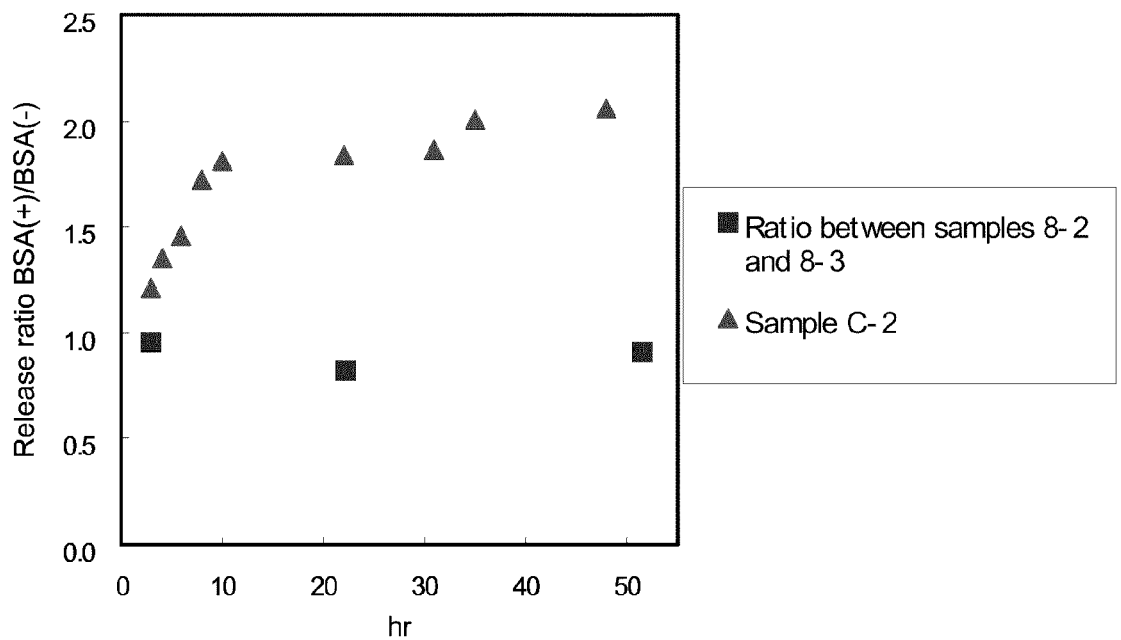
FIG. 21 is a graph showing the effect of albumin on the release behavior of FITC-Ins compared between CHP-MA/MPC hybrid gel and CHP-MA-encapsulating chemically crosslinked HA-MA hybrid gel.

Comparison of Drug Release Profile Between CHP-Encapsulating Chemically Crosslinked HA-MA Hybrid Gel and Chemically Crosslinked CHP-MA/MPC Hybrid Gel The FITC-Ins-encapsulating CHP-MA/MPC hybrid gel prepared in Comparative Example 2-2 was evaluated for its drug release profile in a release buffer free from BSA (BSA (−)) or containing 10 mg/mL BSA (BSA(+)) in the same manner as shown in Examples 16-1 and 16-3, except for the BSA concentration. The results obtained are shown in FIG. 20. In addition, based on this result and the release behavior of FITC-Ins tested in Example 8-3, the ratio of the release amount in the presence of BSA to the release amount in the absence of BSA (BSA(+)/BSA(−)) is plotted against time in FIG. 21.

Example 17-3

Figure 22:
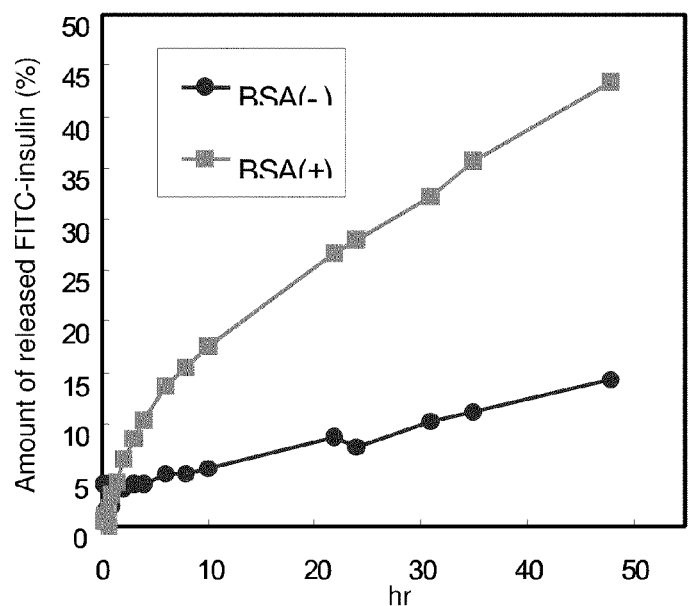
FIG. 22 is a graph showing the effect of albumin (50 mg/mL) on the release behavior of FITC-Ins from hybrid gels prepared by chemical crosslinking between HP-MA and MPC.
Figure 23:
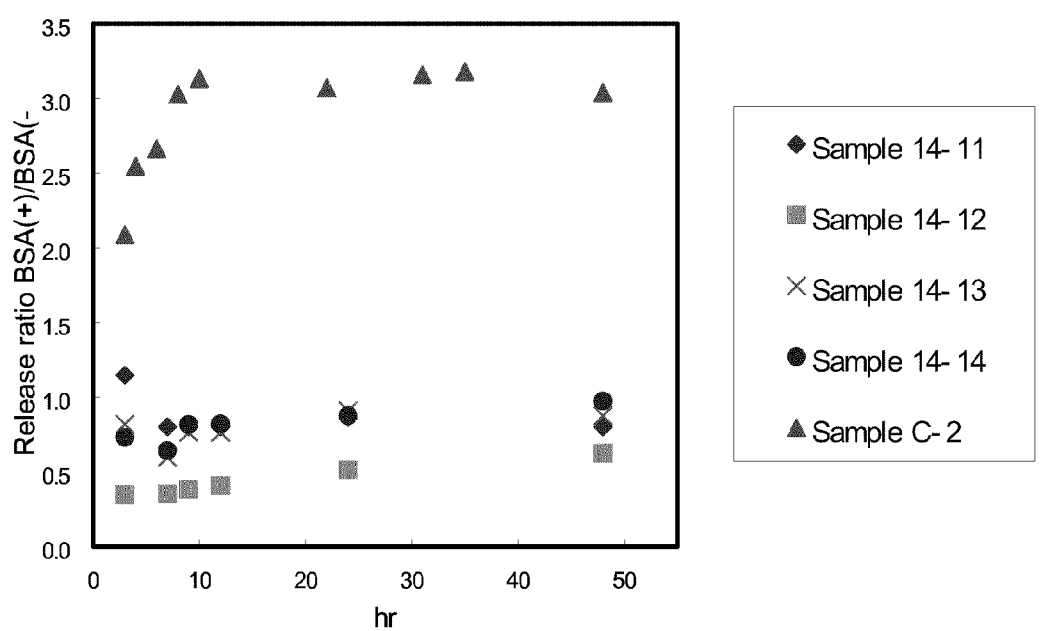
FIG. 23 is a graph showing the effect of albumin on the release behavior of FITC-Ins compared between CHP-MA/MPC hybrid gel and chemically crosslinked CHP-MA/HA-MA hybrid gels.

Comparison of Drug Release Profile Between Chemically Crosslinked CHP-MA/HA-MA Hybrid Gel and Chemically Crosslinked CHP-MA/MPC Hybrid Gel The FITC-Ins-encapsulating CHP-MA/MPC hybrid gel prepared in Comparative Example 2-2 was evaluated for its drug release profile in a release buffer free from BSA (BSA (−)) or containing BSA (BSA(+)) in the same manner as shown in Examples 16-1 and 16-3. The results obtained are shown in FIG. 22. In addition, based on this result and the release behavior of FITC-Ins tested in Example 16, the of ratio the release amount in the presence of BSA to the release amount in the absence of BSA (BSA(+)/BSA(−)) is plotted against time in FIG. 23.

In the CHP-encapsulating chemically crosslinked HA-MA hybrid gels and chemically crosslinked CHP-MA/HA-MA hybrid gels used in this example, their gel density in the swollen state was lower than that of Sample C-2, but the albumin-induced acceleration of the drug release rate was significantly inhibited.

Example 18

Synthesis of AM Group-Introduced HA Derivative (HA-AM)

Using hyaluronic acid sodium salt having a molecular weight of 21 kDa or 27 kDa (Shiseido Co., Ltd., Japan), HA-TBA was prepared in the same manner as used in Example 1-2 and dissolved at 5 mg/mL in anhydrous DMSO. Then, 2,2'-(ethylenedioxy)bis(ethylamine) (EDOBEA, Aldrich) was added to each solution in a 50-fold molar amount relative to HA units. Next, BOP reagent was added in a 0.4-fold molar amount relative to HA units and reacted overnight with mild stirring at room temperature. The reaction solution was purified by being dialyzed against 0.3M aqueous NaCl (SpectraPor 4, molecular weight cutoff (MWCO): 12 k-14 kDa, with 4 replacements of the external solution) and further against ultrapure water (with 6 replacements of the external solution). The resulting dialysate was lyophilized to give HA-AM as a white solid.

HA-AM thus obtained was dissolved in $D_2O$ at a concentration of about 10 mg/mL, followed by NMR structural analysis to calculate the introduction rate of AM groups relative to HA units (calculated from the ratio of the integrated value for methylene in EDOBEA ($NH_2$—$\underline{CH_2}$—($CH_2$—O—$CH_2$)$_2$—$\underline{CH_2}$—NH—) at around 3.22 ppm, based on the integrated value for acetyl group in glucosamine). The introduction rate was used to calculate the unit average molecular weight of HA-AM (calculated as sodium salt for unmodified HA unit and as hydrochloride salt for HA-AM unit) (see Table 18).

TABLE 18

Preparation conditions and properties of HA-AM

| Abbreviation | Molecular weight of HA (kDa) | Added molar ratio of EDOBEA and BOP (HA unit/BOP/EDOBEA) | Introduction rate of AM (unit %) | Unit average molecular weight of HA-AM |
|---|---|---|---|---|
| HA-AM-1 | 21 | 1/0.4/50 | 28.0 | 441.8 |
| HA-AM-2 | 27 | 1/0.4/50 | 17.6 | 426.8 |
| HA-AM-3 | 27 | 1/0.4/50 | 28.2 | 442.1 |

Example 19

Synthesis of SH Group (Iminothiolane, ITL)-Introduced HA Derivative (HA-ITL)

HA-AM-2 obtained in Example 18 was dissolved at 10 mg/mL in 100 mM PB (pH 7.4). Then, 2-iminothiolane hydrochloride (Pierce) was added in a 0.35-fold molar amount relative to HA units and reacted with mild stirring at room temperature for 2 hours. Next, succinic (SUC) anhydride was added in a 40-fold molar amount relative to HA units and reacted at room temperature for 2 hours. The reaction solution was purified by being dialyzed against 0.3M aqueous NaCl (SpectraPor 4, molecular weight cutoff (MWCO): 12 k-14 kDa, with 4 replacements of the external solution), against ultrapure water (with 6 replacements of the external solution) and further against 1 mM aqueous hydrochloric acid (with 3 replacements of the external solution). The resulting dialysate was lyophilized to give HA-ITL as a white solid.

HA-ITL thus obtained was dissolved in $D_2O$ at a concentration of about 10 mg/mL, followed by NMR structural analysis to calculate the introduction rates of ITL and SUC groups relative to HA units (calculated from the ratio of the integrated value for methylene in ITL (SH—$CH_2$—$\underline{CH_2}$—$CH_2$—C(=$NH_2^+$)—) at around 2.40 ppm and the ratio of the integrated value for ethylene in SUC(COOH—$\underline{CH_2}$—$\underline{CH_2}$—CO—) at around 2.70 ppm, based on the integrated value for acetyl group in glucosamine). The introduction rates were used to calculate the unit average molecular weight of HA-ITL (calculated as free carboxylic acid for unmodified HA unit, as free carboxylic acid for HA-AM-SUC unit, and as hydrochloride salt for imino group in HA-AM-ITL unit) (see Table 19).

TABLE 19

Preparation conditions and properties of HA-ITL

| Abbreviation | Molecular weight of HA (kDa) | Added molar ratio of ITL and SUC anhydride (HA unit/ITL/SUC) | Introduction rate of TIL (unit %) | Unit average molecular weight of HA-ITL |
|---|---|---|---|---|
| HA-ITL | 27 | 1/0.35/40 | 16.7 | 425.9 |

Example 20

Synthesis of SH Group (Thioglycolic Acid, TGA)-Introduced HA Derivative (HA-TGA)

Example 20-1

Introduction of SATA Groups into HA-AM

HA-AM-3 obtained in Example 18 was dissolved at 10 mg/mL in 100 mM PB (pH 7.4). Then, N-succinimidyl S-acetylthioacetate (SATA) (Pierce) was added in a 3-fold molar amount relative to AM group-introduced HA units (in a 0.85-fold molar amount relative to HA units) and reacted with mild stirring at room temperature for 2 hours. Next, succinic (SUC) anhydride was added in an amount of 40-fold equivalents relative to HA units and reacted at room temperature for 2 hours. The reaction solution was purified by being dialyzed against 0.3M aqueous NaCl (SpectraPor 4, molecular weight cutoff (MWCO): 12 k-14 kDa, with 4 replacements of the external solution) and further against ultrapure water (with 6 replacements of the external solution). The resulting dialysate was lyophilized to give a SATA-introduced HA derivative (HA-SATA) as a white solid.

Example 20-2

Synthesis of HA-TGA by Deprotection of S-Acetyl Groups

All solvents used in this example were bubbled with nitrogen before being provided for the following study.

The white powder of HA-SATA obtained in Example 20-1 was dissolved at a concentration of 10 mg/mL in 50 mM aqueous hydrochloric acid (pH 7.0) containing 500 mM hydroxyamine ($NH_2$—OH) and 10 mM TCEP, and stirred at room temperature for 1 hour. For purification purposes, the resulting solution was applied to a desalting column (PD-10, GE Healthcare Biosciences) which had been equilibrated with 1 mM aqueous hydrochloric acid, and the collected solution was dialyzed against 1 mM aqueous hydrochloric acid (SpectraPor 4, molecular weight cutoff (MWCO): 12 k-14 kDa, with two replacements of the external solution). The resulting dialysate was lyophilized to give a TGA-introduced HA derivative (HA-TGA) as a white solid.

HA-TGA thus obtained was dissolved in $D_2O$ at a concentration of about 10 mg/mL, followed by NMR structural analysis to calculate the introduction rates of TGA and SUC groups relative to HA units (calculated from the ratio of the integrated value for methylene adjacent to SH group in TGA (SH—$\underline{CH_2}$—CO—) at around 3.26 ppm and the ratio of the integrated value for ethylene in SUC(COOH—$\underline{CH_2}$—$\underline{CH_2}$—CO—) at around 2.70 ppm, based on the integrated value for acetyl group in glucosamine). The introduction rates were used to calculate the unit average molecular weight of HA-TGA (calculated as free carboxylic acid for unmodified HA unit and as free carboxylic acid for HA-AM-SUC unit) (see Table 20).

TABLE 20

Preparation conditions and properties of HA-TGA

| Abbreviation | Molecular weight of HA (kDa) | Added molar ratio of SATA and SUC anhydride (HA unit/SATA/SUC) | Introduction rate of TGA (unit %) | Unit average molecular weight of HA-TGA |
|---|---|---|---|---|
| HA-TGA | 27 | 1/0.85/40 | 21.0 | 438.7 |

Example 21

Synthesis of SH Group (Dithiothreitol, DTT)-Introduced HA Derivative (HA-DTT)

Example 21-1

Synthesis of HA-MA

Under the same conditions as used for HA-MA-2 to HA-MA-4 in Example 1, HA-MA was synthesized. The introduction rate of MA groups was 35.2% and the unit average molecular weight was 432.7.

The HA-MA derivative synthesized in this example is hereinafter also referred to as HA-MA-11.

Example 21-2

Synthesis of HA-DTT

All solvents used in this example were bubbled with nitrogen before being provided for the following study.

The HA-MA derivative obtained in Example 21-1 was dissolved in ultrapure water at a concentration of 20 mg/mL. To this solution, TEA, ultrapure water and DTT were successively added in this order to give final concentrations of 5 mg/mL for HA-MA, 10 mM for TEA and 25-fold molar excess for DTT (relative to MA groups), followed by reaction overnight at room temperature. The resulting solution was applied to a desalting column (PD-10, GE Healthcare Biosciences) which had been equilibrated with 1 mM aqueous hydrochloric acid. To the collected solution, TCEP was added at 10 mM and reacted at room temperature for 1 hour. Purification with a desalting column was repeated again, followed by dialysis against 1 mM aqueous hydrochloric acid (SpectraPor 4, molecular weight cutoff (MWCO): 12 k-14 kDa, with two replacements of the external solution). The resulting dialysate was lyophilized to give a DTT-introduced HA derivative (HA-DTT) as a white solid.

HA-DTT thus obtained was dissolved in $D_2O$ at a concentration of about 10 mg/mL, followed by NMR structural analysis. As a result of the reaction, peaks (1.91 ppm, 5.73 ppm and 6.13 ppm) arising from MA groups in HA-MA disappeared, suggesting that there remained no unreacted MA group and all MA groups were reacted with SH groups in DTT by Michael addition. On the other hand, the several overlapped peaks detected between 2.69 ppm and 2.86 ppm were assigned to methylenes adjacent to SH groups in DTT (4H/DTT group), methylene derived from MA groups receiving the addition reaction (DTT-CH$_2$—CH(CH$_3$)—COO—) and methine derived from these MA groups (DTT-CH$_2$—CH(CH$_3$)—COO—). Based on the ratio between the sum of these integrated values (7H/MA-DTT group) and the integrated value for methyl derived from MA groups receiving the addition reaction (1.23 ppm, DTT-CH$_2$—CH(CH$_3$)—COO—), it was inferred that DTT was introduced without being either too much or too little relative to MA groups. In view of the foregoing, assuming that the introduction rate of DTT groups relative to HA units was the same as the introduction rate of MA groups in HA-MA-11, the unit average molecular weight of HA-DTT was calculated (unmodified HA unit was calculated as free carboxylic acid) (see Table 21).

TABLE 21

Preparation conditions and properties of HA-DTT

| Abbreviation | Molecular weight of HA (kDa) | Added molar ratio of DTT (HA unit/ MA unit/DTT) | Introduction rate of DTT (unit %) | Unit average molecular weight of HA-DTT |
|---|---|---|---|---|
| HA-DTT | 16 | 1/0.35/8.8 | 35.2 | 481.7 |

Example 22

Synthesis of Cholesterol Group-Introduced Cluster Dextrin Derivative (CHcDex)

Cluster Dextrin (cDex) having a molecular weight of 150 kDa (purchased from Ezaki Glico Co., Ltd., Japan) was dissolved at 100 mg/mL in anhydrous DMSO. Then, cholesteryl-N-(6-isocyanatohexyl)carbamate (CHI) (purchased from NOF Corporation, Japan) dissolved in anhydrous pyridine was added in a 0.05-fold molar amount relative to cDex units and reacted under a nitrogen atmosphere at 80° C. for 9.5 hours. The reaction solution was applied to an excessive amount of an ethanol/diethyl ether mixture (3:17 by volume) to give a white precipitate by reprecipitation. The resulting precipitate was dried under reduced pressure, dissolved in DMSO and then purified by dialysis against ultrapure water (SpectraPor 6, molecular weight cutoff (MWCO): 3.5 kDa, with 6 replacements of the external solution). The resulting dialysate was filtered through a filter (0.8 μm) and then lyophilized to give CHcDex as a white solid.

CHcDex thus obtained was dissolved in a DMSO-d$_6$/D$_2$O mixture (9:1 by volume), followed by NMR structural analysis to calculate the introduction rate of cholesterol groups relative to cDex units (calculated from the ratio of the integrated value for peaks (around 0.2-2.4 ppm) arising from cholesterol, based on the integrated value for anomeric protons (around 4.9-5.3 ppm) derived from α1-4 linkages contained at 94% in cDex). The introduction rate was 3.8 cholesterol groups per 100 glucose units.

Comparative Example 3

Preparation of Various Chemically Crosslinked HA Gels

The HA derivatives used for each sample preparation (Samples C3-1 to C3-11) are shown in Table 22, along with their final concentrations, crosslinking agents, reaction conditions and so on.

Comparative Example 3-1

Preparation of HA Gel in which HA-MA is Crosslinked by Michael Addition Reaction Except that the buffer for gelling reaction was replaced by 500 mM TEA/100 mM aqueous hydrochloric acid (final concentration: ⅕, pH after dilution: 8.1), the same procedure as shown in Example 2 was repeated to prepare the chemically crosslinked HA gels of Samples C3-1 to C3-3 indicated in Table 22, followed by calculating the gel density in the swollen state for each sample.

Comparative Example 3-2

Preparation of HA Gel in which HA-MA is Crosslinked by Radical Polymerization

In 500 mM aqueous hydrochloric acid, N,N,N',N'-tetramethylethylenediamine (TEMED) was dissolved at 500 mM. When this solution was diluted to ⅕ with ultrapure water, the solution pH was 7.3.

In ultrapure water, potassium peroxodisulfate (KPS) was dissolved at 50 mg/mL (185.0 mM).

HA-MA-2 synthesized in Example 1 was weighed into a microtube, followed by addition of ultrapure water. The tube was allowed to stand overnight at 4° C. to dissolve HA-MA-2. The TEMED solution prepared above was added in ⅕ of the final volume and mixed well. Further, the KPS solution prepared above was added at a final concentration of 20 mM and mixed well. The final volume was set to 100 μl. Air bubbles generated during mixing were removed by centrifugation, and the tube was allowed to stand at room temperature for 1 hour to cause a chemical crosslinking reaction. Sample C3-4 prepared here was calculated for its gel density in the swollen state in the same manner as shown in Example 2-4.

Comparative Example 3-3

Preparation of HA Gel in which HA-MA is Photopolymerized

In 100 mM aqueous hydrochloric acid, TEA was dissolved at 500 mM. When this solution was diluted to ⅕ with ultrapure water, the solution pH was 8.1.

In ethanol, 2-hydroxy-4'-(2-hydroxyethyl)-2-methylpropiophenone (Initiator) (Aldrich) was dissolved at 50 mg/mL (223.0 mM).

HA-MA-2 synthesized in Example 1 was weighed into a microtube, followed by addition of ultrapure water. The tube was allowed to stand overnight at 4° C. to dissolve HA-MA-2. The TEA solution prepared above was added in ⅕ of the final volume and mixed well. Further, the Initiator solution prepared above was added at a final concentration of 20 mM and mixed well. The final volume was set to 100 μl. Air bubbles generated during mixing were removed by centrifugation, and the tube was irradiated with UV light (365 nm, up to 4 W/cm$^2$) using a UV lamp for 10 minutes to cause a chemical crosslinking reaction. Sample C3-5 prepared here was calculated for its gel density in the swollen state in the same manner as shown in Example 2-4.

Comparative Example 3-4

Preparation of HA Gel in which HA and EDOBEA are Crosslinked by Condensation Reaction In 250 mM aqueous hydrochloric acid, TEA was dissolved at 500 mM. When this solution was diluted to ⅕ with ultrapure water, the solution pH was 7.4.

In 1000 mM aqueous hydrochloric acid, EDOBEA was dissolved at 500 mM. The solution pH was 7.5.

In ultrapure water, 4-(4,6-dimethoxy-1,3,5-triazin-2-yl)-4-methylmorpholinium chloride (DMT-MM) (Kokusan Chemical. Co., Ltd., Japan) was dissolved at 500 mg/mL (1595.5 mM when corrected for the initial water content (11.7%) in the reagent).

Sodium hyaluronate of 21 kDa (Shiseido Co., Ltd., Japan) was weighed into a microtube, followed by addition of ultrapure water. The tube was allowed to stand overnight at 4° C. to dissolve sodium hyaluronate. The TEA solution prepared above was added in ⅕ of the final volume and the EDOBEA solution prepared above was added in a 0.28-fold molar amount relative to HA units, followed by mixing well. Further, the DMT-MM solution prepared above was added in a 2-fold molar amount relative to HA units and mixed well. The final volume was set to 100 μl. Air bubbles generated during mixing were removed by centrifugation, and the tube was allowed to stand at 37° C. for 16 hours to cause a chemical crosslinking reaction. Sample C3-6 prepared here was calculated for its gel density in the swollen state in the same manner as shown in Example 2-4.

Comparative Example 3-5

Preparation of HA Gel in which HA-AM is Crosslinked by Condensation Reaction

In 250 mM aqueous hydrochloric acid, TEA was dissolved at 500 mM. When this solution was diluted to ⅕ with ultrapure water, the solution pH was 7.4.

In ultrapure water, DMT-MM was dissolved at 650 mg/mL (2074.1 mM when corrected for the initial water content (11.7%) in the reagent).

HA-AM-1 synthesized in Example 18 was weighed into a microtube, followed by addition of ultrapure water. The tube was allowed to stand overnight at 4° C. to dissolve HA-AM-1. The TEA solution prepared above was added in ⅕ of the final volume and mixed well. Further, the DMT-MM solution prepared above was added in a 2-fold molar amount relative to HA units and mixed well. The final volume was set to 100 μl. Air bubbles generated during mixing were removed by centrifugation, and the tube was allowed to stand at 37° C. for 16 hours to cause a chemical crosslinking reaction. Sample C3-7 prepared here was calculated for its gel density in the swollen state in the same manner as shown in Example 2-4.

Comparative Example 3-6

Preparation of HA Gel in which HA-ITL is Crosslinked by Oxidation Reaction

Ultrapure water used in this comparative example was bubbled with nitrogen before being provided for the following study.

In ultrapure water, TEA was dissolved at 500 mM. When this solution was diluted to ⅕ with ultrapure water, the solution pH was 9.2.

A 30% aqueous solution of hydrogen peroxide (OX) was diluted with ultrapure water to prepare a 1% aqueous OX solution.

The HA-ITL derivative synthesized in Example 19 was weighed into a microtube, followed by addition of ultrapure water. The tube was allowed to stand overnight at 4° C. to dissolve HA-ITL. The TEA solution prepared above was added in ⅕ of the final volume and mixed well. Further, the 1% aqueous OX solution prepared above was added in an equimolar amount relative to SH groups and mixed well. The final volume was set to 100 μl. Air bubbles generated during mixing were removed by centrifugation, and the tube was allowed to stand at 37° C. for 16 hours to cause a chemical crosslinking reaction. Sample C3-8 prepared here was calculated for its gel density in the swollen state in the same manner as shown in Example 2-4.

Comparative Example 3-7

Preparation of HA Gel in which HA-TGA is Crosslinked by Oxidation Reaction

Except that the HA-TGA derivative synthesized in Example 20 was used, the same procedure as shown in Comparative Example 3-6 was repeated to prepare Sample C3-9, followed by calculating the gel density in the swollen state for this sample.

Comparative Example 3-8

Preparation of HA Gel in which HA-MA and HA-DTT are Crosslinked by Michael Addition Reaction Ultrapure water used in this comparative example was bubbled with nitrogen before being provided for the following study.

In 100 mM aqueous hydrochloric acid, TEA was dissolved at 500 mM. When this solution was diluted to ⅕ with ultrapure water, the solution pH was 8.1.

HA-MA-11 synthesized in Example 21-1 and the HA-DTT derivative synthesized in Example 21-2 were each weighed into separate microtubes, followed by addition of ultrapure water. The tubes were allowed to stand overnight at 4° C. to dissolve each derivative. After the HA-MA-11 and HA-DTT solutions were mixed together such that the ratio between MA and HA groups in the system was 1, the TEA solution prepared above was added in ⅕ of the final volume and mixed well. The final volume was set to 100 μl. Air bubbles generated during mixing were removed by centrifugation, and the mixture was allowed to stand at 37° C. for 16 hours to cause a chemical crosslinking reaction. Sample C3-10 prepared here was calculated for its gel density in the swollen state in the same manner as shown in Example 2-4.

gation, and the mixture was allowed to stand at 37° C. for 16 hours to cause a chemical crosslinking reaction. Sample C3-11 prepared here was calculated for its gel density in the swollen state in the same manner as shown in Example 2-4.

TABLE 22

Preparation conditions for various chemically crosslinked HA gels

| Sample | HA derivative, etc. | Final Concentration (mg/mL) | Additives such as crosslinking agent, addition ratio, concentration, etc. | Reaction solution | Reaction conditions |
|---|---|---|---|---|---|
| C3-1 | HA-MA-2 | 50.0 | DTT<br>SH group/MA group = 1 | 100 mM TEA<br>20 mM hydrochloric acid | 37° C.<br>16 hours |
| C3-2 | HA-MA-2 | 100.0 | DTT<br>SH group/MA group = 1 | 100 mM TEA<br>20 mM hydrochloric acid | 37° C.<br>16 hours |
| C3-3 | HA-MA-2 | 150.0 | DTT<br>SH group/MA group = 1 | 100 mM TEA<br>20 mM hydrochloric acid | 37° C.<br>16 hours |
| C3-4 | HA-MA-2 | 50.0 | 20 mM KPS<br>100 mM TEMED | 100 mM hydrochloric acid | RT<br>1 hour |
| C3-5 | HA-MA-2 | 50.0 | 20 mM Initiator | 100 mM TEA<br>20 mM hydrochloric acid | UV<br>10 minutes |
| C3-6 | HA EDOBEA | 50.0<br>5.2 | DMT-MM<br>(DMT-MM/HA = 2) | 100 mM TEA<br>50 mM hydrochloric acid | 37° C.<br>16 hours |
| C3-7 | HA-AM-1 | 100.0 | DMT-MM<br>(DMT-MM/HA = 2) | 100 mM TEA<br>50 mM hydrochloric acid | 37° C.<br>16 hours |
| C3-8 | HA-ITL | 50.0 | Hydrogen peroxide (OX)<br>(OX/SH group = 1) | 100 mM TEA | 37° C.<br>16 hours |
| C3-9 | HA-TGA | 50.0 | Hydrogen peroxide (OX)<br>(OX/SH group = 1) | 100 mM TEA | 37° C.<br>16 hours |
| C3-10 | HA-MA-11<br>HA-DTT | 23.7<br>26.3 | SH group/MA group = 1 | 100 mM TEA<br>20 mM hydrochloric acid | 37° C.<br>16 hours |
| C3-11 | HA-MA-11<br>HA-TGA | 17.4<br>32.6 | SH group/MA group = 1 | 100 mM TEA<br>20 mM hydrochloric acid | 37° C.<br>16 hours | here was calculated for its gel density in the swollen state in the same manner as shown in Example 2-4.

Comparative Example 3-9

Preparation of HA Gel in which HA-MA and HA-TGA are Crosslinked by Michael Addition Reaction Ultrapure water used in this comparative example was bubbled with nitrogen before being provided for the following study.

In 100 mM aqueous hydrochloric acid, TEA was dissolved at 500 mM. When this solution was diluted to ⅕ with ultrapure water, the solution pH was 8.1.

HA-MA-11 synthesized in Example 21-1 and the HA-TGA derivative synthesized in Example 20 were each weighed into separate microtubes, followed by addition of ultrapure water. The tubes were allowed to stand overnight at 4° C. to dissolve each derivative. After the HA-MA-11 and HA-DTT solutions were mixed together such that the ratio between MA and HA groups in the system was 1, the TEA solution prepared above was added in ⅕ of the final volume and mixed well. The final volume was set to 100 μl. Air bubbles generated during mixing were removed by centrifu- Example 23

Preparation of Various Chemically Crosslinked HA Hybrid Gels Encapsulating Nanogels (CHP, CHcDex)

The HA derivatives and nanogels used for each sample preparation (Samples 23-1 to 23-15) are shown in Table 23, along with their final concentrations, crosslinking agents, reaction conditions and so on.

Example 23-1

Preparation of CHP-Encapsulating Hybrid Gel in which HA-MA is Crosslinked by Michael Addition Reaction Except that the sample solution before use for chemical crosslinking was modified to contain 20 mg/mL CHP, the same procedure as shown in Comparative Example 3-1 was repeated to prepare the CHP-encapsulating hybrid gels of Samples 23-1 to 23-3 indicated in Table 23, followed by calculating the gel density in the swollen state for each sample.

Example 23-2

Preparation of CHP-Encapsulating Hybrid Gel in which HA-MA is Crosslinked by Radical Polymerization

Except that the sample solution before use for chemical crosslinking was modified to contain 20 mg/mL CHP, the same procedure as shown in Comparative Example 3-2 was repeated to prepare the CHP-encapsulating hybrid gel of Sample 23-4 indicated in Table 23, followed by calculating the gel density in the swollen state for this sample.

Example 23-3

Preparation of CHP-Encapsulating Hybrid Gel in which HA-MA is Photopolymerized

Except that the sample solution before use for chemical crosslinking was modified to contain 20 mg/mL CHP, the same procedure as shown in Comparative Example 3-3 was repeated to prepare the CHP-encapsulating hybrid gel of Sample 23-5 indicated in Table 23, followed by calculating the gel density in the swollen state for this sample.

Example 23-4

Preparation of CHP-Encapsulating Hybrid Gel in which HA and EDOBEA are Crosslinked by Condensation Reaction

Except that the sample solution before use for chemical crosslinking was modified to contain 20 mg/mL CHP, the same procedure as shown in Comparative Example 3-4 was repeated to prepare the CHP-encapsulating hybrid gel of Sample 23-6 indicated in Table 23, followed by calculating the gel density in the swollen state for this sample.

Example 23-5

Preparation of CHP-Encapsulating Hybrid Gel in which HA-AM is Crosslinked by Condensation Reaction

Except that the sample solution before use for chemical crosslinking was modified to contain 20 mg/mL CHP, the same procedure as shown in Comparative Example 3-5 was repeated to prepare the CHP-encapsulating hybrid gels of Samples 23-7 and 23-8 indicated in Table 23, followed by calculating the gel density in the swollen state for each sample.

Example 23-6

Preparation of CHP-Encapsulating Hybrid Gel in which HA-ITL is Crosslinked by Oxidation Reaction

Except that the sample solution before use for chemical crosslinking was modified to contain 20 mg/mL CHP, the same procedure as shown in Comparative Example 3-6 was repeated to prepare the CHP-encapsulating hybrid gel of Sample 23-9 indicated in Table 23, followed by calculating the gel density in the swollen state for this sample.

Example 23-7

Preparation of CHP-Encapsulating Hybrid Gel in which HA-TGA is Crosslinked by Oxidation Reaction

Except that the sample solution before use for chemical crosslinking was modified to contain 20 mg/mL CHP, the same procedure as shown in Comparative Example 3-7 was repeated to prepare the CHP-encapsulating hybrid gel of Sample 23-10 indicated in Table 23, followed by calculating the gel density in the swollen state for this sample.

Example 23-8

Preparation of CHP-Encapsulating Hybrid Gel in which HA-MA and HA-DTT are Crosslinked by Michael Addition Reaction

Except that the sample solution before use for chemical crosslinking was modified to contain 7.5 mg/mL CHP, the same procedure as shown in Comparative Example 3-8 was repeated to prepare the CHP-encapsulating hybrid gel of Sample 23-11 indicated in Table 23, followed by calculating the gel density in the swollen state for this sample.

Example 23-9

Preparation of CHP-Encapsulating Hybrid Gel in which HA-MA and HA-TGA are Crosslinked by Michael Addition Reaction

Except that the sample solution before use for chemical crosslinking was modified to contain 7.5 mg/mL CHP, the same procedure as shown in Comparative Example 3-9 was repeated to prepare the CHP-encapsulating hybrid gel of Sample 23-12 indicated in Table 23, followed by calculating the gel density in the swollen state for this sample.

Example 23-10

Preparation of CHcDEX-Encapsulating Hybrid Gel in which HA-MA is Crosslinked by Michael Addition Reaction

Except that the sample solution before use for chemical crosslinking was modified to contain 20 mg/mL CHcDex, the same procedure as shown in Comparative Example 3-1 was repeated to prepare the CHP-encapsulating hybrid gel of Sample 23-13 indicated in Table 23, followed by calculating the gel density in the swollen state for this sample.

Table 24 shows the results of gel density calculated in Comparative Examples 3-1 to 3-9 and Examples 23-1 to 23-10 above. When the yield relative to the theoretical value was calculated from the weight of lyophilized gel, all the gels were found to have virtually 100% yields. Moreover, in the hybrid gels crosslinked by various chemical reactions in the presence of nanogels (CHP and CHcDex), their gel density was found to increase when compared to the absence of the nanogels. These results suggested that the nanogels were encapsulated within the various hybrid gels prepared in these examples.

TABLE 23

Preparation conditions for various nanogel-encapsulating chemically crosslinked HA hybrid gels

| Sample | HA derivative nanogel, etc. | Final concentration (mg/mL) | Additives such as crosslinking agent, addition ratio, concentration, etc. | Reaction solution | Reaction conditions |
|---|---|---|---|---|---|
| 23-1 | HA-MA-2<br>CHP | 50.0<br>20.0 | DTT<br>SH group/MA group = 1 | 100 mM TEA<br>20 mM<br>hydrochloric acid | 37° C.<br>16 hours |
| 23-2 | HA-MA-2<br>CHP | 100.0<br>20.0 | DTT<br>SH group/MA group = 1 | 100 mM TEA<br>20 mM<br>hydrochloric acid | 37° C.<br>16 hours |
| 23-3 | HA-MA-2<br>CHP | 150.0<br>20.0 | DTT<br>SH group/MA group = 1 | 100 mM TEA<br>20 mM<br>hydrochloric acid | 37° C.<br>16 hours |
| 23-4 | HA-MA-2<br>CHP | 50.0<br>20.0 | 20 mM KPS<br>100 mM TEMED | 100 mM<br>hydrochloric acid | RT<br>1 hour |
| 23-5 | HA-MA-2<br>CHP | 50.0<br>20.0 | 20 mM<br>Initiator | 100 mM TEA<br>20 mM<br>hydrochloric acid | UV<br>10 minutes |
| 23-6 | HA<br>EDOBEA<br>CHP | 50.0<br>5.2<br>20.0 | DMT-MM<br>(DMT-MM/HA = 2) | 100 mM TEA<br>50 mM<br>hydrochloric acid | 37° C.<br>16 hours |
| 23-7 | HA-AM-1<br>CHP | 60.0<br>20.0 | DMT-MM<br>(DMT-MM/HA = 2) | 100 mM TEA<br>50 mM<br>hydrochloric acid | 37° C.<br>16 hours |
| 23-8 | HA-AM-1<br>CHP | 100.0<br>20.0 | DMT-MM<br>(DMT-MM/HA = 2) | 100 mM TEA<br>50 mM<br>hydrochloric acid | 37° C.<br>16 hours |
| 23-9 | HA-ITL<br>CHP | 50.0<br>20.0 | Hydrogen peroxide<br>(OX)<br>(OX/SH group = 1) | 100 mM TEA | 37° C.<br>16 hours |
| 23-10 | HA-TGA<br>CHP | 50.0<br>20.0 | Hydrogen peroxide<br>(OX)<br>(OX/SH group = 1) | 100 mM TEA | 37° C.<br>16 hours |
| 23-11 | HA-MA-11<br>HA-DTT<br>CHP | 23.7<br>26.3<br>7.5 | SH group/MA group = 1 | 100 mM TEA<br>20 mM<br>hydrochloric acid | 37° C.<br>16 hours |
| 23-12 | HA-MA-11<br>HA-TGA<br>CHP | 17.4<br>32.6<br>7.5 | SH group/MA group = 1 | 100 mM TEA<br>20 mM<br>hydrochloric acid | 37° C.<br>16 hours |
| 23-13 | HA-MA-2<br>CHcDex | 50.0<br>20.0 | DTT<br>SH group/MA group = 1 | 100 mM TEA<br>20 mM<br>hydrochloric acid | 37° C.<br>16 hours |

TABLE 24

Comparison of gel density in the swollen state in various
nanogel-encapsulating hybrid gels and chemically crosslinked HA gels

| Nanogel-encapsulating hybrid gel sample | Gel density in swollen state (% w/w) | Non-nanogel-encapsulating HA gel sample | Gel density in swollen state (% w/w) |
| --- | --- | --- | --- |
| 23-1  | 2.22  | C3-1  | 1.57 |
| 23-2  | 5.77  | C3-2  | 4.53 |
| 23-3  | 8.71  | C3-3  | 7.15 |
| 23-4  | 5.71  | C3-4  | 4.44 |
| 23-5  | 3.74  | C3-5  | 2.73 |
| 23-6  | 3.97  | C3-6  | 2.68 |
| 23-7  | 6.86  | —     | —    |
| 23-8  | 11.45 | C3-7  | 8.50 |
| 23-9  | 2.01  | C3-8  | 1.46 |
| 23-10 | 2.71  | C3-9  | 2.03 |
| 23-11 | 2.61  | C3-10 | 2.18 |
| 23-12 | 2.65  | C3-11 | 2.30 |
| 23-13 | 2.15  | C3-1  | 1.57 |

Example 24

Evaluation on Encapsulation and Release Properties of Insulin into/from CHP-Encapsulating Various Chemically Crosslinked HA Hybrid Gels Example 24-1

Preparation of Various Hybrid Gels

Samples 24-1 to 24-5 indicated in Table 25 were prepared in duplicate in the same manner as shown in Example 23 to give various lyophilized hybrid gels, each of which was then transferred to a microtube.

TABLE 25

Preparation conditions for various nanogel-encapsulating chemically crosslinked HA hybrid gels

| Sample | HA derivative nanogel, etc. | Final concentration (mg/mL) | Additives such as crosslinking agent, addition ratio, concentration, etc. | Reaction solution | Reaction conditions |
| --- | --- | --- | --- | --- | --- |
| 24-1 | HA-MA-2 | 50.0 | DTT | 100 mM TEA | 37° C. |
|      | CHP     | 20.0 | SH group/MA group = 1 | 20 mM hydrochloric acid | 16 hours |
| 24-2 | HA-MA-2 | 50.0 | 20 mM KPS | 100 mM | RT |
|      | CHP     | 20.0 | 100 mM TEMED | hydrochloric acid | 1 hour |
| 24-3 | HA-MA-2 | 50.0 | 20 mM | 100 mM TEA | UV |
|      | CHP     | 20.0 | Initiator | 20 mM hydrochloric acid | 10 minutes |
| 24-4 | HA      | 50.0 | DMT-MM | 100 mM TEA | 37° C. |
|      | EDOBEA  | 5.2  | (DMT-MM/HA = 2) | 50 mM hydrochloric acid | 16 hours |
|      | CHP     | 20.0 |        |                         |          |
| 24-5 | HA-ITL  | 50.0 | Hydrogen peroxide | 100 mM TEA | 37° C. |
|      | CHP     | 20.0 | (OX) | | 16 hours |
|      |         |      | (OX/SH group = 1) | | |

Example 24-2

Insulin Encapsulation and Calculation of Encapsulated Amount

Insulin (derived from bovine pancreas) was dissolved at 250 μg/mL in 300 mM PB (pH 7.0).

The insulin solution was added in 1 mL volumes to the microtubes containing the hybrid gels and allowed to stand at 4° C. for 3 days, followed by decantation to remove the insulin solution. After addition of an excessive amount of PBS (prepared by dissolving PBS tablets in ultrapure water, SIGMA), each tube was allowed to stand at 4° C. and, after several hours, was decanted to remove the added PBS. After this procedure was repeated several times, water on the gel surface was removed with Kimwipes. One of the gels of each sample was provided for the following study to evaluate the encapsulated amount, and the other was provided for the study in Example 24-3 to evaluate the release behavior of insulin.

To each hybrid gel encapsulating insulin, 500 μl of PBS containing 25 mM HP-β-CD and 0.05% Tween 20 (CTB) was added and incubated at 37° C. At 2 hours, 1 day, 2 days and 4 days after initiation of the incubation, 400 μL supernatant was collected and 400 μL fresh CTB was added instead. The insulin concentration in each collected supernatant was quantified by RP-HPLC (under the same conditions as shown in Example 6-2) to calculate the cumulative amount of insulin released from the hybrid gel until each time point for measurement. Since all the samples were found to stop insulin release until after 2 to 4 days, the cumulative release amount until after 4 days was defined as the amount of insulin encapsulated into each hybrid gel. The results obtained are shown in Table 26.

TABLE 26

Amount of insulin encapsulated into various nanogel-encapsulating hybrid gels

| Sample | HA derivative | Crosslinking reaction | Amount of encapsulated insulin Weight relative to CHP (initial amount) (% w/w) | Weight relative to dry gel (% w/w) |
|---|---|---|---|---|
| 24-1 | HA-MA | Michael addition | 7.4 | 2.1 |
| 24-2 | HA-MA | Radical polymerization | 7.2 | 2.1 |
| 24-3 | HA-MA | Photopolymerization | 7.4 | 2.1 |
| 24-4 | HA/EDOBEA | Condensation | 5.6 | 1.6 |
| 24-5 | HA-ITL | Oxidation | 7.3 | 2.1 |

Example 24-3

Release Behavior of Insulin

Figure 24:
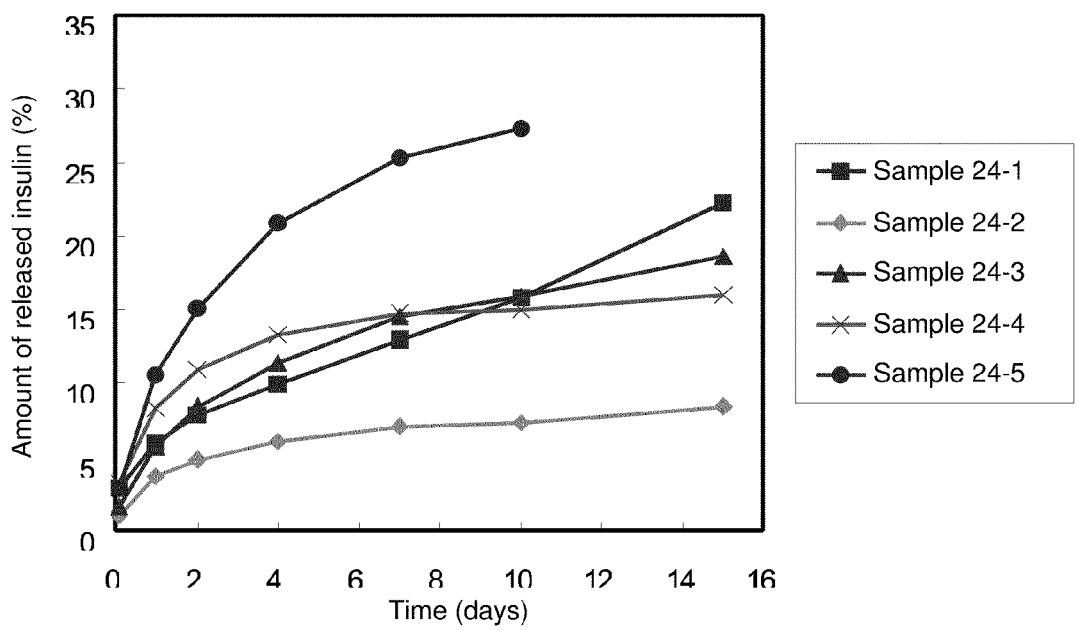
FIG. 24 is a graph showing the release behavior of insulin from various CHP-encapsulating chemically crosslinked hybrid gels.

To each hybrid gel treated to encapsulate insulin in Example 24-2, 500 µl of 0.05% sodium azide-containing PBS (SAB) was added and incubated at 37° C. At 2 hours, 1 day, 2 days, 4 days, 7 days, 10 days and 15 days after initiation of the incubation (until 10 days for Sample 25-5), 400 µL supernatant was collected and 400 µL fresh SAB was added instead. The insulin concentration in each collected supernatant was quantified by RP-HPLC (under the same conditions as shown in Example 6-2) to calculate the cumulative amount of insulin released from the hybrid gel until each time point for measurement. This value is plotted as a percentage of the amount of encapsulated insulin (calculated in Example 24-2) in FIG. 24.

As a result, the release behavior of insulin from all the hybrid gels used in this study was found to have a sustained release profile. Differences in their release behavior would be due to differences in their gel density and/or degradation rate.

Example 25

Evaluation on Encapsulation and Release Properties of Insulin into/from CHcD-Encapsulating Various Chemically Crosslinked HA Hybrid Gels Example 25-1

Insulin Encapsulation and Calculation of Encapsulated Amount

Sample 25-1 indicated in Table 27 was prepared in duplicate in the same manner as shown in Example 23 to give lyophilized hybrid gels, each of which was then transferred to a microtube.

The same procedure as shown in Example 24-2 was repeated to encapsulate insulin and calculate the amount of encapsulated insulin, indicating that it was 3.4% w/w relative to the initial weight of CHcDex and 1.0% w/w relative to the dry gel weight.

TABLE 27

Preparation conditions for CHcDex-encapsulating chemically crosslinked HA-MA hybrid gel

| Sample | HA derivative nanogel, etc. | Final concentration (mg/mL) | Additives such as crosslinking agent, addition ratio, concentration, etc. | Reaction solution | Reaction conditions |
|---|---|---|---|---|---|
| 25-1 | HA-MA-2 CHcDex | 50.0 20.0 | DTT SH group/MA group = 1 | 100 mM TEA 20 mM hydrochloric acid | 37° C. 16 hours |

Example 25-2

Release Behavior of Insulin

Figure 25:
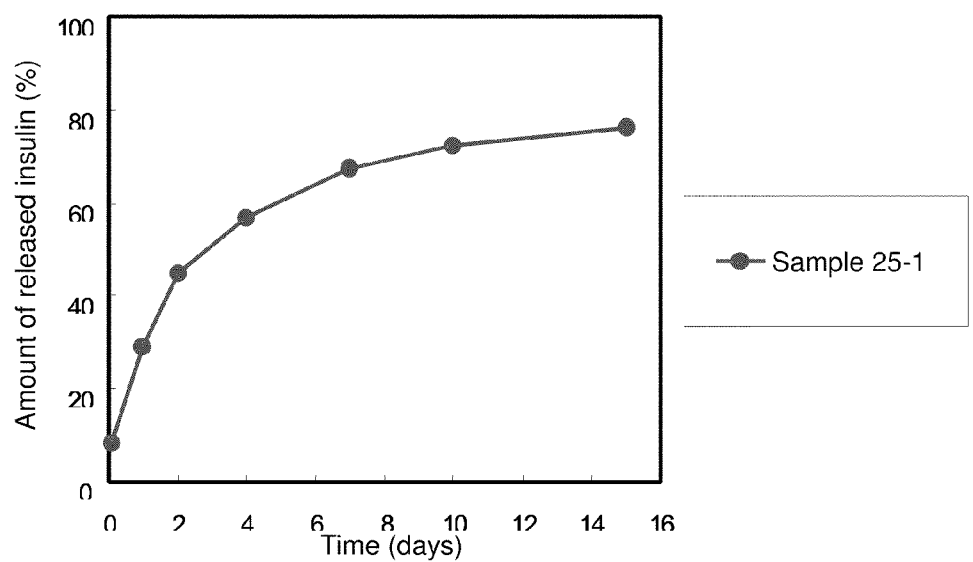
FIG. 25 is a graph showing the release behavior of insulin from a ChcDex-encapsulating chemically crosslinked HA-MA hybrid gel.

Sample 25-1 treated to encapsulate insulin in Example 25-1 was evaluated for the release behavior of insulin in the same manner as shown in Example 24-3. The results obtained are shown in FIG. 25.

As a result, the release behavior of insulin from the hybrid gel encapsulating CHcDex, a hydrophobized polysaccharide (nanogel) having a different skeletal polysaccharide, was found to have a sustained release profile.

Example 26

Evaluation on Encapsulation and Release Properties of Glucagon-Like Peptide-1 (GLP-1) Into/From CHP-Encapsulating Chemically Crosslinked HA-MA Hybrid Gel Example 26-1

GLP-1 Encapsulation and Calculation of Encapsulated Amount

Sample 26-1 indicated in Table 28 was prepared in duplicate in the same manner as shown in Example 23 to give various lyophilized hybrid gels, each of which was then transferred to a microtube.

Natural GLP-1[7-37] (American Peptide Co., Inc.) was dissolved in 300 mM PB (pH 7.0) to give a peptide concentration of 500 μg/mL.

The same procedure as shown in Example 24-2 was repeated to encapsulate GLP-1 and calculate the amount of encapsulated GLP-1 for Sample 26-1, indicating that it was 20.6% w/w relative to the initial weight of CHP and 5.9% w/w relative to the dry gel weight.

TABLE 28

Preparation conditions for CHP-encapsulating chemically crosslinked HA-MA hybrid gel

| Sample | HA derivative nanogel, etc. | Final concentration (mg/mL) | Additives such as crosslinking agent, addition ratio, concentration, etc. | Reaction solution | Reaction conditions |
|---|---|---|---|---|---|
| 26-1 | HA-MA-2 CHP | 50.0 20.0 | DTT SH group/MA group = 1 | 100 mM TEA 20 mM hydrochloric acid | 37° C. 16 hours |

Example 26-2

Release Behavior of GLP-1

Figure 26:
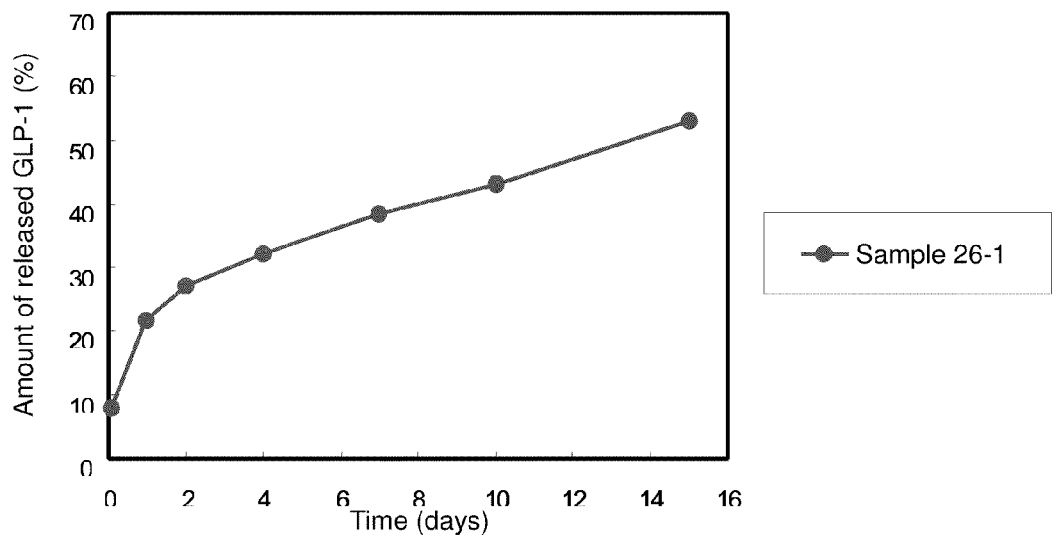
FIG. 26 is a graph showing the release behavior of GLP-1 from a CHP-encapsulating chemically crosslinked HA-MA hybrid gel.

Sample 26-1 treated to encapsulate GLP-1 in Example 26-1 was evaluated for the release behavior of GLP-1 in the same manner as shown in Example 24-3. The results obtained are shown in FIG. 26. As a result, the release behavior of GLP-1 from the hybrid gel used in this study was found to have a sustained release profile.

Example 27

Evaluation on Encapsulation and Release Properties of Erythropoietin (EPO) Into/From CHP-Encapsulating Chemically Crosslinked HA-MA Hybrid Gel

Example 27-1

EPO Encapsulation and Calculation of Encapsulated Amount

Sample 27-1 indicated in Table 29 was prepared in duplicate in the same manner as shown in Example 23 to give various lyophilized hybrid gels, each of which was then transferred to a microtube.

A drug bulk solution of erythropoietin (EPO) (Chugai Pharmaceutical Co., Ltd., Japan) was diluted with 50 mM PB (pH 6.5) to give a polypeptide concentration of 500 μg/mL.

Except that the amount of the drug solution added to each hybrid gel was changed to 0.5 mL and the incubation temperature and time were changed to 37° C. and 4 days, the same procedure as shown in Example 24-2 was repeated to encapsulate EPO. Except that the SEC analysis conditions shown below were used for quantification, the same procedure as shown in Example 24-2 was repeated to calculate the amounts of encapsulated EPO and CHP (prior to quantification, it was verified that EPO was completely dissociated from EPO/CHP complexes and quantitatively detected as free EPO in this SEC analysis). As a result, the amount of encapsulated EPO was 6.8% w/w relative to the initial weight of CHP and 2.0% w/w relative to the dry gel weight. Likewise, the ratio of release amount relative to the initial amount of CHP (i.e., yield in the step of gelling, washing, encapsulation or the like) was 61.3%.

SEC Analysis Conditions
System: Waters Alliance 2790/2487
Column: G2000SWXL (TOSOH)
Flow rate: 1.0 mL/minute
Detection: UV detection (280 nm)
Eluent: 10 mM HP-β-CD-containing PBS
Injection volume: 50 μL

TABLE 29

Preparation conditions for CHP-encapsulating chemically crosslinked HA-MA hybrid gel

| Sample | HA derivative nanogel, etc. | Final concentration (mg/mL) | Additives such as crosslinking agent, addition ratio, concentration, etc. | Reaction solution | Reaction conditions |
|---|---|---|---|---|---|
| 27-1 | HA-MA-2 CHP | 50.0 20.0 | DTT SH group/MA group = 1 | 100 mM TEA 20 mM hydrochloric acid | 37° C. 16 hours |

Example 27-2

Release Behavior of EPO and CHP

Figure 27:
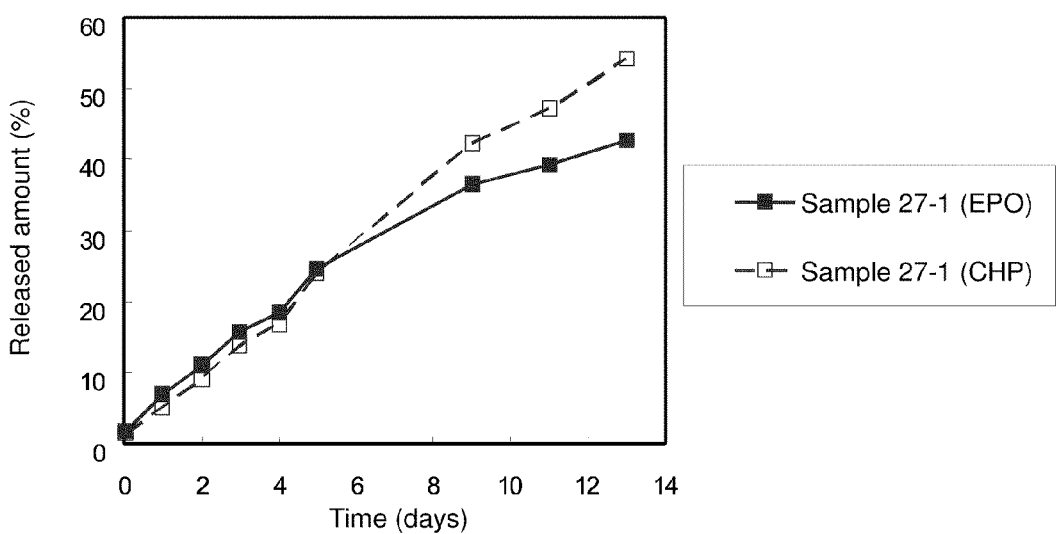
FIG. 27 is a graph showing the release behavior of EPO and CHP from a CHP-encapsulating chemically crosslinked HA-MA hybrid gel.

Except that the release behavior of EPO and CHP from the hybrid gel treated to encapsulate EPO in Example 27-1 was quantified under the SEC analysis conditions shown below, the same procedure as shown in Example 24-3 was repeated to evaluate the time-dependent release behavior of EPO and CHP. The results obtained are shown in FIG. 27.

The release behavior of EPO from the hybrid gel used in this study was found to have a sustained release profile. Likewise, sustained release was also observed for CHP and its release behavior was almost the same as that of EPO. In view of the findings that the species released from the hybrid gels in Example 7 was only insulin/CHP complexes and that EPO and CHP showed almost the same release behavior in this study, it was suggested that drug release from the hybrid gel was caused by release of the nanogel.

SEC Analysis Conditions
System: Waters Alliance 2790/2487/2414
Column: G2000SWXL (TOSOH)
Flow rate: 1.0 mL/minute
Detection: UV detection (280 nm) for EPO
differential refractive index (RI) detection for CHP
Eluent: 10 mM HP-$\beta$-CD-containing PBS
Injection volume: 50 µL

Example 28

Evaluation on Encapsulation and Release Properties of Erythropoietin (EPO) Into/From CHP-Encapsulating Chemically Crosslinked HA-AM Hybrid Gel

Example 28-1

EPO Encapsulation and Calculation of Encapsulated Amount

Samples 28-1 and 28-2 indicated in Table 30 were prepared in duplicate in the same manner as shown in Example 23 to give various lyophilized hybrid gels, each of which was then transferred to a microtube.

The same procedure as shown in Example 27-1 was repeated to encapsulate EPO and calculate the amount of encapsulated EPO. The results obtained are shown in Table 31.

TABLE 30

Preparation conditions for CHP-encapsulating chemically crosslinked HA-AM hybrid gels

| Sample | HA derivative nanogel, etc. | Final concentration (mg/mL) | Additives such as crosslinking agent, addition ratio, concentration, etc. | Reaction solution | Reaction conditions |
|---|---|---|---|---|---|
| 28-1 | HA-AM-1 | 60.0 | DMT-MM | 100 mM TEA | 37° C. |
|  | CHP | 20.0 | (DMT-MM/HA = 2) | 50 mM hydrochloric acid | 16 hours |
| 28-2 | HA-AM-1 | 100.0 | DMT-MM | 100 mM TEA | 37° C. |
|  | CHP | 20.0 | (DMT-MM/HA = 2) | 50 mM hydrochloric acid | 16 hours |

TABLE 31

Amount of EPO encapsulated into CHP-encapsulating HA-AM hybrid gels

| | | Concentration | Amount of encapsulated EPO | |
|---|---|---|---|---|
| Sample | HA derivative | of HA derivative (mg/mL) | Weight relative to CHP (initial amount) (% w/w) | Weight relative to dry gel (% w/w) |
| 28-1 | HA-AM | 60.0 | 6.7 | 1.9 |
| 28-2 | HA-AM | 100.0 | 2.9 | 0.5 |

Example 28-2

Release Behavior of EPO

Figure 28:
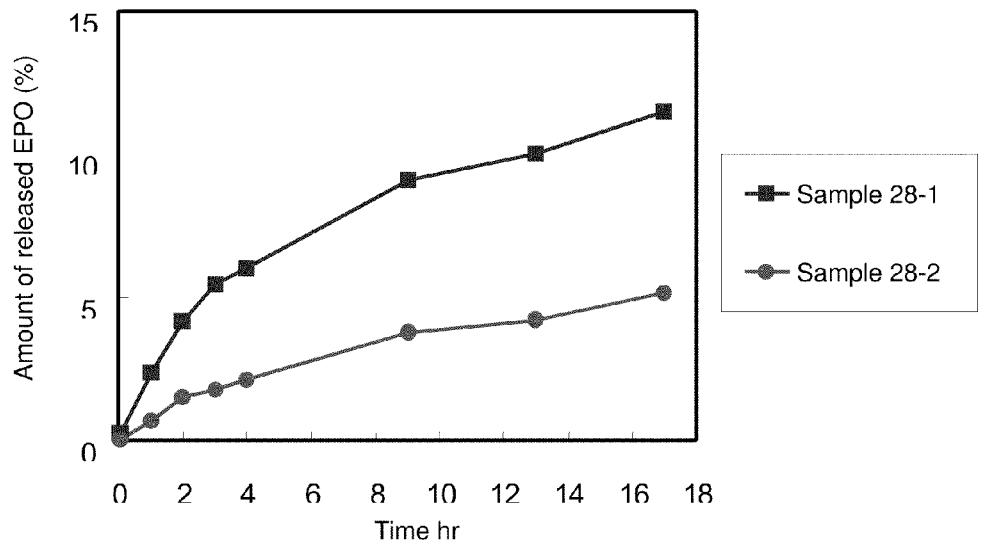
FIG. 28 is a graph showing the release behavior of EPO from CHP-encapsulating chemically crosslinked HA-AM hybrid gels.

The release behavior of EPO from the hybrid gels treated to encapsulate EPO in Example 28-1 was analyzed in the same manner as shown in Example 27-2 to evaluate the time-dependent release behavior of EPO. The results obtained are shown in FIG. 28.

The release behavior of EPO from the hybrid gels used in this study was found to have a sustained release profile. Moreover, as in the case of Example 6, the release rate was found to vary depending on the gel density (see the gel density of Samples 23-7 and 23-8 calculated in Example 23).

Example 29

Preparation of Hybrid Gel in which HA Derivative is Chemically Crosslinked in the Presence of Nanogel/EPO Complex Ultrapure water used in this example was bubbled with nitrogen before being provided for the following study.

In 100 mM aqueous hydrochloric acid, TEA was dissolved at 500 mM. When this solution was diluted to ⅕ with ultrapure water, the solution pH was 8.1.

HA-MA-11 synthesized in Example 21-1 and the HA-DTT derivative synthesized in Example 21-2 were each weighed into separate microtubes, followed by addition of ultrapure water. The tubes were allowed to stand overnight at 4° C. to dissolve each derivative.

DTT was dissolved in ultrapure water at a concentration of 50 mg/mL.

CHP was dissolved in ultrapure water at a concentration of 30 mg/mL.

A drug bulk solution of erythropoietin (EPO) (Chugai Pharmaceutical Co., Ltd., Japan), the above CHP solution and ultrapure water were mixed to prepare a solution having an EPO polypeptide concentration of 450 µg/mL and a CHP concentration of 15 mg/mL. The resulting solution was allowed to stand overnight at 37° C. When SEC analysis was performed under the same SEC analysis conditions as shown in Example 7, free EPO (retention time: 7.1 minutes) was not detected and only EPO/CHP complexes (retention time: 5.6 minutes) were detected, thus confirming that all EPO molecules in the system formed complexes with CHP.

Each HA derivative solution, the EPO/CHP complex solution, ultrapure water, the DTT solution (for Sample 29-2 only) and the TEA solution were mixed at the ratio indicated in Table 32. The final volume was set to 50 µl. Air bubbles generated during mixing were removed by centrifugation, and each mixture was allowed to stand at 37° C. for 16 hours to cause a chemical crosslinking reaction. The samples prepared here were provided for Example 30.

TABLE 32

Preparation conditions for hybrid gels chemically crosslinked in the presence of EPO/nanogel complex

| Sample | HA derivative nanogel, etc. | Final concentration (mg/mL) | Additives such as crosslinking agent, addition ratio, concentration, etc. | Reaction solution | Reaction conditions |
|---|---|---|---|---|---|
| 29-1 | HA-MA-11 | 23.7 | SH group/MA group = 1 | 100 mM TEA 20 mM hydrochloric acid | 37° C. 16 hours |
|  | HA-DTT | 26.3 |  |  |  |
|  | CHP | 7.5 |  |  |  |
|  | EPO | 0.225 |  |  |  |
| 29-2 | HA-MA-11 | 50.0 | DTT SH group/MA group = 1 | 100 mM TEA 20 mM hydrochloric acid | 37° C. 16 hours |
|  | CHP | 7.5 |  |  |  |
|  | EPO | 0.225 |  |  |  |

Comparative Example 4

Preparation of Hybrid Gel in which HA Derivative is Chemically Crosslinked in the Presence of EPO A drug bulk solution of erythropoietin (EPO) (Chugai Pharmaceutical Co., Ltd., Japan) was diluted to give an EPO polypeptide concentration of 450 µg/mL by being mixed with ultrapure water.

Except that the above EPO solution was used, the same procedure as shown in Example 29 was repeated to prepare the hybrid gels indicated in Table 33, which were then provided for Example 30.

TABLE 33

Preparation conditions for hybrid gels chemically crosslinked in the presence of EPO

| Sample | HA derivative nanogel, etc. | Final concentration (mg/mL) | Additives such as crosslinking agent, addition ratio, concentration, etc. | Reaction solution | Reaction conditions |
|---|---|---|---|---|---|
| C4-1 | HA-MA-11 | 23.7 | SH group/MA group = 1 | 100 mM TEA 20 mM hydrochloric acid | 37° C. 16 hours |
|  | HA-DTT | 26.3 |  |  |  |
|  | EPO | 0.225 |  |  |  |
| C4-2 | HA-MA-11 | 50.0 | DTT SH group/MA group = 1 | 100 mM TEA 20 mM hydrochloric acid | 37° C. 16 hours |
|  | EPO | 0.225 |  |  |  |

Example 30

Figure 29:
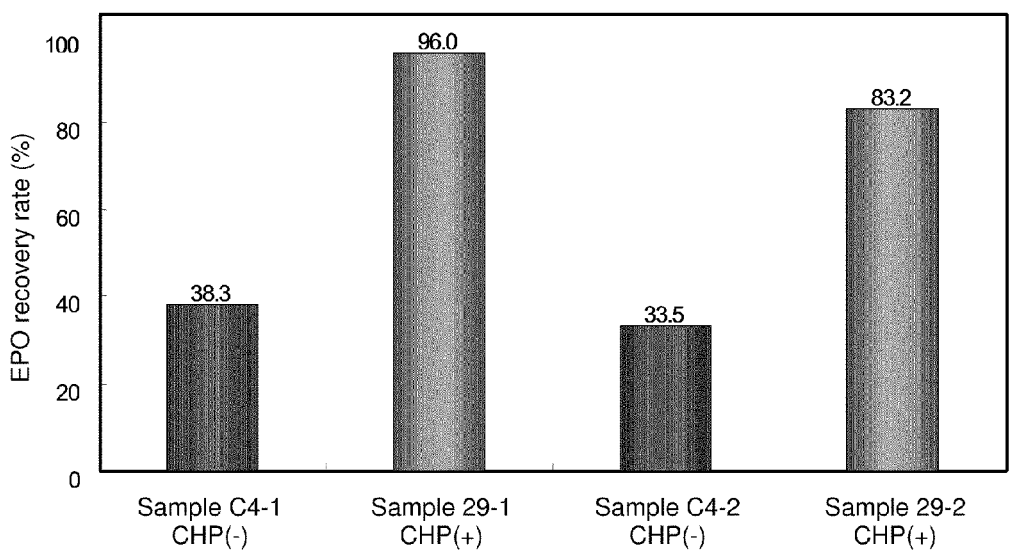
FIG. 29 is a graph showing the recovery rate of EPO from hybrid gels chemically crosslinked in the presence of an EPO/CHP complex or EPO.

Evaluation on Drug Stability in Hybrid Gel Prepared to Encapsulate the Drug by Chemical Crosslinking in the Presence of EPO or Nanogel/EPO Complex To each of the samples prepared in Example 29 and Comparative Example 4, 250 µl of PBS containing 25 mM HP-β-CD and 0.05% Tween 20 was added and incubated at 37° C. At 2 hours, 10 hours, 2 days, 3 days, 5 days, 7 days and 11 days after initiation of the incubation, 200 µL supernatant was collected and 200 µL fresh PBS containing 25 mM HP-β-CD and 0.05% Tween 20 was added instead. The EPO concentration in each collected supernatant was quantified by RP-HPLC (under the analysis conditions shown below) and by SEC analysis under the same conditions as shown in Example 27-1 to calculate the cumulative amount of EPO released until each time point for measurement. There was no significant difference in the results quantified by RP-HPLC and SEC. All the samples were found to stop EPO release until after 7 to 11 days. The cumulative release amount until after 11 days relative to the initial amount of EPO was defined as the EPO recovery rate, and this value (quantified by RP-HPLC) is shown in FIG. 29.

As a result, pre-complexation between EPO and nanogel significantly increased the amount of EPO recovered from the gel, and particularly in Sample 29-1, almost all of the initial amount of EPO was recovered. This would be because EPO complexed with the nanogel was significantly less reactive to HA derivatives or crosslinking agents when compared to free EPO. Thus, the process shown in Example 29 would be an effective procedure for avoidance of unwanted side reactions when drug encapsulation into chemically crosslinked HA gels was accomplished by chemical crosslinking in the presence of the drug.

RP-HPLC Analysis Conditions
System: Waters Alliance 2790/2487
Column: Symmetry300 C4 (3.5 µm) 2.1 mm×50 mm (Waters, Inc.)
Flow rate: 0.75 mL/minute
Detection: UV (280 nm)
Eluent A: 0.1% w/v TFA-containing ultrapure water
Eluent B: 0.1% w/v TFA-containing acetonitrile
Elution: linear gradient of Eluent A/Eluent B=90/10 to 40/60

Example 31

Preparation of Various Hybrid Gels for Use in Pharmacokinetic Test in Rats

Samples 31-1 and 31-2 indicated in Table 34 were prepared in 15-plicate and Sample 31-3 was prepared in 27-plicate in the same manner as shown in Example 23, followed by calculating the gel density for each sample. The results obtained are shown in Table 35.

TABLE 34

Preparation conditions for hybrid gels for use in pharmacokinetic test

| Sample | HA derivative nanogel, etc. | Final concentration (mg/mL) | n | Additives such as crosslinking agent, addition ratio, concentration, etc. | Reaction solution | Reaction conditions |
|---|---|---|---|---|---|---|
| 31-1 | HA-MA-2 CHP | 50.0 20.0 | 15 | DTT SH group/MA group = 1 | 100 mM TEA 20 mM hydrochloric acid | 37° C. 16 hours |
| 31-2 | HA-MA-2 CHP | 100.0 20.0 | 15 | DTT SH group/MA group = 1 | 100 mM TEA 20 mM hydrochloric acid | 37° C. 16 hours |
| 31-3 | HA-AM-1 CHP | 100.0 20.0 | 27 | DMT-MM DMT-MM/HA = 2 | 100 mM TEA 50 mM hydrochloric acid | 37° C. 16 hours |

TABLE 35

Preparation results of hybrid gels for use in pharmacokinetic test

| Nanogel-encapsulating hybrid gel sample | n | Gel density in swollen state (% w/w) | |
|---|---|---|---|
| | | Mean | Standard deviation |
| 31-1 | 15 | 2.29 | 0.04 |
| 31-2 | 15 | 5.70 | 0.07 |
| 31-3 | 27 | 11.50 | 0.18 |

Example 32

EPO Encapsulation into Various Hybrid Gels for Use in Pharmacokinetic Test and Evaluation on Encapsulated Amount Lyophilized hybrid gels of Samples 31-1 to 31-3 prepared in Example 31 were each treated in the same manner as shown in Example 27-1 to encapsulate EPO. Among the EPO-encapsulating gels of each sample, three were randomly selected and calculated for the amount of EPO encapsulated per gel sample in the same manner as shown in Example 27-1. The results obtained are shown in Table 36.

TABLE 36

Amount of EPO encapsulated into hybrid gels for use in pharmacokinetic test

| Sample | HA derivative | Concentration of HA derivative (mg/mL) | n | Amount of encapsulated EPO (μg/gel) | |
|---|---|---|---|---|---|
| | | | | Mean | Standard deviation |
| 31-1 | HA-MA | 50.0 | 3 | 73.3 | 4.9 |
| 31-2 | HA-MA | 100.0 | 3 | 64.4 | 6.0 |
| 31-3 | HA-AM | 100.0 | 3 | 31.3 | 5.0 |

Comparative Example 5

Pharmacokinetic Test of Erythropoietin/CHP Complex in Rats

Comparative Example 5-1

Preparation of EPO/CHP Complex Solution and EPO Solution

CHP was dissolved in PBS (pH 7.4) at a concentration of 10 mg/mL.

A drug bulk solution of erythropoietin (EPO) (Chugai Pharmaceutical Co., Ltd., Japan), the above CHP solution and PBS were mixed to prepare a solution having an EPO polypeptide concentration of 25 μg/mL and a CHP concentration of 3 mg/mL. The resulting solution was allowed to stand overnight at 37° C. When SEC analysis was performed under the same SEC analysis conditions as shown in Example 7, free EPO (retention time: 7.1 minutes) was not detected and only EPO/CHP complexes (retention time: 5.6 minutes) were detected, thus confirming that all EPO molecules in the system formed complexes with CHP.

Another PBS solution having an EPO polypeptide concentration of 25 μg/mL was prepared separately.

Comparative Example 5-2

Pharmacokinetic Test

Figure 30:
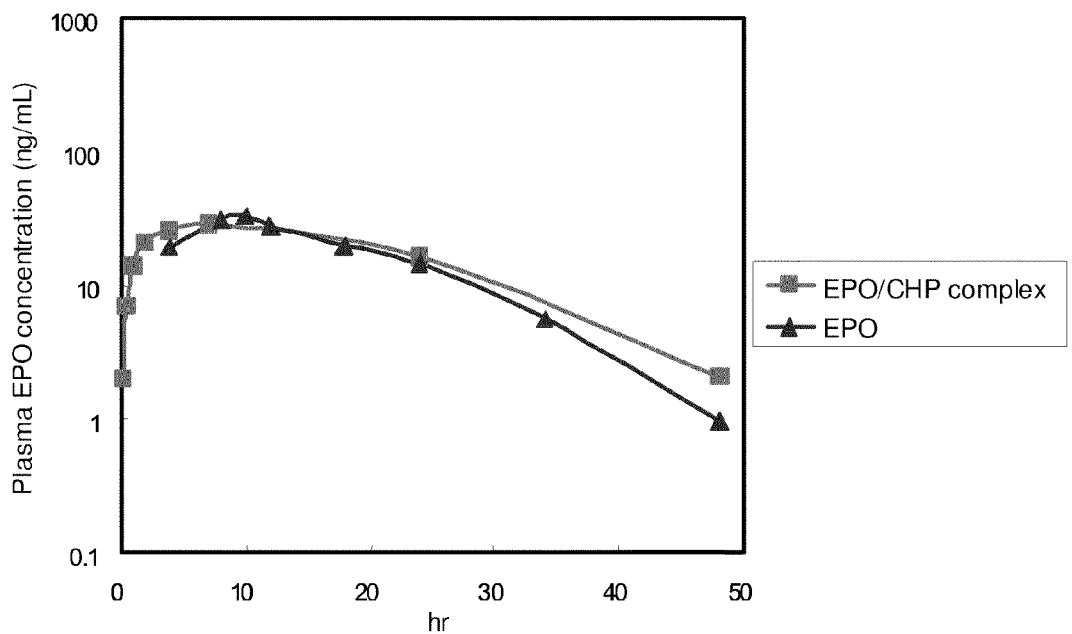
FIG. 30 is a graph showing the time course of plasma EPO concentration in rats subcutaneously administered with an EPO/CHP complex solution or an EPO solution.

The EPO/CHP complex solution and EPO solution prepared in Comparative Example 5-1 were each administered once at the dose indicated in Table 37 to normal rats (SD, 7 weeks of age, male) by the subcutaneous route. After administration, blood was collected over time from the jugular vein using a heparin-treated syringe. The resulting blood was treated to separate plasma, and the plasma EPO concentration was measured with an ELISA kit. FIG. 30 shows the time course of plasma EPO concentration (mean).

As a result, EPO/CHP complexes and free EPO were found to show almost the same time course of concentration in plasma, and no significant sustained release profile was observed even upon complexation with the nanogel. This indicated that replacement with biological components (e.g., albumin) would cause rapid release of EPO from the EPO/CHP complexes administered by the subcutaneous route, and thus suggested that complexation with CHP had little effect on the processes of subcutaneous absorption and in vivo clearance of EPO.

TABLE 37

Composition and dose of EPO/CHP complex solution and EPO solution

| Sample name | Administered sample | | | EPO dose (μg/kg) | n |
|---|---|---|---|---|---|
| | EPO concentration (μg/mL) | CHP concentration (mg/mL) | Administered volume (mL/kg) | | |
| EPO/CHP complex | 25.0 | 3.0 | 1.0 | 25.0 | 4 |
| EPO | 25.0 | 0.0 | 1.0 | 25.0 | 4 |

Example 33

Figure 31:
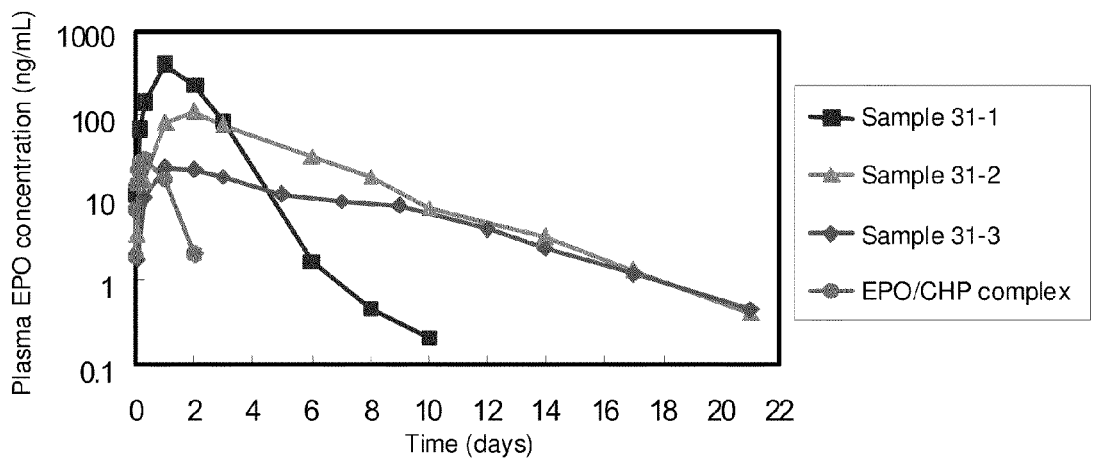
FIG. 31 is a graph showing the time course of plasma EPO concentration in rats subcutaneously implanted with various EPO-encapsulating hybrid gels.

Evaluation on Sustained Release Profile of Erythropoietin from Hybrid Gels in Rats The samples treated to encapsulate EPO in Example 32 were each implanted at the dose indicated in Table 38 under the skin of normal rats (SD, 7 weeks of age, male). After implantation, blood was collected over time from the jugular vein using a heparin-treated syringe. The resulting blood was treated to separate plasma, and the plasma EPO concentration was measured with an ELISA kit. FIG. 31 shows the time course of plasma EPO concentration (mean) upon implantation of each hybrid gel, along with the time course of plasma EPO concentration (mean) upon administration of the EPO/CHP complex solution in Comparative Example 5. Moreover, pharmacokinetic parameters (i.e., extrapolated area under the plasma concentration-time curve (AUC∞) and mean residence time (MRT)) were analyzed by WinNonlin Ver. 5.0.1 (Pharsight). The values obtained are shown in Table 39.

As a result, the release behavior of EPO from the hybrid gels was also found to have a sustained release profile in vivo, thus suggesting that the release rate can be controlled by the crosslinking density and/or the type of reaction used for gel crosslinking.

TABLE 38

Properties and dose of EPO-encapsulating hybrid gels

| Sample | Administered sample | | Gel density in swollen state (% w/w) | Number of administered gels (per animal) | EPO dose (μg/animal) | n |
|---|---|---|---|---|---|---|
| | HA derivative | Crosslinking reaction | | | | |
| 31-1 | HA-MA | Michael addition | 2.29 | 3 | 219.9 | 4 |
| 31-2 | HA-MA | Michael addition | 5.70 | 3 | 193.2 | 4 |
| 31-3 | HA-AM | Condensation | 11.50 | 6 | 187.8 | 4 |

TABLE 39

Pharmacokinetic parameters of EPO-encapsulating hybrid gels

| Sample | EPO dose (μg/animal) | AUC∞ (ng · hr/kg) | MRT (hr) |
|---|---|---|---|
| 31-1 | 219.9 | 16906.7 | 39.9 |
| 31-2 | 193.2 | 11138.3 | 101.8 |
| 31-3 | 187.8 | 3671.0 | 138.5 |

The invention claimed is:

1. A composition comprising
a hyaluronic acid having a crosslinking group(s) and a hydrophilic polysaccharide having a hydrophobic group(s),
wherein the hyaluronic acid having a crosslinking group(s) is prepared by a crosslinkage formation reaction of hyaluronic acid having a crosslinkable group(s) in the presence of the hydrophilic polysaccharide, wherein the hydrophilic polysaccharide optionally has one or more crosslinkable group(s);
wherein each crosslinkable group is selected independently from the group consisting of an amino group, a mercapto group, a formyl group, a group containing a carbon-carbon double bond, a group containing a carbon-carbon triple bond, and —CONHNH$_2$;
wherein the hydrophilic polysaccharide is obtainable by introducing a hydrophobic group(s) into a polysaccharide selected from the group consisting of pullulan, amylopectin, amylose, dextran, mannan, levan, inulin, chitin, chitosan, and dextrin; and
wherein the hyaluronic acid having a crosslinking group(s) is capable of forming a salt;
wherein the hydrophilic polysaccharide has 1.38 to 30 hydrophobic groups per 100 monosaccharides; and
wherein the hydrophobic group is introduced by converting one or more hydroxy groups in the hydrophilic polysaccharide into -OX, wherein X is selected from the group consisting of:

—CO—X$^1$—R$^2$;

—CO—R$^3$—COxX$^3$—R$^2$;   —CO—X$^1$—R$^3$—CO—X$^3$—R$^2$; —COR$^3$—X$^2$—CO—X$^3$—R$^2$; and —CO—X$^1$—R$^3$—X$^2$—CO—X$^3$—R$^2$ —wherein R$^2$ is a cholesteryl group; —R$^3$ is a divalent C$_{2-50}$ hydrocarbon group; —X$^1$, X$^2$ and X$^3$ are each independently selected from O and N(R$^4$); and —R$^4$ is a hydrogen atom or a C$_{1-6}$ alkyl group.

2. The composition according to claim 1, wherein the hydrophilic polysaccharide having a hydrophobic group(s) forms a particulate.

3. The composition according to claim 1, wherein the hydrophilic polysaccharide is obtainable by introducing a hydrophobic group(s) into a hydrophilic polysaccharide, which is selected from pullulan and dextrin.

4. The composition according to claim 1, wherein the hydrophobic group is a group containing a C$_{8\text{-}50}$ hydrocarbon group or a group containing a steryl group.

5. The composition according to claim 3, wherein the hydrophilic polysaccharide pullulan.

6. The composition according to claim 1, wherein the crosslinkable group is introduced by converting one or more carboxy groups in hyaluronic acid into —CO—Y, wherein the group Y is selected from the group consisting of:
—X$^{11}$—R$^{12}$—Y$^2$;
—X$^{11}$—R$^{12}$—X$^{12}$—CO—R$^{13}$—Y$^2$;
—X$^{11}$—R$^{12}$—X$^{12}$—C(=NR$^{24}$)—R$^{13}$—Y$^2$;
—X$^{11}$—R$^{12}$—CO—X$^{13}$—R$^{13}$—Y$^2$;
—X$^{11}$—R$^{12}$—X$^{12}$—CO—X$^{13}$—R$^{13}$—Y$^2$;
—N(R$^{11}$)N(R$^{14}$)CO—R$^{12}$—Y$^2$;
—N(R$^{11}$)N(R$^{14}$)CO—R$^{12}$—CON(R$^{15}$)N(R$^{16}$)CO—R$^{13}$—Y$^2$; and
—N(R$^{11}$)N(R$^{14}$)CO—R$^{12}$—CON(R$^{15}$)N(R$^{16}$)C(=NR$^{24}$)—R$^{13}$—Y$^2$
wherein X$^{11}$, X$^{12}$ and X$^{13}$ are each independently selected from O and N(R$^{11}$);
Y$^2$ is selected from an amino group, a mercapto group, a formyl group, —CONHNH$_2$, a group containing a carbon-carbon double bond, and a group containing a carbon-carbon triple bond;
R$^{11}$, R$^{14}$, R$^{15}$, R$^{16}$ and R$^{24}$ are each independently selected from a hydrogen atom or a C$_{1-6}$ alkyl group;
R$^{12}$ is a divalent C$_{2\text{-}50}$ hydrocarbon group or a divalent C$_{2\text{-}50}$ polyalkyleneoxy group;
R$^{13}$ is a divalent C$_{1\text{-}50}$ hydrocarbon group, a divalent C$_{2\text{-}50}$ polyalkyleneoxy group or —CH(R$^{25}$)—CH$_2$—S—CH$_2$—R$^{26}$—CH$_2$—; wherein if R$^{12}$ and R$^{13}$ are divalent C$_{2\text{-}50}$ hydrocarbon groups, the hydrocarbon groups may each independently partially contain a polyalkyleneoxy moiety by insertion of 1 to 10 oxygen atoms; or
—R$^{13}$—Y$^2$ together represent —CH(NH$_2$)CH$_2$SH or —CH(NH$_2$)CH$_2$CH$_2$SH; or
—X$^{11}$—R$^{12}$—Y$^2$ together represent a cysteine, homocysteine or glutathione group whose terminal amino group is used for attachment;
R$^{25}$ is a hydrogen atom or a C$_{1-6}$ alkyl group;
R$^{26}$ is —(CH(R$^{27}$))$_m$— or a divalent C$_{2\text{-}10}$ hydrocarbon group which may partially contain a polyalkyleneoxy moiety by insertion of 1 to 3 oxygen atoms;
m is an integer of 1 to 10; and
R$^{27}$ is independently selected from a hydrogen atom, a hydroxy group or a C$_{1-6}$ alkyl group.

7. The composition according to claim 6, wherein the group Y is selected from the group consisting of:
—NH—CH$_2$—CH$_2$—O—CO—C(R$^{17}$)=CH$_2$;
—NH—NH—CO—(CH$_2$)$_4$—CO—NH—NH$_2$;
—NH—NH—CO—(CH$_2$)$_4$—CO—NH—NH—C(=NH)—(CH$_2$)$_3$—SH;
—NH—(CH$_2$—CH$_2$—O)$_2$—CH$_2$—CH$_2$—NH$_2$;
—NH—(CH$_2$—CH$_2$—O)$_2$—CH$_2$—CH$_2$—NH—C(=NH)—(CH$_2$)$_3$—SH;
—NH—(CH$_2$—CH$_2$—O)$_2$—CH$_2$—CH$_2$—NH—CO—CH$_2$—SH; and
—NH—CH$_2$—CH$_2$—O—CO—CH(R$^{17}$)—CH$_2$—S—CH$_2$—CH(OH)—CH(OH)—CH$_2$—SH
wherein R$^{17}$ is a hydrogen atom or a C$_{1-6}$ alkyl group.

8. The composition according to claim 1, wherein the crosslinkable group is introduced by converting one or more hydroxy groups in the hydrophilic polysaccharide derivative or hyaluronic acid into —O—Z, wherein the group Z is selected from the group consisting of:
—CO—C(R$^{21}$)=CH$_2$;
—CH$_2$CH(OH)—R$^{22}$—Y$^1$;
—CH(CH$_2$OH)—R$^{22}$—Y$^1$;
—CONH—R$^{23}$—Y$^1$; and
—CO—R$^{23}$—Y$^1$
wherein Y$^1$ is selected from an amino group, a mercapto group, a formyl group, a group containing a carbon-carbon double bond, and a group containing a carbon-carbon triple bond;
R$^{21}$ is selected from a hydrogen atom or a C$_{1-6}$ alkyl group;
R$^{22}$ and R$^{23}$ are each a divalent C$_{2\text{-}50}$ hydrocarbon group or a divalent C$_{2\text{-}50}$ polyalkyleneoxy group, wherein the divalent C$_{2\text{-}50}$ hydrocarbon group may partially contain a polyalkyleneoxy moiety by insertion of 1 to 10 oxygen atoms.

9. The composition according to claim 8, wherein Y$^1$ is a group containing a carbon-carbon double bond, which is selected from the group consisting of:
—X$^{14}$—CO—C(R$^{18}$)=CH$_2$
wherein X$^{14}$ is selected from O and N(R$^{19}$); R$^{18}$ is a hydrogen atom or a C$_{1-6}$ alkyl group; and R$^{19}$ is a hydrogen atom or a C$_{1-6}$ alkyl group; and

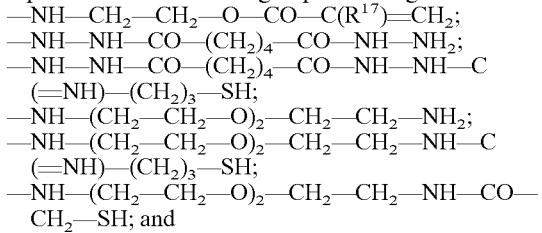

10. The composition according to claim 1, wherein the crosslinkage formation reaction is accomplished by adding a crosslinking agent to the solution.

11. The composition according to claim 1, wherein a hydrophilic polysaccharide having no crosslinking group is encapsulated by the hyaluronic acid having a crosslinking group(s).

12. The composition according to claim 1, wherein the hydrophilic polysaccharide has an intramolecular crosslinking group or has an intermolecular crosslinking group that is linked to the hydrophilic polysaccharide and the hyaluronic acid.

13. The composition according to claim 1, wherein the hydrophilic polysaccharide has a crosslinking group that is linked to only the hyaluronic acid.

14. The composition according to claim 13, wherein the hyaluronic acid has an intramolecular crosslinking group or has an intermolecular crosslinking group that is linked to the hyaluronic acid.

15. The composition according to claim 1, wherein the composition is in the form of a gel.

16. The composition according to claim 1, wherein the composition is used as a pharmaceutical preparation.

17. The composition according to claim 16, wherein the composition comprises a protein or a peptide.

* * * * *